US009127040B2

(12) United States Patent
Tarran et al.

(10) Patent No.: US 9,127,040 B2
(45) Date of Patent: Sep. 8, 2015

(54) REGULATION OF SODIUM CHANNELS BY PLUNC PROTEINS

(71) Applicant: The University of North Carolina at Chapel Hill, Chapel Hill, NC (US)

(72) Inventors: Robert Tarran, Chapel Hill, NC (US); Monroe Jack Stutts, Chapel Hill, NC (US); Scott Donaldson, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/345,975

(22) PCT Filed: Sep. 19, 2012

(86) PCT No.: PCT/US2012/056112
§ 371 (c)(1),
(2) Date: Mar. 20, 2014

(87) PCT Pub. No.: WO2013/043720
PCT Pub. Date: Mar. 28, 2013

(65) Prior Publication Data
US 2014/0228276 A1    Aug. 14, 2014

Related U.S. Application Data

(60) Provisional application No. 61/536,647, filed on Sep. 20, 2011.

(51) Int. Cl.
C07K 7/08      (2006.01)
C07K 14/435    (2006.01)
A61K 38/00     (2006.01)

(52) U.S. Cl.
CPC .................. *C07K 7/08* (2013.01); *C07K 14/435* (2013.01); *A61K 38/00* (2013.01)

(58) Field of Classification Search
CPC ............... A61K 38/1709; A61K 38/00; C07K 14/4703; C07K 14/435
USPC ........................... 435/375; 514/20.9; 530/395
See application file for complete search history.

(56) References Cited

U.S. PATENT DOCUMENTS

| | | | |
|---|---|---|---|
| 7,951,781 B2 | 5/2011 | McCray, Jr. et al. | |
| 2005/0192221 A1* | 9/2005 | McCray et al. | 514/12 |
| 2005/0244334 A1* | 11/2005 | Castillo et al. | 424/1.69 |
| 2008/0312093 A1 | 12/2008 | Inazawa et al. | |
| 2009/0110756 A1 | 4/2009 | McCray, Jr. et al. | |

FOREIGN PATENT DOCUMENTS

WO    WO 2010/138794 A2    12/2010

OTHER PUBLICATIONS

BPI fold-containing family A member 1, UniProt database, Protein Accession Q9NP55, pp. 1-9, accessed on Jun. 17, 2014.*
Shigeru Araga, A Complementary Peptide Vaccine That Induces T Cell Anergy and Prevents Experimental Allergic Neuritis in Lewis Rats, J Immunol 1999; 163:476-482.*
Helena Denac, Structure, function and pharmacology of voltage-gated sodium channels, Naunyn-Schmiedeberg's Arch Pharmacol (2000) 362 :453-479.*
Bingle et al., "Characterisation of the human plunc gene, a gene product with an upper airways and nasopharyngeal restricted expression pattern," Biochim. Biophys. Acta 1493:363-367 (2000).
Bingle et al., "Phylogenetic and evolutionary analysis of the PLUNC gene family." Protein Sci. 13: 422-430 (2004).
Bingle et al., "PLUNC: a novel family of candidate host defence proteins expressed in the upper airways and nasopharynx," Hum. Mol. Genet. 11: 937-943 (2002).
Final Office Corresponding to U.S. Appl. No. 13/321,617; Mailing Date: Jan. 29, 2014; 6 Pages.
Gaillard et al., The Soluble Protein SPLUNC1 Regulates ENaC in Human Bronchial Epithelial Cell Cultures, presented at the 2007 North American Cystic Fibrosis Conference (Oct. 4, 2007).
Garcia-Caballero et al., "ENaC proteolytic regulation by channel-activating protease 2," J. Gen. Physiol. 132:521-535 (2008).
Garcia-Caballero et al., "SPLUNC1 regulates airway surface liquid volume by protecting ENaC from proteolytic cleavage," Proc. Natl. Acad. Sci. USA 106:11412-11417 (2009).
International Preliminary Report on Patentability Corresponding to International Application No. PCT/US2010/036531; Date of Mailing: Dec. 8, 2011; 8 Pages.
International Preliminary Report on Patentability Corresponding to International Application No. PCT/US2012/056112; Date of Mailing: Apr. 3, 2014; 7 Pages.
International Search Report and Written Opinion Corresponding to International Application No. PCT/US2012/056112; Date of Mailing: Jan. 11, 2013; 9 Pages.
International Search Report and Written Opinion Corresponding to International Application No. PCT/US2010/036531; Date of Mailing: Feb. 18, 2011; 14 Pages.
Lee et al. "Genome-wide association study of copy number variations associated with pulmonary function measures in Korea Associated Resource (KARE) cohorts", *Genomics*, 97, (2011), 101-105.
Non-Final Office Action Corresponding to U.S. Appl. No. 13/321,617; Mailing Date: Jun. 18, 2013; 6 Pages.
Non-Final Office Action Corresponding to U.S. Appl. No. 13/321,617; Mailing Date: Sep. 11, 2014; 7 pages.
Passero et al., "Plasmin activates epithelial $Na^+$ channels by cleaving the $\gamma$ subunit," J. Biol. Chem. 283:36586-36591 (2008).
Pochynyuk et al., Binding and direct activation of the epithelial $Na^+$ channel (ENaC) by phosphatidylinositides, J. Physiol. 580:365-372 (2007).

(Continued)

*Primary Examiner* — James H Alstrum Acevedo
*Assistant Examiner* — Erinne Dabkowski
(74) *Attorney, Agent, or Firm* — Myers Bigel Sibley & Sajovec, P.A.

(57) ABSTRACT

The present invention relates to the ability of PLUNC proteins, such as SPLUNC1 and SPLUNC2, to bind to sodium channels and inhibit activation of the sodium channels. The invention further relates to methods for regulating of sodium absorption and fluid volume and treating disorders responsive to modulating sodium absorption by modulating the binding of PLUNC proteins to sodium channels.

16 Claims, 24 Drawing Sheets

(56) References Cited

OTHER PUBLICATIONS

Rollins, "Regulation of the epithelial sodium channel (ENaC) by the Short Palate, Lung, and Nasal Epithelial Clone (SPLUNC1)," Master's Thesis, Sep. 2010.

Schreiber et al., "The first-nucleotide binding domain of the cystic-fibrosis transmembrane conductance regulator is important for inhibition of the epithelial $Na^+$ channel," Proc. Natl. Acad. Sci. USA 96:5310-5315 (1999).

Daviskas et al. "Mucociliary clearance in patients with chronic asthma: Effects of $\beta_2$ agonists", Respirology 10:426-435 (2005).

Daviskas et al. "Hyperosmolar Agents and Clearance of Mucus in the Diseased Airway", J. Aerosol Medicine 19(1):100-109 (2006).

Daviskas et al. "Inhaled mannitol changes the sputum properties in asthmatics with mucus hypersecretion", Respirology 12:683-691 (2007).

Kunzelmann et al. "Electrolyte Transport in the Mammalian Colon: Mechanisms and Implications for Disease", Physiol. Rev. 82:245-289 (2002).

Mall et al. "Development of Chronic Bronchitis and Emphysema in $\beta$-Epithelial $Na^+$ Channel-Overexpressing Mice", Am. J. Respir. Crit. Care Med. 177:730-742 (2008).

* cited by examiner

N-GGLPVPLDQTLPLNVNPALPLSPTGLAGSLTNALSNGLLSGGLLGILENLPLLDILKPGGGTSGGLLGGLLG

```
A26       4 GALPHPL-QRLRTPPPP---NPA 22
            G LP PL Q L      P   NPA
SPLUNC1  22 GGLPVPLDQTL-----PLNVNPA 39
            G P         +    PL V
Y43      11 GTPPRFLNLI-----PLLV 24
```

REGULATION OF SODIUM CHANNELS BY PLUNC PROTEINS

RELATED APPLICATIONS

This application is a 35 U.S.C. §371 national phase application of PCT Application PCT/US2012/056112, filed Sep. 19, 2012, which claims the benefit under 35 U.S.C. §119(e) of U.S. Provisional Patent Application Ser. No. 61/536,647, filed Sep. 20, 2011. The entire contents of each of these applications is incorporated herein by reference.

FIELD OF THE INVENTION

The present invention relates to the ability of PLUNC proteins, such as SPLUNC1 and SPLUNC2, to bind to sodium channels and inhibit activation of the sodium channels. The invention further relates to methods for regulating of sodium absorption and fluid volume and treating disorders responsive to modulating sodium absorption by modulating the binding of PLUNC proteins to sodium channels.

BACKGROUND OF THE INVENTION

Epithelial mucosal surfaces are lined with fluids whose volume and composition are precisely controlled. In the airways, a thin film of airway surface liquid helps protect mammalian airways from infection by acting as a lubricant for efficient mucus clearance (Chmiel et al., *Respir. Res.* 4:8 (2003); Knowles et al., *J. Clin. Invest.* 109:571 (2002)). This layer moves cephalad during mucus clearance and excess liquid that accumulates as two airways converge is eliminated by $Na^+$-led airway surface liquid absorption with $Na^+$ passing through the epithelial $Na^+$ channel (ENaC) (Knowles et al., *J. Clin. Invest*, 109:571 (2002)). How ENaC activity is sensed and controlled by the airways is poorly understood. However, there is evidence that reporter molecules in the airway surface liquid can serve as volume sensing signals whose dilution or concentration can alter specific cell surface receptors which control ion transport rates to either absorb or secrete airway surface liquid as needed (Chambers et al., *Respir. Physiol. Neurobiol*, 159:256 (2007)). ENaC must be cleaved by intracellular furin-type proteases and/or extracellular channel activating proteases (CAPs) such as prostasin to be active and to conduct $Na^+$ (Planes et al., *Curr. Top. Dev. Biol.* 78:23 (2007); Rossier, *Proc. Am. Thorac. Soc.* 1:4 (2004); Vallet et al., *Nature* 389:607 (1997); Chraibi et al., *J. Gen. Physiol.* 111:127 (1998)). ENaC can also be cleaved and activated by exogenous serine proteases such as trypsin, an action that is attenuated by the protease inhibitor aprotinin (Vallet et al., *Nature* 389:607 (1997)). When human bronchial epithelial cultures are mounted in Ussing chambers where native airway surface liquid is washed away, ENaC is predominantly active, suggesting that cell attached proteases are predominant (Bridges et al., *Am. J. Physiol. Lung Cell. Mol. Physiol.* 281:L16 (2001); Donaldson et al., *J. Biol. Chem.* 277:8338 (2002)). In contrast, under thin film conditions, where native airway surface liquid is present, ENaC activity is reduced, suggesting that airway surface liquid contains soluble proteases inhibitors (Myerburg et al., *J. Biol. Chem.* 281:27942 (2006); Tarran et al., *J. Gen. Physiol.* 127:591 (2006)).

The Palate Lung and Nasal epithelial Clone (PLUNC) family are secreted proteins that are subdivided into short (SPLUNCs) and long (LPLUNCs) members which contain either one or two domains respectively (Bingle et al., *Biochim. Biophys. Acta* 1493:363 (2000); Weston et al., *J. Biol. Chem.* 274:13698 (1999)). The original PLUNC gene which is now called SPLUNC1 comprises up to 10% of total protein in the airway surface liquid and can readily be detected in both nasal lavage and tracheal secretions (Bingle, C. D., and Craven, C. J. (2002) PLUNC: a novel family of candidate host defense proteins expressed in the upper airways and nasopharynx *Hum Mol Genet* 11, 937; Campos, M. A., et al. (2004) Purification and characterization of PLUNC from human tracheobronchial secretions *Am J Respir Cell Mol Biol* 30, 184; Lindahl, M., Stahlbom, B., and Tagesson, C. (2001) Identification of a new potential airway irritation marker, palate lung nasal epithelial clone protein, in human nasal lavage fluid with two-dimensional electrophoresis and matrix-assisted laser desorption/ionization-time of flight *Electrophoresis* 22, 1795). SPLUNC1 is expressed in both submucosal glands, the superficial epithelia and in neutrophils and in theory, is present in the correct regions of the lung to be a volume sensing molecule since it can be secreted onto the mucosal surface of the superficial epithelial where ENaC is expressed (Bartlett et al., *J. Leukoc. Biol.* 83:1201 (2008); Bingle et al., *J. Pathol.* 205:491 (2005)).

The present invention addresses previous shortcomings in the art by disclosing the regulation of sodium channels by PLUNC proteins and the manipulation of this pathway to regulate sodium absorption and fluid volume and treat disorders responsive to modulating sodium absorption.

SUMMARY OF THE INVENTION

The present invention is based, in part, on the discovery of the ability of PLUNC proteins to regulate the activity of sodium channels. Accordingly, in one aspect the invention relates to a method of inhibiting the activation of a sodium channel, comprising contacting a sodium channel with a PLUNC protein or a functional fragment thereof. In one embodiment, the sodium channel is an epithelial sodium channel (ENaC). In another embodiment, the PLUNC protein is SPLUNC1 or SPLUNC2. In one embodiment, the PLUNC protein or a functional fragment thereof binds to the sodium channel.

Another aspect of the invention relates to a method of inhibiting sodium absorption through a sodium channel, comprising contacting the sodium channel with a PLUNC protein or a functional fragment thereof. In one embodiment, the PLUNC protein or a functional fragment thereof binds to the sodium channel.

A further aspect of the invention relates to a method of increasing the volume of fluid lining an epithelial mucosal surface, comprising contacting a sodium channel present on the epithelial mucosal surface with a PLUNC protein or a functional fragment thereof. In one embodiment, the PLUNC protein or a functional fragment thereof binds to the sodium channel.

Another aspect of the invention relates to a method of reducing the level of a sodium channel present on the surface of a cell, comprising contacting the sodium channel with a PLUNC protein or a functional fragment thereof. In one embodiment, the PLUNC protein or a functional fragment thereof binds to the sodium channel.

A further aspect of the invention relates to a method of treating a disorder responsive to inhibition of sodium absorption across an epithelial mucosal surface in a subject in need thereof, comprising delivering to the subject a therapeutically effective amount of a PLUNC protein or a functional fragment thereof. In one embodiment, the PLUNC protein or a functional fragment thereof binds to the sodium channel.

Another aspect of the invention relates to a method of regulating salt balance, blood volume, blood pressure, and/or colonic motility in a subject in need thereof, comprising delivering to the subject a therapeutically effective amount of a PLUNC protein or a functional fragment thereof. In one embodiment, the PLUNC protein or a functional fragment thereof binds to the sodium channel.

An additional aspect of the invention relates to a method of increasing the activation of a sodium channel, comprising inhibiting the binding of a PLUNC protein to the sodium channel.

A further aspect of the invention relates to a method of increasing sodium absorption through a sodium channel, comprising inhibiting the binding of a PLUNC protein to the sodium channel, thereby activating the sodium channel.

Another aspect of the invention relates to a method of decreasing the volume of fluid lining an epithelial mucosal surface, comprising inhibiting the binding of a PLUNC protein to a sodium channel present in the epithelial mucosal surface, thereby activating the sodium channel.

A further aspect of the invention relates to a method of increasing the level of a sodium channel present on the surface of a cell, comprising inhibiting the binding of a PLUNC protein to the sodium channel present on the surface of the cell.

An additional aspect of the invention relates to a method of treating a disorder responsive to activation of sodium absorption in a subject in need thereof, comprising inhibiting the activity of a PLUNC protein in the subject.

Another aspect of the invention relates to a method of regulating salt balance, blood volume, blood pressure (e.g., by inducing natriuresis), and/or colonic motility in a subject in need thereof, comprising inhibiting the activity of a PLUNC protein in the subject.

A further aspect of the invention relates to a method of enhancing the sense of taste in a subject, comprising inhibiting the activity of a PLUNC protein in the subject.

An additional aspect of the invention relates to a polypeptide consisting essentially of the sodium channel binding domain of a PLUNC protein, as well as a polynucleotide encoding the polypeptide and a vector and/or cell comprising the polynucleotide.

Another aspect of the invention relates to a compound that mimics the sodium channel binding domain of a PLUNC protein and binds to a sodium channel, wherein cleavage of the sodium channel by a protease is inhibited when bound to the compound.

An additional aspect of the invention relates to a SPLUNC1 protein in which the amino acid sequence of the hinge region has been modified to decrease the pH sensitivity of at least one bioactivity of SPLUNC1.

A further aspect of the invention relates to a polypeptide consisting essentially of a PLUNC protein binding domain of a sodium channel, as well as a polynucleotide encoding the polypeptide and a vector and/or cell comprising the polynucleotide.

An additional aspect of the invention relates to a compound that mimics a PLUNC protein binding domain of a sodium channel and binds to a PLUNC protein, wherein binding of PLUNC protein to the sodium channel is inhibited when bound to the compound.

Another aspect of the invention relates to a kit comprising the polypeptide, polynucleotide, vector, cell, peptidomimetic, or compound of the invention.

Another aspect of the invention relates to the use of a PLUNC protein or a functional fragment thereof for the preparation of a medicament to treat a disorder responsive to inhibition of sodium absorption in a subject in need thereof.

Another aspect of the invention relates to the use of an inhibitor of a PLUNC protein for the preparation of a medicament to treat a responsive to activation of sodium absorption in a subject in need thereof.

These and other aspects of the invention are set forth in more detail in the description of the invention below.

BRIEF DESCRIPTION OF THE DRAWINGS

FIGS. 18A-18C show the identification of the active site of SPLUNC1 (SEQ ID NO:11). A, SPLUNC1 truncants were constructed. All truncants had deletions starting from the C-terminus, retained the N-terminal signal sequence and were all spontaneously secreted from oocytes into the media (as determined by western blot). B, The effect of these truncants on the amiloride-sensitive (ENaC) current was determined by 2 electrode voltage clamp. Deletion of up to 85% of SPLUNC1 resulted in similar inhibition of ENaC as full length SPLUNC1. All n=10-14. C, An 18 amino acid peptide, corresponding to region 22-39, dubbed S18, also inhibits both basal and trypsin-stimulated ENaC current when incubated in the oocyte bath for 1 h at 10 μM. Open bars, control. Closed bars, S18. n=9. *p<0.05 different to control.

DETAILED DESCRIPTION OF THE INVENTION

Figure 1:
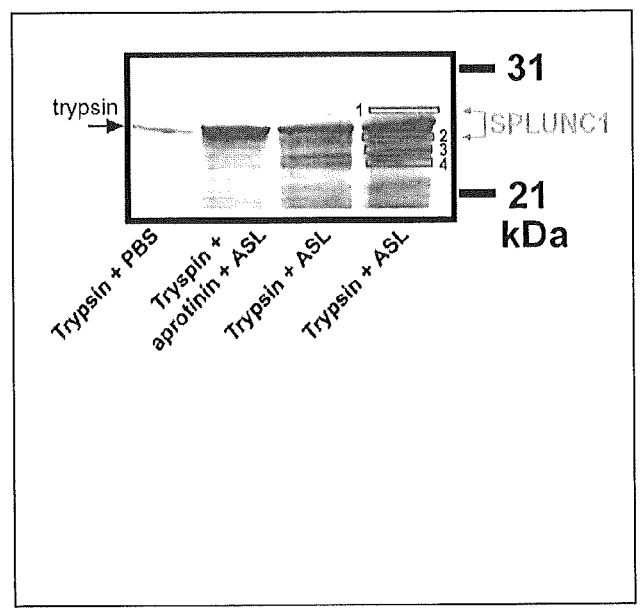
FIG. 1 shows that SPLUNC1 is present in the airway surface liquid of human bronchial cultures. Airway surface liquid was incubated with trypsin-agarose beads±aprotinin and proteins were separated on 15% SDS gel and visualized with a silver stain. The outlined bands were then cut out and analyzed by MALDI-MS/MS and the proteins identified are shown in Table 2. SPLUNC1 was detected in Bands 1 & 2, and its binding to trypsin was attenuated in the presence of aprotinin.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. §1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed, (Cold Spring Harbor, N.Y., 1989); Ausubel et al. Current Protocols in Molecular Biology (Green Publishing Associates, Inc. and John Wiley & Sons, Inc., New York).

I. Definitions

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in binding activity (e.g., to a sodium channel or PLUNC protein) of at least about 50% or more as compared to the activity of a polypeptide consisting of the recited sequence.

The term "modulate," "modulates," or "modulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

The term "contact" or grammatical variations thereof as used with respect to a PLUNC protein and a sodium channel, refers to bringing the PLUNC protein and the sodium channel in sufficiently close proximity to each other for one to exert a biological effect on the other. In some embodiments, the term contact means binding of the PLUNC protein to the sodium channel.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

By the terms "treat," "treating," or "treatment of," it is intended that the severity of the subject's condition is reduced or at least partially improved or modified and that some alleviation, mitigation or decrease in at least one clinical symptom is achieved.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid or nucleotide sequence of this invention.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

An isolated cell refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the invention. In other embodiments, such fragments can comprise, consist essentially of, and/or consist of oligonucleotides having a length of less than about 200, 150, 100, 75, 60, 50, 45, 40, 35, 30, 25, 20, 15, 12, 10, 8, or less consecutive nucleotides of a nucleic acid or nucleotide sequence according to the invention.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention. In other embodiments, such fragments can comprise, consist essentially of, and/or consist of peptides having a length of less than about 200, 150, 100, 75, 60, 50, 45, 40, 35, 30, 25, 20, 15, 12, 10, 8, 6, 4, or less consecutive amino acids of a polypeptide or amino acid sequence according to the invention.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990).

In some embodiments, a polynucleotide of this invention can be delivered to a cell in vivo by lipofection. Synthetic cationic lipids designed to limit the difficulties and dangers encountered with liposome-mediated transfection can be used to prepare liposomes for in vivo transfection of a nucleotide sequence of this invention (Felgner et al., *Proc. Natl. Acad. Sci. USA* 84:7413 (1987); Mackey, et al., *Proc. Natl. Acad. Sci. U.S.A.* 85:8027 (1988); and Ulmer et al., *Science* 259:1745 (1993)). The use of cationic lipids may promote encapsulation of negatively charged nucleic acids, and also promote fusion with negatively charged cell membranes (Felgner et al., *Science* 337:387 (1989)). Particularly useful lipid compounds and compositions for transfer of nucleic acids are described in International Patent Publications WO95/18863 and WO96/17823, and in U.S. Pat. No. 5,459,127. The use of lipofection to introduce exogenous nucleotide sequences into specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules can be coupled to liposomes chemically.

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931).

It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

The term "transfection" or "transduction" means the uptake of exogenous or heterologous nucleic acid (RNA and/or DNA) by a cell. A cell has been "transfected" or "transduced" with an exogenous or heterologous nucleic acid when such nucleic acid has been introduced or delivered inside the cell. A cell has been "transformed" by exogenous or heterologous nucleic acid when the transfected or transduced nucleic acid imparts a phenotypic change in the cell and/or a change in an activity or function of the cell. The transforming nucleic acid can be integrated (covalently linked) into chromosomal DNA making up the genome of the cell or it can be present as a stable plasmid.

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide (e.g., binding to or inhibiting a sodium channel or a PLUNC protein). In particular embodiments, the "functional" polypeptide or "functional fragment" substantially retains all of the activities possessed by the unmodified peptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as protein binding and angiogenic activity can be measured using assays that are well known in the art and as described herein. In some embodiments, the term "functional fragment" also encompasses compounds that are mimetics of a portion of the polypeptide (e.g., peptidomimetics) that have at least one biological activity that is substantially the same as an activity associated with the polypeptide.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

II. Decreasing Sodium Channel Activation

A first aspect of the invention relates to the ability of PLUNC proteins to bind to a sodium channel and prevent activation of the sodium channel, thereby inhibiting the flow of sodium ions. Thus, one aspect of the present invention relates to a method of inhibiting the activation of a sodium channel, comprising contacting (e.g., binding) a sodium channel with a PLUNC protein or a functional fragment thereof. In one embodiment, the sodium channel is an epithelial sodium channel (ENaC), e.g., human ENaC. In another embodiment, the sodium channel is one that is similar in sequence and/or structure to ENaC. The inhibition of sodium channel activation can be measured by any method known in the art or disclosed herein, including, without limitation, measuring sodium flow or change in potential across a membrane, across a cell, or across a natural or artificial lining. The inhibition can be at least about 20%, e.g., at least about 30%, 40%, 50%, 60%, 70%, 80%, 90%, or 100% relative to sodium channel activation in the absence of a PLUNC protein.

The PLUNC protein can be any protein from the PLUNC family that can bind to and inhibit the activation of sodium channel, e.g., binds to β-ENaC. In one embodiment, the PLUNC protein is a human PLUNC protein. In another embodiment, the PLUNC protein is SPLUNC1 or SPLUNC2. The PLUNC protein can be a naturally occurring PLUNC protein or a PLUNC protein in which the amino acid sequence has been modified (e.g., with insertions, deletions, substitutions, or any combination thereof). In certain embodiments, the modified PLUNC protein exhibits a modulation on one or more bioactivity of the PLUNC protein, e.g., a decrease in pH sensitivity. In other embodiments, no more than 20 amino acids of the naturally occurring PLUNC sequence are modified (inserted, deleted or substituted), e.g., no more than 15, 10, 9, 8, 7, 6, or 5 amino acids.

The method of inhibiting the activation of a sodium channel can be carried out, e.g., on an isolated sodium channel, a sodium channel in an artificial membrane, or a sodium channel in a cell. In one embodiment, the sodium channel is present in an isolated cell, e.g., a cultured primary cell or cell line. In another embodiment, the isolated cell is part of an epithelial cell culture, e.g., a natural or artificial epithelial lining, e.g., a cell culture in a device (such as an Ussing chamber) in which characteristics such as ion flow and/or potential can be measured across lining. In another embodiment, the cell is part of an isolated tissue or a tissue culture. In a further embodiment, the cell can be present in an animal, e.g., an animal that is a disease model or a subject in need of treatment.

In one embodiment, the step of contacting (e.g., binding) the sodium channel with a PLUNC protein comprises delivering the PLUNC protein or a functional fragment or homolog thereof to a cell comprising the sodium channel. In another embodiment, the contacting step (e.g., binding) comprises delivering a polynucleotide encoding the PLUNC protein or a functional fragment or homolog thereof to a cell comprising the sodium channel.

As used herein, the term "homolog" is used to refer to a polypeptide which differs from a naturally occurring polypeptide by minor modifications to the naturally occurring polypeptide, but which significantly retains a biological activity of the naturally occurring polypeptide. Minor modifications include, without limitation, changes in one or a few amino acid side chains, changes to one or a few amino acids (including deletions, insertions, and/or substitutions), changes in stereochemistry of one or a few atoms, and minor derivatizations, including, without limitation, methylation, glycosylation, phosphorylation, acetylation, myristoylation, prenylation, palmitation, amidation, and addition of glycosylphosphatidyl inositol. The term "substantially retains," as used herein, refers to a fragment, homolog, or other variant of a polypeptide that retains at least about 20% of the activity of the naturally occurring polypeptide (e.g., binding to a sodium channel), e.g., about 30%, 40%, 50% or more. Other biological activities, depending on the polypeptide, may include pH sensitivity, enzyme activity, receptor binding, ligand binding, induction of a growth factor, a cell signal transduction event, etc.

In one embodiment, the method comprises delivering to a cell comprising a sodium channel an isolated PLUNC protein. In exemplary embodiments, the PLUNC protein comprises, consists essentially of, or consists of the publicly known amino acid sequence of the PLUNC protein (e.g., as disclosed in GenBank and disclosed herein) or a functional fragment thereof. In another embodiment, the isolated PLUNC protein comprises, consists essentially of, or consists of an amino acid sequence that is at least 70% identical, e.g., at least 75%, 80%, 85%, 90%, 95%, 96%, 97%, 98%, or 99% identical to the publicly known amino acid sequence or a functional fragment thereof.

The amino acid sequence of human SPLUNC1 (SEQ ID NO:1) and human SPLUNC2 (SEQ ID NO:2) are disclosed below. The conserved cysteine residues that are spaced 43 amino acids apart and may be important for activity are indicated.

contiguous amino acids of a PLUNC protein. In other embodiments, the fragment comprises no more than about 200, 150, 100, 75, 50, 45, 40, 35, 30, 25, 20, 15, 12, 10, 8, 6, or 4 contiguous amino acids of a PLUNC protein. In one embodiment, the fragment comprises, consists essentially of, or consists of a sequence from about residue 20 to about residue 41 of human SPLUNC1, e.g., about residue 22 to about residue 39, or the corresponding sequence (e.g., the approximately 20 amino acids immediately after the signal peptide) from another PLUNC protein.

In one embodiment, the functional fragment comprises, consists essentially of, or consists of the amino acid sequence GGLPVPLDQTLPLNVNPA (SEQ ID NO:11), corresponding to amino acids 22-39 of human SPLUNC1, or an amino acid sequence that has at least 70% sequence identity thereto, e.g., at least 75%, 80%, 85%, 90%, 95%, 96%, 97%, 98%, or 99% sequence identity thereto. In another embodiment, the functional fragment comprises, consists essentially of, or consists of the partial amino acid sequence LPVPLDQT (SEQ ID NO:14). Each of these amino acid residues has been shown to be important for ENaC inhibitory activity.

Likewise, those skilled in the art will appreciate that the present invention also encompasses fusion polypeptides (and polynucleotide sequences encoding the same) comprising a PLUNC protein (or a functional fragment thereof). For example, it may be useful to express the polypeptide (or functional fragment) as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of the polypeptide may be produced, e.g., fusion proteins comprising mal-

```
SPLUNC1
         10         20         30         40         50         60
MFQTGGLIVF YGLLAQTMAQ FGGLPVPLDQ TLPLNVNPAL PLSPTGLAGS LTNALSNGLL 70         80         90        100        110        120
SGGLLGILEN LPLLDILKPG GGTSGGLLGG LLGKVTSVIP GLNNIIDIKV TDPQLLELGL 130        140        150        160        170        180
VQSPDGHRLY VTIPLGIKLQ VNTPLVGASL LRLAVKLDIT AEILAVRDKQ ERIHLVLGDC 190        200        210        220        230        240
THSPGSLQIS LLDGLGPLPI QGLLDSLTGI LNKVLPELVQ GNVCPLVNEV LRGLDITLVH

250
DIVNMLIHGL QFVIKV

SPLUNC2
         10         20         30         40         50         60
MLQLWKLVLL CGVLTGTSES LLDNLGNDLS NVVDKLEPVL HEGLETVDNT LKGILEKLKV 70         80         90        100        110        120
DLGVLQKSSA WQLAKQKAQE AEKLLNNVIS KLLPTNTDIF GLKISNSLIL DVKAEPIDDG 130        140        150        160        170        180
KGLNLSFPVT ANVTVAGPII GQIINLKASL DLLTAVTIET DPQTHQPVAV LGECASDPTS 190        200        210        220        230        240
ISLSLLDKHS QIINKFVNSV INTLKSTVSS LLQKEICPLI RIFIHSLDVN VIQQVVDNPQ

HKTQLQTLI
```

The PLUNC proteins of the invention also include functional portions or fragments. The length of the fragment is not critical as long as it substantially retains the biological activity of the polypeptide (e.g., sodium channel binding activity). Illustrative fragments comprise at least about 4, 6, 8, 10, 12, 15, 20, 25, 30, 35, 40, 45, 50, 75, 100, 150, 200, or more tose binding protein (MBP) or glutathione-S-transferase. As another alternative, the fusion protein can comprise a reporter molecule. In other embodiments, the fusion protein can comprise a polypeptide that provides a function or activity that is the same as or different from the activity of the polypeptide, e.g., a targeting, binding, or enzymatic activity or function.

Likewise, it will be understood that the polypeptides specifically disclosed herein will typically tolerate substitutions in the amino acid sequence and substantially retain biological activity. To identify polypeptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the DNA sequence (or RNA sequence), according to the following codon table:

TABLE 1

| Amino Acid | | | Codons |
| --- | --- | --- | --- |
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

In identifying amino acid sequences encoding polypeptides other than those specifically disclosed herein, the hydropathic index of amino acids may be considered. The importance of the hydropathic amino acid index in conferring interactive biologic function on a protein is generally understood in the art (see, Kyte and Doolittle, *J. Mol. Biol.* 157:105 (1982); incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, id.), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the polypeptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±I); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional polypeptides beyond those specifically disclosed herein.

One aspect of the invention is based on the discovery that PLUNC proteins inhibit sodium channels in a pH sensitive manner. In particular, PLUNC proteins are able to inhibit sodium channels at neutral pH but not at acidic pHs. Without being bound by theory, it is thought that the PLUNC proteins undergo a conformational change at acidic pH that prevents exposure of the active site (e.g., amino acids 22-39 of human SPLUNC1) to sodium channels. Thus, in certain embodiments, the PLUNC protein of the present invention comprises a modified amino acid sequence that reduces or eliminates the inactivation of PLUNC proteins at acidic pHs. In one embodiment, a pH sensitive hinge region, e.g., one or more of amino acid residues K94, N103, N104, K138, Q140, N142, and D193, is modified to prevent a conformational change of the PLUNC protein at acidic pHs. In one embodiment, one or more amino acids in the hinge region is substituted, e.g., with alanine. In another embodiment, all of the amino acids in the hinge region are substituted, e.g., with alanine. The pH-insensitive modified PLUNC proteins are advantageously used to inhibit sodium channels under acidic conditions, e.g., as is found in the lungs of cystic fibrosis patients.

In embodiments of the invention, the polynucleotide encoding the PLUNC protein (or functional fragment) will hybridize to the nucleic acid sequences encoding PLUNC proteins that are known in the art or fragments thereof under standard conditions as known by those skilled in the art and encode a functional polypeptide or functional fragment thereof.

For example, hybridization of such sequences may be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and conditions represented by a wash stringency of 50% formamide with 5×Denhardt's solution, 0.5% SDS and 1×SSPE at 42° C., respectively) to the polynucleotide sequences encoding the PLUNC protein or functional fragments thereof specifically disclosed herein. See, e.g., Sambrook et al., Molecular Cloning: A Laboratory Manual 2nd Ed. (Cold Spring Harbor, N.Y., 1989).

In other embodiments, polynucleotide sequences encoding the PLUNC protein have at least about 70%, 80%, 85%, 90%, 95%, 96%, 97%, 98%, 99% or higher sequence identity with the publicly known nucleic acid sequences (disclosed in Gen-Bank) or functional fragments thereof and encode a functional polypeptide or functional fragment thereof.

Further, it will be appreciated by those skilled in the art that there can be variability in the polynucleotides that encode the polypeptides (and fragments thereof) of the present invention due to the degeneracy of the genetic code. The degeneracy of the genetic code, which allows different nucleic acid sequences to code for the same polypeptide, is well known in the literature (See, e.g., Table 1).

Likewise, the polypeptides (and fragments thereof) of the invention include polypeptides that have at least about 70%, 80%, 85%, 90%, 95%, 96%, 97%, 98%, 99% or higher amino acid sequence identity with the publicly known polypeptide sequences.

As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Those skilled in the art will appreciate that the isolated polynucleotides encoding the polypeptides of the invention will typically be associated with appropriate expression control sequences, e.g., transcription/translation control signals and polyadenylation signals.

It will further be appreciated that a variety of promoter/enhancer elements can be used depending on the level and tissue-specific expression desired. The promoter can be constitutive or inducible, depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

To illustrate, the polypeptide coding sequence can be operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter.

Inducible promoter/enhancer elements include hormone-inducible and metal-inducible elements, and other promoters regulated by exogenously supplied compounds, including without limitation, the zinc-inducible metallothionein (MT) promoter; the dexamethasone (Dex)-inducible mouse mammary tumor virus (MMTV) promoter; the T7 polymerase promoter system (see WO 98/10088); the ecdysone insect promoter (No et al., *Proc. Natl. Acad. Sci. USA* 93:3346 (1996)); the tetracycline-repressible system (Gossen et al., *Proc. Natl. Acad. Sci. USA* 89:5547 (1992)); the tetracycline-inducible system (Gossen et al., *Science* 268:1766 (1995); see also Harvey et al., *Curr. Opin. Chem. Biol*, 2:512 (1998)); the RU486-inducible system (Wang et al., *Nat. Biotech.* 15:239 (1997); Wang et al., *Gene Ther.*, 4:432 (1997)); and the rapamycin-inducible system (Magari et al., *J. Clin. Invest.* 100: 2865 (1997)).

Moreover, specific initiation signals are generally required for efficient translation of inserted polypeptide coding sequences. These translational control sequences, which can include the ATG initiation codon and adjacent sequences, can be of a variety of origins, both natural and synthetic.

The present invention further provides cells comprising the isolated polynucleotides and polypeptides of the invention. The cell may be a cultured cell or a cell in vivo, e.g., for use in therapeutic methods, diagnostic methods, screening methods, methods for studying the biological action of the PLUNC proteins, in methods of producing the polypeptides, or in methods of maintaining or amplifying the polynucleotides of the invention, etc. In another embodiment, the cell is an ex vivo cell that has been isolated from a subject. The ex vivo cell may be modified and then reintroduced into the subject for diagnostic or therapeutic purposes.

In particular embodiments, the cell is an untransformed epithelial cell or a cell from an epithelial cell line.

The isolated polynucleotide can be incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a PLUNC protein or sodium channel or functional fragment thereof operatively associated with the promoter, and, optionally, a termination sequence including a stop signal for RNA polymerase and a polyadenylation signal for polyadenylase.

Non-limiting examples of promoters of this invention include CYC1, HIS3, GAL1, GAL4, GAL10, ADH1, PGK, PHO5, GAPDH, ADC1, TRP1, URA3, LEU2, ENO, TPI, and alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, pathogenesis or disease related-promoters, cauliflower mosaic virus 35S, CMV 35S minimal, cassaya vein mosaic virus (CsVMV), chlorophyll a/b binding protein, ribulose 1,5-bisphosphate carboxylase, shoot-specific promoters, root specific promoters, chitinase, stress inducible promoters, rice tungro baciliform virus, plant super-promoter, potato leucine aminopeptidase, nitrate reductase, mannopine synthase, nopaline synthase, ubiquitin, zein protein, and anthocyanin promoters (useful for expression in plant cells).

Further examples of animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, baculovirus IE1 promoter, elongation factor 1 alpha (EF1) promoter, phosphoglycerate kinase (PGK) promoter, ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis and/or disease-related promoters, and promoters that exhibit tissue specificity, such as the elastase I gene control region, which is active in pancreatic acinar cells; the insulin gene control region active in pancreatic beta cells, the immunoglobulin gene control region active in lymphoid cells, the mouse mammary tumor virus control region active in testicular, breast, lymphoid and mast cells; the albumin gene promoter, the Apo AI and Apo AII control regions active in liver, the alpha-fetoprotein gene control region active in liver, the alpha 1-antitrypsin gene control region active in the liver, the beta-globin gene control region active in myeloid cells, the myelin basic protein gene control region active in oligodendrocyte cells in the brain, the myosin light chain-2 gene control region active in skeletal muscle, and the gonadotropic releasing hormone gene control region active in the hypothalamus, the pyruvate kinase promoter, the villin promoter, the promoter of the fatty acid binding intestinal protein, the promoter of smooth muscle cell α-actin, and the like. In addition, any of these expression sequences of this invention can be modified by addition of enhancer and/or regulatory sequences and the like.

Enhancers that may be used in embodiments of the invention include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may be derived from various genes native to the preferred hosts. In some embodiments of the invention, the termination control region may comprise or be derived from a synthetic sequence, a synthetic polyadenylation signal, an SV40 late polyadenylation signal, an SV40 polyadenylation signal, a bovine growth hormone (BGH) polyadenylation signal, viral terminator sequences, or the like.

It will be apparent to those skilled in the art that any suitable vector can be used to deliver the polynucleotide to a cell or subject. The vector can be delivered to cells in vivo. In other embodiments, the vector can be delivered to cells ex vivo, and then cells containing the vector are delivered to the subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Suitable vectors include plasmid vectors, viral vectors (e.g., retrovirus, alphavirus; vaccinia virus; adenovirus, adeno-associated virus and other parvoviruses, lentivirus, poxvirus, or herpes simplex virus), lipid vectors, poly-lysine vectors, synthetic polyamino polymer vectors, and the like.

Any viral vector that is known in the art can be used in the present invention. Protocols for producing recombinant viral vectors and for using viral vectors for nucleic acid delivery can be found in Ausubel et al., Current Protocols in Molecular Biology (Green Publishing Associates, Inc. and John Wiley & Sons, Inc., New York) and other standard laboratory manuals (e.g., Vectors for Gene Therapy. In: *Current Protocols in Human Genetics*. John Wiley and Sons, Inc.: 1997).

Non-viral transfer methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, poly-lysine conjugates, and artificial viral envelopes.

In particular embodiments, plasmid vectors are used in the practice of the present invention. For example, naked plasmids can be introduced into muscle cells by injection into the tissue. Expression can extend over many months, although the number of positive cells is typically low (Wolff et al., *Science* 247:247 (1989)). Cationic lipids have been demonstrated to aid in introduction of nucleic acids into some cells in culture (Feigner and Ringoid, *Nature* 337:387 (1989)). Injection of cationic lipid plasmid DNA complexes into the circulation of mice has been shown to result in expression of the DNA in lung (Brigham et al., *Am. J. Med. Sci.* 298:278 (1989)). One advantage of plasmid DNA is that it can be introduced into non-replicating cells.

In a representative embodiment, a nucleic acid molecule (e.g., a plasmid) can be entrapped in a lipid particle bearing positive charges on its surface and, optionally, tagged with antibodies against cell surface antigens of the target tissue (Mizuno et al., *No Shinkei Geka* 20:547 (1992); PCT publication WO 91/06309; Japanese patent application 1047381; and European patent publication EP-A-43075).

Liposomes that consist of amphiphilic cationic molecules are useful as non-viral vectors for nucleic acid delivery in vitro and in vivo (reviewed in Crystal, *Science* 270:404 (1995); Blaese et al., *Cancer Gene Ther.* 2:291 (1995); Behr et al., *Bioconjugate Chem.* 5:382 (1994); Remy et al., *Bioconjugate Chem.* 5:647 (1994); and Gao et al., *Gene Therapy* 2:710 (1995)). The positively charged liposomes are believed to complex with negatively charged nucleic acids via electrostatic interactions to form lipid:nucleic acid complexes. The lipid:nucleic acid complexes have several advantages as nucleic acid transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Feigner et al., *Proc. Natl. Acad. Sci. USA* 84:7413 (1987); Loeffler et al., *Meth. Enzymol.* 217:599 (1993); Feigner et al., *J. Biol. Chem.* 269:2550 (1994)).

Several groups have reported the use of amphiphilic cationic lipid:nucleic acid complexes for in vivo transfection both in animals and in humans (reviewed in Gao et al., *Gene Therapy* 2:710 (1995); Zhu et al., *Science* 261:209 (1993); and Thierry et al., *Proc. Natl. Acad. Sci. USA* 92:9742 (1995)). U.S. Pat. No. 6,410,049 describes a method of preparing cationic lipid:nucleic acid complexes that have a prolonged shelf life.

Expression vectors can be designed for expression of polypeptides in prokaryotic or eukaryotic cells. For example, polypeptides can be expressed in bacterial cells such as *E. coli*, insect cells (e.g., the baculovirus expression system), yeast cells, plant cells or mammalian cells. Some suitable host cells are discussed further in Goeddel, *Gene Expression Technology*: Methods in Enzymology 185, Academic Press, San Diego, Calif. (1990). Examples of bacterial vectors include pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast *S. cerevisiae* include pYepSec1 (Baldari et al., *EMBO J.* 6:229 (1987)), pMFa (Kuijan and Herskowitz, *Cell* 30:933 (1982)), pJRY88 (Schultz et al., *Gene* 54:113 (1987)), and pYES2 (Invitrogen Corporation, San Diego, Calif.). Baculovirus vectors available for expression of nucleic acids to produce proteins in cultured insect cells (e.g., Sf 9 cells) include the pAc series (Smith et al., *Mol. Cell. Biol.* 3:2156 (1983)) and the pVL series (Lucklow and Summers *Virology* 170:31 (1989)).

Examples of mammalian expression vectors include pWL-NEO, pSV2CAT, pOG44, pXT1, pSG (Stratagene) pSVK3, PBPV, pMSG, PSVL (Pharmacia), pCDM8 (Seed, *Nature* 329:840 (1987)) and pMT2PC (Kaufman et al., *EMBO J.* 6:187 (1987)). When used in mammalian cells, the expression vector's control functions are often provided by viral regulatory elements. For example, commonly used promoters are derived from polyoma, adenovirus 2, cytomegalovirus and Simian Virus 40.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

In addition to the regulatory control sequences discussed above, the recombinant expression vector can contain additional nucleotide sequences. For example, the recombinant expression vector can encode a selectable marker gene to identify host cells that have incorporated the vector.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA and RNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al., Molecular Cloning: A Laboratory Manual 2nd Ed. (Cold Spring Harbor, N.Y., 1989), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

Polypeptides and fragments of the invention can be modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

In one embodiment, the polynucleotides, vectors, polypeptides, or homologs thereof of the invention are administered directly to a subject. Generally, the compounds of the invention will be suspended in a pharmaceutically-acceptable carrier (e.g., physiological saline) and administered orally or by intravenous infusion, or administered subcutaneously, intramuscularly, intrathecally, intraperitoneally, intrarectally, intravaginally, intranasally, intragastrically, intratracheally, or intrapulmonarily. They can be delivered directly to the site of the disease or disorder, such as lungs, kidney, or intestines. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 µg/kg. Wide variations in the needed dosage are to be expected in view of the variety of polynucleotides, polypeptides, fragments, and homologs available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-; 20-, 50-, 100-, 150-, or more fold). Encapsulation of the polynucleotides, polypeptides, fragments, and homologs in a suitable delivery vehicle (e.g., polymeric microparticles or implantable devices) may increase the efficiency of delivery, particularly for oral delivery.

According to certain embodiments, the polynucleotides, vectors, polypeptides, or homologs thereof can be targeted to specific cells or tissues in vivo. Targeting delivery vehicles, including liposomes and viral vector systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry* 25:5500 (1986); Ho et al., *J. Biol. Chem.* 262:13979 (1987); Ho et al., *J. Biol. Chem.* 262:13973 (1987); and U.S. Pat. No. 4,957,735 to Huang et al., each of which is incorporated herein by reference in its entirety). Enveloped viral vectors can be modified to deliver a nucleic acid molecule to a target cell by modifying or substituting an envelope protein such that the virus infects a specific cell type. In adenoviral vectors, the gene encoding the attachment fibers can be modified to encode a protein domain that binds to a cell-specific receptor. Herpesvirus vectors naturally target the cells of the central and peripheral nervous system. Alternatively, the route of administration can be used to target a specific cell or tissue. For example, intracoronary administration of an adenoviral vector has been shown to be effective for the delivery of a gene cardiac myocytes (Maurice et al., *J. Clin. Invest.* 104:21 (1999)). Intravenous delivery of cholesterol-containing cationic liposomes has been shown to preferentially target pulmonary tissues (Liu et al., *Nature Biotechnol.* 15:167 (1997)), and effectively mediate transfer and expression of genes in vivo. Other examples of successful targeted in vivo delivery of nucleic acid molecules are known in the art. Finally, a recombinant nucleic acid molecule can be selectively (i.e., preferentially, substantially exclusively) expressed in a target cell by selecting a transcription control sequence, and preferably, a promoter, which is selectively induced in the target cell and remains substantially inactive in non-target cells.

Another aspect of the invention relates to a method of inhibiting sodium absorption through a sodium channel, comprising contacting (e.g., binding) the sodium channel with a PLUNC protein or a functional fragment or homolog thereof. Inhibition of sodium absorption can be measured by any technique known in the art or disclosed herein.

Another aspect of the invention relates to a method of increasing the volume of fluid lining an epithelial mucosal surface, comprising contacting (e.g., binding) a sodium channel present on the epithelial mucosal surface with a PLUNC protein or a functional fragment or homolog thereof. The volume of fluid lining an epithelial mucosal surface can be measured by any technique known in the art or disclosed herein.

A further aspect of the invention relates to a method of reducing the level of a sodium channel present on the surface of a cell, comprising contacting (e.g., binding) the sodium channel with a PLUNC protein or a functional fragment or homolog thereof.

An additional aspect of the invention relates to a method of treating a disorder responsive to inhibition of sodium absorption across an epithelial mucosal surface in a subject in need thereof, comprising delivering to the subject a therapeutically effective amount of a PLUNC protein or a functional fragment or homolog thereof. The disorder can be, for example, a lung disorder (e.g., a disorder associated with mucus clearance, cystic fibrosis, chronic obstructive pulmonary disease, acute or chronic bronchitis, or asthma), a gastrointestinal disorder (e.g., inflammatory bowel disease), a kidney disorder, or a cardiovascular disorder.

Another aspect of the invention relates to a method of regulating salt balance, blood volume, blood pressure (e.g., by inducing natriuresis), and/or colonic motility in a subject in need thereof, comprising delivering to the subject a therapeutically effective amount of a PLUNC protein or a functional fragment or homolog thereof.

III. Increasing Sodium Channel Activation

A different aspect of the invention relates to methods of preventing the binding of a PLUNC protein to a sodium channel, thereby allowing activation of the sodium channel and increasing the flow of sodium ions. Thus, one aspect of the invention relates to a method of increasing the activation of a sodium channel, comprising inhibiting the binding of a PLUNC protein to the sodium channel. In one embodiment, the sodium channel is an epithelial sodium channel (ENaC), e.g., human ENaC. In another embodiment, the sodium channel is one that is similar in sequence and/or structure to ENaC. In another embodiment, inhibiting the binding of a PLUNC protein increases cleavage of the sodium channel by a protease, thereby leading to activation of the channel. The binding of a PLUNC protein to the sodium channel can be measured by any method known in the art or as disclosed herein. The activation of the sodium channel can be at least about 20%, e.g., at least about 30%, 40%, 50%, 60%, 70%, 80%, 90%, or 100% relative to sodium channel activation in the absence of inhibition of binding.

The PLUNC protein can be any protein from the PLUNC family that can bind to and inhibit the activation of sodium channel. In one embodiment, the PLUNC protein is a human PLUNC protein, as well as functional fragments and homologs thereof. In another embodiment, the PLUNC protein is SPLUNC1 or SPLUNC2.

The method of inhibiting the activation of a sodium channel can be carried out, e.g., on an isolated sodium channel, a sodium channel in an artificial membrane, or a sodium channel in a cell. In one embodiment, the sodium channel is present in an isolated cell, e.g., a cultured primary cell or cell line. In another embodiment, the isolated cell is part of an epithelial cell culture, e.g., a natural or artificial epithelial lining, e.g., a cell culture in a device (such as an Ussing chamber) in which characteristics such as ion flow and/or potential can be measured across lining or an isolated tissue or tissue culture. In a further embodiment, the cell can be present in an animal, e.g., an animal that is a disease model or a subject in need of treatment.

In one embodiment, inhibiting the binding of a PLUNC protein comprises delivering a PLUNC protein inhibitor to the PLUNC protein. The PLUNC protein inhibitor can be any compound or molecule that inhibits the ability of PLUNC to bind to a sodium channel or in any other manner inhibits the activation of the sodium channel. In one embodiment, the PLUNC protein inhibitor is an antibody that specifically recognizes the PLUNC protein, e.g., the active site of the PLUNC protein.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep, camel, or human, or can be a chimeric antibody. See, e.g., Walker et al., *Molec. Immunol.* 26:403 (1989). The antibodies can be recombinant monoclonal antibodies produced according to the methods disclosed in U.S. Pat. No. 4,474,893 or U.S. Pat. No. 4,816, 567. The antibodies can also be chemically constructed according to the method disclosed in U.S. Pat. No. 4,676,980.

Antibody fragments included within the scope of the present invention include, for example, Fab, Fab', F(ab')$_2$, and Fv fragments; diabodies; linear antibodies; single-chain antibody molecules; and multispecific antibodies formed from antibody fragments. Such fragments can be produced by known techniques. For example, F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse et al., *Science* 254:1275 (1989)).

Antibodies of the invention may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature* 321:522 (1986); Riechmann et al., *Nature,* 332:323 (1988); and Presta, *Curr. Op. Struct. Biol.* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature* 321:522 (1986); Riechmann et al., *Nature* 332:323 (1988); Verhoeyen et al., *Science* 239: 1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., *J. Immunol.* 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., *Bio/Technology* 10:779 (1992); Lonberg et al., *Nature* 368:856 (1994); Morrison, *Nature* 368:812 (1994); Fishwild et al., *Nature Biotechnol* 14:845 (1996); Neuberger, *Nature Biotechnol* 14:826 (1996); Lonberg and Huszar, *Intern. Rev. Immunol.* 13:65 (1995).

Polyclonal antibodies used to carry out the present invention can be produced by immunizing a suitable animal (e.g., rabbit, goat, etc.) with an antigen to which a monoclonal antibody to the target binds, collecting immune serum from the animal, and separating the polyclonal antibodies from the immune serum, in accordance with known procedures.

Monoclonal antibodies used to carry out the present invention can be produced in a hybridoma cell line according to the technique of Kohler and Milstein, *Nature* 265:495 (1975). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., Huse, *Science* 246:1275 (1989).

Antibodies specific to the target polypeptide can also be obtained by phage display techniques known in the art.

Various immunoassays can be used for screening to identify antibodies having the desired specificity for the polypeptides of this invention. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes on the polypeptides or peptides of this invention can be used as well as a competitive binding assay.

Antibodies can be conjugated to a solid support (e.g., beads, plates, slides or wells formed from materials such as latex or polystyrene) in accordance with known techniques. Antibodies can likewise be conjugated to detectable groups such as radiolabels (e.g., $^{35}$S, $^{125}$I, $^{131}$I), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

In one embodiment, the PLUNC protein inhibitor is an aptamer that specifically recognizes the PLUNC protein, e.g., the active site of the PLUNC protein. Recently, small structured single-stranded RNAs, also known as RNA aptamers, have emerged as viable alternatives to small-molecule and antibody-based therapy (Que-Gewirth et al., *Gene Ther.* 14:283 (2007); Ireson et al., *Mol. Cancer Ther.* 5:2957 (2006)). RNA aptamers specifically bind target proteins with high affinity, are quite stable, lack immunogenicity, and elicit biological responses. Aptamers are evolved by means of an iterative selection method called SELEX (systematic evolution of ligands by exponential enrichment) to specifically recognize and tightly bind their targets by means of well-defined complementary three-dimensional structures.

RNA aptamers represent a unique emerging class of therapeutic agents (Que-Gewirth et al., *Gene Ther.* 14:283 (2007); Ireson et al., *Mol. Cancer Ther.* 5:2957 (2006)). They are relatively short (12-30 nucleotide) single-stranded RNA oligonucleotides that assume a stable three-dimensional shape to tightly and specifically bind selected protein targets to elicit a biological response. In contrast to antisense oligonucleotides, RNA aptamers can effectively target extracellular targets. Like antibodies, aptamers possess binding affinities in the low nanomolar to picomolar range. In addition, aptamers are heat stable, lack immunogenicity, and possess minimal interbatch variability. Chemical modifications, such as amino or fluoro substitutions at the 2' position of pyrimidines, may reduce degradation by nucleases. The biodistribution and clearance of aptamers can also be altered by chemical addition of moieties such as polyethylene glycol and cholesterol. Further, SELEX allows selection from libraries consisting of up to $10^{15}$ ligands to generate high-affinity oligonucleotide ligands to purified biochemical targets.

In another embodiment, the PLUNC protein inhibitor is a nucleic acid-based inhibitor, e.g., a siRNA, antisense oligonucleotide, ribozyme, etc.

The term "antisense nucleotide sequence" or "antisense oligonucleotide" as used herein, refers to a nucleotide sequence that is complementary to a specified DNA or RNA sequence. Antisense oligonucleotides and nucleic acids that express the same can be made in accordance with conventional techniques. See, e.g., U.S. Pat. No. 5,023,243 to Tullis; U.S. Pat. No. 5,149,797 to Pederson et al. The antisense nucleotide sequence can be complementary to the entire nucleotide sequence encoding the polypeptide or a portion thereof of at least 10, 20, 40, 50, 75, 100, 150, 200, 300, or 500 contiguous bases and will reduce the level of polypeptide production.

Those skilled in the art will appreciate that it is not necessary that the antisense nucleotide sequence be fully complementary to the target sequence as long as the degree of sequence similarity is sufficient for the antisense nucleotide sequence to hybridize to its target and reduce production of the polypeptide. As is known in the art, a higher degree of sequence similarity is generally required for short antisense nucleotide sequences, whereas a greater degree of mismatched bases will be tolerated by longer antisense nucleotide sequences.

For example, hybridization of such nucleotide sequences can be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and/or conditions represented by a wash stringency of 50% formamide with 5×Denhardt's solution, 0.5% SDS and 1×SSPE at 42° C., respectively) to the nucleotide sequences specifically disclosed herein. See, e.g., Sambrook et al., *Molecular Cloning: A Laboratory Manual* 2nd Ed. (Cold Spring Harbor, N.Y., 1989).

In other embodiments, antisense nucleotide sequences of the invention have at least about 70%, 80%, 90%, 95%, 97%, 98% or higher sequence similarity with the complement of the coding sequences specifically disclosed herein and will reduce the level of polypeptide production.

The length of the antisense nucleotide sequence (i.e., the number of nucleotides therein) is not critical as long as it binds selectively to the intended location and reduces transcription and/or translation of the target sequence, and can be determined in accordance with routine procedures. In general, the antisense nucleotide sequence will be from about eight, ten or twelve nucleotides in length up to about 20, 30, 50, 75 or 100 nucleotides, or longer, in length.

An antisense nucleotide sequence can be constructed using chemical synthesis and enzymatic ligation reactions by procedures known in the art. For example, an antisense nucleotide sequence can be chemically synthesized using naturally occurring nucleotides or various modified nucleotides designed to increase the biological stability of the molecules or to increase the physical stability of the duplex formed between the antisense and sense nucleotide sequences, e.g., phosphorothioate derivatives and acridine substituted nucleotides can be used. Examples of modified nucleotides which can be used to generate the antisense nucleotide sequence include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleotide sequence can be produced using an expression vector into which a nucleic acid has been cloned in an antisense orientation (i.e., RNA transcribed from the inserted nucleic acid will be of an antisense orientation to a target nucleic acid of interest).

The antisense nucleotide sequences of the invention further include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described. In another non-limiting example, the antisense nucleotide sequence is a nucleotide sequence in which one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. See also, Furdon et al., Nucleic Acids Res. 17:9193 (1989); Agrawal et al., Proc. Natl. Acad. Sci. USA 87:1401 (1990); Baker et al., Nucleic Acids Res. 18:3537 (1990); Sproat et al., Nucleic Acids Res. 17:3373 (1989); Walder and Walder, Proc. Natl. Acad. Sci. USA 85:5011 (1988); incorporated by reference herein in their entireties for their teaching of methods of making antisense molecules, including those containing modified nucleotide bases).

Triple helix base-pairing methods can also be employed to inhibit PLUNC proteins. Triple helix pairing is believed to work by inhibiting the ability of the double helix to open sufficiently for the binding of polymerases, transcription factors, or regulatory molecules. Recent therapeutic advances using triplex DNA have been described in the literature (e.g., Gee et al., (1994) In: Huber et al., Molecular and Immunologic Approaches, Futura Publishing Co., Mt. Kisco, N.Y.).

Small Interference (si) RNA, also known as RNA interference (RNAi) molecules, provides another approach for modulating the expression of PLUNC proteins. siRNA is a mechanism of post-transcriptional gene silencing in which double-stranded RNA (dsRNA) corresponding to a coding sequence of interest is introduced into a cell or an organism, resulting in degradation of the corresponding mRNA. The mechanism by which siRNA achieves gene silencing has been reviewed in Sharp et al., Genes Dev. 15:485 (2001); and Hammond et al., Nature Rev. Gen, 2:110 (2001)). The siRNA effect persists for multiple cell divisions before gene expression is regained. siRNA is therefore a powerful method for making targeted knockouts or "knockdowns" at the RNA level. siRNA has proven successful in human cells, including human embryonic kidney and HeLa cells (see, e.g., Elbashir et al., Nature 411:494 (2001)). In one embodiment, silencing can be induced in mammalian cells by enforcing endogenous expression of RNA hairpins (see Paddison et al., Proc. Natl. Acad. Sci. USA 99:1443 (2002)). In another embodiment, transfection of small (21-23 nt) dsRNA specifically inhibits nucleic acid expression (reviewed in Caplen, Trends Biotechnol. 20:49 (2002)).

siRNA technology utilizes standard molecular biology methods. dsRNA corresponding to all or a part of a target coding sequence to be inactivated can be produced by standard methods, e.g., by simultaneous transcription of both strands of a template DNA (corresponding to the target sequence) with T7 RNA polymerase. Kits for production of dsRNA for use in siRNA are available commercially, e.g., from New England Biolabs, Inc. Methods of transfection of dsRNA or plasmids engineered to make dsRNA are routine in the art.

MicroRNA (miRNA), single stranded RNA molecules of about 21-23 nucleotides in length, can be used in a similar fashion to siRNA to modulate gene expression (see U.S. Pat. No. 7,217,807).

Silencing effects similar to those produced by siRNA have been reported in mammalian cells with transfection of a mRNA-cDNA hybrid construct (Lin et al., Biochem. Biophys. Res. Commun. 281:639 (2001)), providing yet another strategy for silencing a coding sequence of interest.

The expression of PLUNC proteins can also be inhibited using ribozymes. Ribozymes are RNA molecules that cleave nucleic acids in a site-specific fashion. Ribozymes have specific catalytic domains that possess endonuclease activity (Kim et al., Proc. Natl. Acad. Sci. USA 84:8788 (1987); Gerlach et al., Nature 328:802 (1987); Forster and Symons, Cell 49:211 (1987)). For example, a large number of ribozymes accelerate phosphoester transfer reactions with a high degree of specificity, often cleaving only one of several phosphoesters in an oligonucleotide substrate (Michel and Westhof, J. Mol. Biol. 216:585 (1990); Reinhold-Hurek and Shub, Nature 357:173 (1992)). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, Nature 338:217 (1989)). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., Proc. Natl. Acad. Sci. USA 88:10591 (1991); Sarver et al., Science 247: 1222 (1990); Sioud et al., J. Mol. Biol. 223:831 (1992)).

In another embodiment, the PLUNC protein inhibitor is a mimetic (e.g., a peptidomimetic) of the sodium channel binding site recognized by a PLUNC protein. The term "mimetic" refers to a compound that has at least 50% of at least one biological activity of a PLUNC protein (e.g., sodium channel binding), e.g., at least 60%, 70%, 80%, or 90% of the biological activity. The term "mimetic" as used herein is intended to be interpreted broadly and encompasses organic and inorganic molecules. Organic compounds include, but are not limited to, small molecules, polypeptides, lipids, carbohydrates, coenzymes, aptamers, and nucleic acid molecules (e.g., gene delivery vectors, antisense oligonucleotides, siRNA, all as described above). The mimetic can further be a compound that is identified by any of the screening methods described below.

Peptidomimetic compounds are designed based upon the amino acid sequences of the functional polypeptide fragments. Peptidomimetic compounds are synthetic compounds having a three-dimensional conformation (i.e., a "peptide motif") that is substantially the same as the three-dimensional conformation of a selected-peptide. The peptide motif provides the peptidomimetic compound with the ability to enhance angiogenesis in a manner qualitatively identical to that of the functional fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbon A, dimethylene and ketomethylene bonds, are known in the art to be generally useful substitutes for peptide bonds in the construction of protease-resistant peptidomimetics.

Another aspect of the invention relates to a method of increasing sodium absorption through a sodium channel, comprising inhibiting the binding of a PLUNC protein to the sodium channel, thereby activating the sodium channel.

An additional aspect of the invention relates to a method of decreasing the volume of fluid lining an epithelial mucosal surface, comprising inhibiting the binding of a PLUNC protein to a sodium channel present in the epithelial mucosal surface, thereby activating the sodium channel.

A further aspect of the invention relates to a method of increasing the level of a sodium channel present on the surface of a cell, comprising inhibiting the binding of a PLUNC protein to the sodium channel present on the surface of the cell.

Another aspect of the invention relates to a method of treating a disorder responsive to activation of sodium absorption in a subject in need thereof, comprising inhibiting the activity of a PLUNC protein in the subject. In one embodiment, the disorder is a lung disorder (e.g., pulmonary edema), a gastrointestinal disorder, a kidney disorder, or a cardiovascular disorder.

A further aspect of the invention relates to a method of regulating salt balance, blood volume, blood pressure, and/or colonic motility in a subject in need thereof, comprising inhibiting the activity of a PLUNC protein in the subject.

An additional aspect of the invention relates to a method of enhancing the sense of taste in a subject, comprising inhibiting the activity of a PLUNC protein in the subject.

IV. Polypeptides, Polynucleotides, and Mimetics

A third aspect of the invention relates to products that can be used to carry out the methods disclosed herein. Thus, one aspect of the invention relates to a polypeptide consisting essentially of the sodium channel binding domain of a PLUNC protein. The sodium channel binding domain is the minimal fragment of the PLUNC protein required to have substantially the same binding activity to the sodium channel as the full length PLUNC protein. The term "substantially the same binding activity" refers to an activity that is at least about 50% of the binding activity of the full length protein, e.g., at least about 60%, 70%, 80%, or 90% of the binding activity. In one embodiment, the PLUNC protein is a human PLUNC protein. In another embodiment, the PLUNC protein is SPLUNC1 or SPLUNC2. In certain embodiments, the fragment comprises, consists essentially of, or consists of the amino acid sequence starting immediately C-terminal of the signal peptide or starting within 1, 2, 3, 4, or 5 amino acids of the C-terminus of the signal peptide and continuing for about 5, 6, 7, 8, 9, 10, 11, 12, 13, 14, 15, 16, 17, 18, 19, 20, 21, 22, 23, 24, 25, 26, 27, 28, 29, or 30 or more amino acids or any range therein. In one embodiment, the fragment comprises, consists essentially of, or consists of a sequence from about residue 20 to about residue 41 of human SPLUNC1 (SEQ ID NO:1), e.g., about residue 22 to about residue 39, or the corresponding sequence (e.g., the approximately 20 amino acids immediately after the signal peptide) from another PLUNC protein. In other embodiments, the fragment comprises, consists essentially of, or consists of a sequence starting from amino acid 20, 21, 22, 23, 24, 25, 26, 27, 28, 29, or and ending with amino acid 35, 36, 37, 38, 39, 40, 41, 42, 43, 44, or 45 of SEQ ID NO:1. In one embodiment, the sodium channel is ENaC, e.g., human ENaC. In another embodiment, the sodium channel is one that is similar in sequence and/or structure to ENaC.

In one embodiment, the functional fragment comprises, consists essentially of, or consists of the amino acid sequence GGLPVPLDQTLPLNVNPA (SEQ ID NO:11), corresponding to amino acids 22-39 of human SPLUNC1, or an amino acid sequence that has at least 70% sequence identity thereto, e.g., at least 75%, 80%, 85%, 90%, 95%, 96%, 97%, 98%, or 99% sequence identity thereto. In another embodiment, the functional fragment comprises, consists essentially of or consists of the partial amino acid sequence LPVPLDQT (SEQ ID NO:14). Each of these amino acid residues has been shown to be important for ENaC inhibitory activity.

In another aspect, the invention relates to a PLUNC protein in which the wild-type amino acid sequence has been modified (e.g., with insertions, deletions, substitutions, or any combination thereof). In certain embodiments, the modified PLUNC protein exhibits a modulation of one or more bioactivity of the PLUNC protein, e.g., a decrease in pH sensitivity. In other embodiments, no more than 20 amino acids of the naturally occurring PLUNC sequence are modified (inserted, deleted or substituted), e.g., no more than 15, 10, 9, 8, 7, 6, or 5 amino acids.

In certain embodiments, the PLUNC protein of the present invention comprises a modified amino acid sequence that reduces or eliminates the inactivation of PLUNC proteins at acidic pHs. In one embodiment, a pH sensitive hinge region is modified to prevent a conformational change of the PLUNC protein at acidic pHs. In one embodiment, one or more amino acids in the hinge region is substituted, e.g., with alanine. In another embodiment, all of the amino acids in the hinge region are substituted, e.g., with alanine. In particular embodiments, the pH sensitive hinge region comprises, consists essentially of, or consists of amino acid residues K94, N103, N104, K138, Q140, N142, and D193 of SEQ ID NO:1 and any one or more of these residues can be modified. In certain embodiments, 1, 2, 3, 4, 5, 6, or 7 of these residues are substituted with another amino acid, e.g., alanine.

A further aspect of the invention relates to a polynucleotide encoding a polypeptide consisting essentially of the sodium channel binding domain of a PLUNC protein. Another aspect of the invention relates to a polynucleotide encoding a modified PLUNC protein of the invention.

Another aspect of the invention relates to a vector comprising the polynucleotide of the invention.

An additional aspect of the invention relates to a cell comprising the polynucleotide and/or vector of the invention. In one embodiment, the cell is an isolated cell, e.g., a cultured primary cell or cell line. In another embodiment, the isolated cell is part of an epithelial cell culture, e.g., a natural or artificial epithelial lining, e.g., a cell culture in a device (such as an Ussing chamber) in which characteristics such as ion flow and/or potential can be measured across the lining, an isolated tissue, or tissue culture. In a further embodiment, the cell can be present in an animal, e.g., an animal that is a disease model or a subject in need of treatment.

A further aspect of the invention relates to a compound that mimics the sodium channel binding domain of a PLUNC protein and binds to a sodium channel, e.g., binds to β-ENaC, wherein cleavage of the sodium channel by a protease is inhibited when bound to the compound. In one embodiment, the compound is a peptidomimetic. The term "compound" as used herein is intended to be interpreted broadly and encompasses organic and inorganic molecules. Organic compounds include, but are not limited to, small molecules, polypeptides, lipids, carbohydrates, coenzymes, aptamers, and nucleic acid molecules (e.g., gene delivery vectors, antisense oligonucleotides, siRNA, all as described above). The compound can further be a compound that is identified by any of the screening methods described below.

The compounds of the present invention can optionally be delivered in conjunction with other therapeutic agents. The additional therapeutic agents can be delivered concurrently with the compounds of the invention. As used herein, the word "concurrently" means sufficiently close in time to produce a combined effect (that is, concurrently can be simultaneously, or it can be two or more events occurring within a short time period before or after each other).

Another aspect of the invention relates to a polypeptide consisting essentially of a PLUNC protein binding domain of a sodium channel. As used herein, a PLUNC protein binding domain of a sodium channel is the minimal portion of the sodium channel amino acid sequence necessary for binding to a PLUNC protein. In one embodiment, the PLUNC protein binding domain is the extracellular portion of the sodium channel.

A further aspect of the invention relates to a polynucleotide encoding a polypeptide consisting essentially of the PLUNC protein binding domain of a sodium channel.

Another aspect of the invention relates to a vector comprising the polynucleotide of the invention.

An additional aspect of the invention relates to a cell comprising the polynucleotide and/or vector of the invention. In one embodiment, the cell is an isolated cell, e.g., a cultured primary cell or cell line. In another embodiment, the isolated cell is part of an epithelial cell culture, e.g., a natural or artificial epithelial lining, e.g., a cell culture in a device (such as an Ussing chamber) in which characteristics such as ion flow and/or potential can be measured across the lining. In a further embodiment, the cell can be present in an animal, e.g., an animal that is a disease model or a subject in need of treatment.

A further aspect of the invention relates to a compound that mimics the PLUNC protein binding domain of a sodium channel and binds to a PLUNC protein, wherein binding of PLUNC protein to the sodium channel is inhibited when bound to the compound. In one embodiment, the compound is a peptidomimetic.

Another aspect of the invention relates to a kit comprising the polypeptide, polynucleotide, vector, cell, peptidomimetic, or compound of the invention and useful for carrying out the methods of the invention. The kit may further comprise additional reagents for carrying out the methods (e.g., buffers, containers) as well as instructions.

V. Diagnosis and Monitoring of Disorders Responsive to Modulation of Sodium Absorption The identification of the interaction between PLUNC proteins and sodium channels provides targets to be used for detection and diagnosis of disorders responsive to modulation of sodium absorption.

One aspect of the invention relates to methods of detecting disorders responsive to modulation of sodium absorption in a subject, comprising obtaining a sample from the subject and determining the expression and/or activity of one or more PLUNC proteins or a functional fragment thereof in the sample, wherein an increase or decrease in expression and/or activity relative to the level of expression and/or activity in a control sample is indicative of a disorder responsive to modulation of sodium absorption and that can be treated by modulation of PLUNC proteins. In one embodiment, the sample is from a diseased tissue such as lung, kidney or intestinal tissue. In another embodiment, the tissue is not diseased tissue.

In this aspect, the expression and/or activity of more than one PLUNC protein may be determined, e.g., 2, 3, 4, or more proteins. In one embodiment, said one or more proteins is selected from the group consisting of SPLUNC1 and SPLUNC2. The tissue sample may be obtained by any method known in the art, such as surgery, biopsy, lavage, aspiration, etc. The sample may be a bodily fluid, e.g., blood, serum, plasma, saliva, urine, cerebrospinal fluid, perspiration, etc. The control sample may be from a normal (i.e., non-diseased) portion of the same tissue or cell type in the subject, from a different tissue or cell type in the subject, from a matched individual, or may be a standard derived from the average of measurements taken from a population of subjects.

In one embodiment, determining the expression and/or activity of one or more PLUNC proteins comprises determining the level of a nucleic acid encoding said one or more proteins. Determining the level of a nucleic acid can be carried out by any means known in the art and as described herein, such as Northern blots, dot blots, PCR, RT-PCR, quantitative PCR, sequence analysis, gene microarray analysis, in situ hybridization, and detection of a reporter gene.

In another embodiment, determining the expression and/or activity of one or more PLUNC proteins comprises determining the level of said one or more proteins or a functional fragment thereof. Determining the level of a protein can be carried out by any means known in the art and as described herein, such as Western blots, immunoblots, immunoprecipitation, immunohistochemistry, immunofluorescence, enzyme-linked immunosorbant assays, and radioimmunoassays.

In a further embodiment, determining the expression and/ or activity of one or more PLUNC proteins comprises determining the activity of said one or more polypeptides or a functional fragment thereof. The activity may be any activity associated with the protein, including, without limitation, sodium channel binding activity, inhibition of sodium channel activation, and ability to decrease the number of sodium channels on the surface of a cell.

VI. Screening Assays and Animal Models

The identification of binding and regulatory interactions between PLUNC proteins and sodium channels provides targets that can be used to screen for agents that modulate binding and sodium absorption as well as models for studying the process of sodium channel regulation and fluid regulation in vitro or in animals.

One aspect of the invention relates to methods of identifying a compound that inhibits binding of PLUNC proteins to sodium channels or mimics binding of PLUNC proteins to sodium channels, comprising determining the binding of PLUNC proteins to sodium channels and/or activity of sodium channels in the presence and absence of a test compound, and selecting a compound that increases or decreases the binding of PLUNC proteins to sodium channels and/or activation of sodium channels relative to the level in the absence of the compound.

In this aspect, the assay may be a cell-based or cell-free assay. In one embodiment, the cell may be a primary cell, e.g., an epithelial cell. In another embodiment, the cell is from a cell line, e.g., an epithelial cell line. The cell may be contacted with the compound in vitro (e.g., in a culture dish) or in an animal (e.g., a transgenic animal or an animal model). In one embodiment, the detected increase or decrease in binding and/or activity is statistically significant, e.g., at least p<0.05, e.g., p<0.01, 0.005, or 0.001. In another embodiment, the detected increase or decrease is at least about 10%, 20%, 30%, 40%, 50%, 60&, 70%, 80%, 90%, 100% or more relative to the amount in the absence of the test compound.

Any desired end-point can be detected in a screening assay, e.g., binding to the polypeptide, gene or RNA, modulation of the activity of the polypeptide, modulation of sodium-regulated pathways, and/or interference with binding by a known regulator of a polynucleotide or polypeptide. Methods of detecting the foregoing activities are known in the art and include the methods disclosed herein.

Any compound of interest can be screened according to the present invention. Suitable test compounds include organic and inorganic molecules. Suitable organic molecules can include but are not limited to small molecules (compounds less than about 1000 Daltons), polypeptides (including enzymes, antibodies, and Fab' fragments), carbohydrates, lipids, coenzymes, and nucleic acid molecules (including DNA, RNA, and chimerics and analogs thereof) and nucleotides and nucleotide analogs.

Further, the methods of the invention can be practiced to screen a compound library, e.g., a small molecule library, a combinatorial chemical compound library, a polypeptide library, a cDNA library, a library of antisense nucleic acids, and the like, or an arrayed collection of compounds such as polypeptide and nucleic acid arrays.

In one representative embodiment, the invention provides methods of screening test compounds to identify a test compound that binds to a PLUNC protein or a sodium channel. Compounds that are identified as binding to the protein can be subject to further screening (e.g., for modulation of sodium absorption) using the methods described herein or other suitable techniques.

Also provided are methods of screening compounds to identify those that modulate the activity of a PLUNC protein or sodium channel. The term "modulate" is intended to refer to compounds that enhance (e.g., increase) or inhibit (e.g., reduce) the activity of the protein (or functional fragment). For example, the interaction of the polypeptide or functional fragment with a binding partner can be evaluated. As another alternative, physical methods, such as NMR, can be used to assess biological function. Activity of the PLUNC protein or sodium channel can be evaluated by any method known in the art, including the methods disclosed herein.

Compounds that are identified as modulators of activity can optionally be further screened using the methods described herein (e.g., for binding to the PLUNC protein or sodium channel or functional fragment thereof, polynucleotide or RNA, and the like). The compound can directly interact with the polypeptide or functional fragment, polynucleotide or mRNA and thereby modulate its activity. Alternatively, the compound can interact with any other polypeptide, nucleic acid or other molecule as long as the interaction results in a modulation of the activity of the polypeptide or functional fragment.

The screening assay can be a cell-based or cell-free assay. Further, the PLUNC protein or sodium channel (or functional fragment thereof) or polynucleotide can be free in solution, affixed to a solid support, expressed on a cell surface, or located within a cell.

With respect to cell-free binding assays, test compounds can be synthesized or otherwise affixed to a solid substrate, such as plastic pins, glass slides, plastic wells, and the like. For example, the test compounds can be immobilized utilizing conjugation of biotin and streptavidin by techniques well known in the art. The test compounds are contacted with the polypeptide or functional fragment thereof and washed. Bound polypeptide can be detected using standard techniques in the art (e.g., by radioactive or fluorescence labeling of the polypeptide or functional fragment, by ELISA methods, and the like).

Alternatively, the target can be immobilized to a solid substrate and the test compounds contacted with the bound polypeptide or functional fragment thereof. Identifying those test compounds that bind to and/or modulate the PLUNC protein or sodium channel or functional fragment can be carried out with routine techniques. For example, the test compounds can be immobilized utilizing conjugation of biotin and streptavidin by techniques well known in the art. As another illustrative example, antibodies reactive with the polypeptide or functional fragment can be bound to the wells of the plate, and the polypeptide trapped in the wells by antibody conjugation. Preparations of test compounds can be incubated in the polypeptide (or functional fragment)-presenting wells and the amount of complex trapped in the well can be quantitated.

In another representative embodiment, a fusion protein can be provided which comprises a domain that facilitates binding of the polypeptide to a matrix. For example, glutathione-S-transferase fusion proteins can be adsorbed onto glutathione sepharose beads (Sigma Chemical, St. Louis, Mo.) or glutathione derivatized microtitre plates, which are then combined with cell lysates (e.g., $^{35}$S-labeled) and the test compound, and the mixture incubated under conditions conducive to complex formation (e.g., at physiological conditions for salt and pH). Following incubation, the beads are washed to remove any unbound label, and the matrix immobilized and radiolabel detected directly, or in the supernatant after the complexes are dissociated. Alternatively, the complexes can be dissociated from the matrix, separated by SDS-PAGE, and the level of PLUNC protein or sodium channel or functional fragment thereof found in the bead fraction quantitated from the gel using standard electrophoretic techniques.

Another technique for compound screening provides for high throughput screening of compounds having suitable binding affinity to the polypeptide of interest, as described in published PCT application WO84/03564. In this method, a large number of different small test compounds are synthesized on a solid substrate, such as plastic pins or some other surface. The test compounds are reacted with the PLUNC protein or sodium channel or functional fragment thereof and washed. Bound polypeptide is then detected by methods well known in the art. Purified polypeptide or a functional fragment can also be coated directly onto plates for use in the aforementioned drug screening techniques. Alternatively, non-neutralizing antibodies can be used to capture the peptide and immobilize it on a solid support.

With respect to cell-based assays, any suitable cell can be used, including bacteria, yeast, insect cells (e.g., with a baculovirus expression system), avian cells, mammalian cells, or plant cells. In exemplary embodiments, the assay is carried out in a cell line that naturally expresses the polynucleotide or produces the polypeptide, e.g., epithelial cells. Further, in other embodiments, it is desirable to use nontransformed cells (e.g., primary cells) as transformation may alter the function of the polypeptide.

The screening assay can be used to detect compounds that bind to or modulate the activity of the native PLUNC protein or sodium channel (e.g., polypeptide that is normally produced by the cell). Alternatively, the cell can be modified to express (e.g., overexpress) a recombinant polypeptide or functional fragment thereof. According to this embodiment, the cell can be transiently or stably transformed with a polynucleotide encoding the PLUNC protein or sodium channel or functional fragment, and can be stably transformed, for example, by stable integration into the genome of the organism or by expression from a stably maintained episome (e.g., Epstein Barr Virus derived episomes). In another embodiment, a polynucleotide encoding a reporter molecule can be linked to a regulatory element of the polynucleotide encoding a PLUNC protein or sodium channel and used to identify compounds that modulate expression of the polypeptide.

In a cell-based assay, the compound to be screened can interact directly with the PLUNC protein or sodium channel or functional fragment thereof (i.e., bind to it) and modulate the activity thereof. Alternatively, the compound can be one that modulates polypeptide activity (or the activity of a functional fragment) at the nucleic acid level. To illustrate, the compound can modulate transcription of the gene (or transgene), modulate the accumulation of mRNA (e.g., by affecting the rate of transcription and/or turnover of the mRNA), and/or modulate the rate and/or amount of translation of the mRNA transcript.

As a further type of cell-based binding assay, the PLUNC protein or sodium channel or functional fragment thereof can be used as a "bait protein" in a two-hybrid or three-hybrid assay (see, e.g., U.S. Pat. No. 5,283,317; Zervos et al., *Cell* 72:223 (1993); Madura et al., *J. Biol. Chem.* 268:12046 (1993); Bartel et al., *Biotechniques* 14:920 (1993); Iwabuchi et al., *Oncogene* 8:1693 (1993); and PCT publication WO94/10300), to identify other polypeptides that bind to or interact with the polypeptide of the invention or functional fragment thereof.

The two-hybrid system is based on the modular nature of most transcription factors, which consist of separable DNA-binding and activation domains. Briefly, the assay utilizes two different DNA constructs. In one construct, the polynucleotide that encodes the PLUNC protein or sodium channel or functional fragment thereof is fused to a nucleic acid encoding the DNA binding domain of a known transcription factor (e.g., GAL-4). In the other construct, a DNA sequence, optionally from a library of DNA sequences, that encodes an unidentified protein ("prey" or "sample") is fused to a nucleic acid that codes for the activation domain of the known transcription factor. If the "bait" and the "prey" proteins are able to interact in vivo, forming a complex, the DNA-binding and activation domains of the transcription factor are brought into close proximity. This proximity allows transcription of a reporter sequence (e.g., LacZ), which is operably linked to a transcriptional regulatory site responsive to the transcription factor. Expression of the reporter can be detected and cell colonies containing the functional transcription factor can be isolated and used to obtain the nucleic acid encoding the polypeptide that exhibited binding to the PLUNC protein or sodium channel or functional fragment.

Screening assays can also be carried out in vivo in animals. Thus, as still a further aspect, the invention provides a transgenic non-human animal comprising an isolated polynucleotide encoding a PLUNC protein or sodium channel or functional fragment thereof, which can be produced according to methods well-known in the art. The transgenic non-human animal can be from any species, including avians and non-human mammals. According to this aspect of the invention, suitable non-human mammals include mice, rats, rabbits, guinea pigs, goats, sheep, pigs, and cattle. Suitable avians include chickens, ducks, geese, quail, turkeys, and pheasants.

The polynucleotide encoding the polypeptide or functional fragment can be stably incorporated into cells within the transgenic animal (typically, by stable integration into the genome or by stably maintained episomal constructs). It is not necessary that every cell contain the transgene, and the animal can be a chimera of modified and unmodified cells, as long as a sufficient number of cells comprise and express the polynucleotide encoding the polypeptide or functional fragment so that the animal is a useful screening tool.

Exemplary methods of using the transgenic non-human animals of the invention for in vivo screening of compounds that modulate sodium regulation, and/or the activity of a PLUNC protein or sodium channel comprise administering a test compound to a transgenic non-human animal (e.g., a mammal such as a mouse) comprising an isolated polynucleotide encoding a PLUNC protein or sodium channel or functional fragment thereof stably incorporated into the genome and detecting whether the test compound modulates sodium regulation and/or polypeptide activity (or the activity of a functional fragment). It is known in the art how to measure these responses in vivo.

Methods of making transgenic animals are known in the art. DNA or RNA constructs can be introduced into the germ line of an avian or mammal to make a transgenic animal. For example, one or several copies of the construct can be incorporated into the genome of an embryo by standard transgenic techniques.

In an exemplary embodiment, a transgenic non-human animal is produced by introducing a transgene into the germ line of the non-human animal. Transgenes can be introduced into embryonal target cells at various developmental stages. Different methods are used depending on the stage of development of the embryonal target cell. The specific line(s) of any animal used should, if possible, be selected for general good health, good embryo yields, good pronuclear visibility in the embryo, and good reproductive fitness.

Introduction of the transgene into the embryo can be accomplished by any of a variety of means known in the art such as microinjection, electroporation, lipofection, or a viral vector. For example, the transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg can be incubated in vitro for varying amounts of time, or reimplanted into the surrogate host, or both. One common method is to incubate the embryos in vitro for about 1-7 days, depending on the species, and then reimplant them into the surrogate host.

The progeny of the transgenically manipulated embryos can be tested for the presence of the construct by Southern blot analysis of a segment of tissue. An embryo having one or more copies of the exogenous cloned construct stably integrated into the genome can be used to establish a permanent transgenic animal line.

Transgenically altered animals can be assayed after birth for the incorporation of the construct into the genome of the offspring. This can be done by hybridizing a probe corresponding to the polynucleotide sequence coding for the polypeptide or a segment thereof onto chromosomal material from the progeny. Those progeny found to contain at least one copy of the construct in their genome are grown to maturity.

Methods of producing transgenic avians are also known in the art, see, e.g., U.S. Pat. No. 5,162,215.

In particular embodiments, to create an animal model in which the activity or expression of a PLUNC protein or sodium channel is decreased, it is desirable to inactivate, replace or knock-out the endogenous gene encoding the polypeptide by homologous recombination with a transgene using embryonic stem cells. In this context, a transgene is meant to refer to heterologous nucleic acid that upon insertion within or adjacent to the gene results in a decrease or inactivation of gene expression or polypeptide amount or activity.

A knock-out of a gene means an alteration in the sequence of a gene that results in a decrease of function of the gene, preferably such that the gene expression or polypeptide amount or activity is undetectable or insignificant. Knockouts as used herein also include conditional knock-outs, where alteration of the gene can occur upon, for example, exposure of the animal to a substance that promotes gene alteration (e.g., tetracycline or ecdysone), introduction of an enzyme that promotes recombination at a gene site (e.g., Cre in the Cre-lox system), or other method for directing the gene alteration postnatally. Knock-out animals may be prepared using methods known to those of skill in the art. See, for example, Hogan, et al. (1986) Manipulating the Mouse Embryo: A Laboratory Manual, Cold Spring Harbor Laboratory Press, Cold Spring Harbor, N.Y.

A knock-out construct is a nucleic acid sequence, such as a DNA or RNA construct, which, when introduced into a cell, results in suppression (partial or complete) of expression of a polypeptide encoded by endogenous DNA in the cell. A knock-out construct as used herein may include a construct containing a first fragment from the 5' end of the gene encoding a PLUNC protein or sodium channel, a second fragment from the 3' end of the gene and a DNA fragment encoding a selectable marker positioned between the first and second fragments. It should be understood by the skilled artisan that any suitable 5' and 3' fragments of a gene may be used as long as the expression of the corresponding gene is partially or completely suppressed by insertion of the transgene. Suitable selectable markers include, but are not limited to, neomycin, puromycin and hygromycin. In addition, the construct may contain a marker, such as diphtheria toxin A or thymidine kinase, for increasing the frequency of obtaining correctly targeted cells. Suitable vectors include, but are not limited to, pBLUESCRIPT, pBR322, and pGEM7.

Alternatively, a knock-out construct may contain RNA molecules such as antisense RNA, siRNA, and the like to decrease the expression of a gene encoding a PLUNC protein or sodium channel. Typically, for stable expression the RNA molecule is placed under the control of a promoter. The promoter may be regulated, if deficiencies in the protein of interest may lead to a lethal phenotype, or the promoter may drive constitutive expression of the RNA molecule such that the gene of interest is silenced under all conditions of growth. While homologous recombination between the knock-out construct and the gene of interest may not be necessary when using an RNA molecule to decrease gene expression, it may be advantageous to target the knock-out construct to a particular location in the genome of the host organism so that unintended phenotypes are not generated by random insertion of the knock-out construct.

The knock-out construct may subsequently be incorporated into a viral or nonviral vector for delivery to the host animal or may be introduced into embryonic stem (ES) cells. ES cells are typically selected for their ability to integrate into and become part of the germ line of a developing embryo so as to create germ line transmission of the knock-out construct. Thus, any ES cell line that can do so is suitable for use herein. Suitable cell lines which may be used include, but are not limited to, the 129J ES cell line or the J1 ES cell line. The cells are cultured and prepared for DNA insertion using methods well-known to the skilled artisan (e.g., see Robertson (1987) In: Teratocarcinomas and Embryonic Stem Cells: A Practical Approach, E. J. Robertson, ed. IRL Press, Washington, D.C.; Bradley et al., Curr. Topics Develop. Biol. 20:357 (1986); Hogan et al., (1986) Manipulating the Mouse Embryo: A Laboratory Manual, Cold Spring Harbor Laboratory Press, Cold Spring Harbor, N.Y.).

Insertion of the knock-out construct into the ES cells may be accomplished using a variety of methods well-known in the art, including, for example, electroporation, microinjection, and calcium phosphate treatment. For insertion of the DNA or RNA sequence, the knock-out construct nucleic acids are added to the ES cells under appropriate conditions for the insertion method chosen. If the cells are to be electroporated, the ES cells and construct nucleic acids are exposed to an electric pulse using an electroporation machine (electroporator) and following the manufacturer's guidelines for use. After electroporation, the cells are allowed to recover under suitable incubation conditions. The cells are then screened for the presence of the knockout construct.

Each knock-out construct to be introduced into the cell is first typically linearized if the knock-out construct has been inserted into a vector. Linearization is accomplished by digesting the knock-out construct with a suitable restriction endonuclease selected to cut only within the vector sequence and not within the knock-out construct sequence.

Screening for cells which contain the knock-out construct (homologous recombinants) may be done using a variety of methods. For example, as described herein, cells can be processed as needed to render DNA in them available for hybridization with a nucleic acid probe designed to hybridize only to cells containing the construct. For example, cellular DNA can be probed with $^{32}$P-labeled DNA which locates outside the targeting fragment. This technique can be used to identify those cells with proper integration of the knock-out construct. The DNA can be extracted from the cells using standard methods (e.g., see, Sambrook et al., Molecular Cloning: A Laboratory Manual 2nd Ed. (Cold Spring Harbor, N.Y., 1989)). The DNA may then be analyzed by Southern blot with a probe or probes designed to hybridize in a specific pattern to genomic DNA digested with one or more particular restriction enzymes.

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3-4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2-3 days pseudopregnant females are appropriate.

Germline transmission of the knockout construct may be determined using standard methods. Offspring resulting from implantation of embryos containing the ES cells described above are screened for the presence of the desired alteration (e.g., knock-out of the PLUNC protein). This may be done, for example, by obtaining DNA from offspring (e.g., tail DNA) to assess for the knock-out construct, using known methods (e.g., Southern analysis, dot blot analysis, PCR analysis). See, for example, Sambrook et al., Molecular Cloning: A Laboratory Manual 2nd Ed. (Cold Spring Harbor, N.Y., 1989). Offspring identified as chimeras may be crossed with one another to produce homozygous knock-out animals.

Mice are often used as animal models because they are easy to house, relatively inexpensive, and easy to breed. However, other knock-out animals may also be made in accordance with the present invention such as, but not limited to, monkeys, cattle, sheep, pigs, goats, horses, dogs, cats, guinea pigs, rabbits and rats. Accordingly, appropriate vectors and promoters well-known in the art may be selected and used to generate a transgenic animal deficient in expression of a PLUNC protein or sodium channel.

In another embodiment, animal models may be created using animals that are not transgenic.

VII. Pharmaceutical Compositions

As a further aspect, the invention provides pharmaceutical formulations and methods of administering the same to achieve any of the therapeutic effects (e.g., modulation of sodium absorption) discussed above. The pharmaceutical formulation may comprise any of the reagents discussed above in a pharmaceutically acceptable carrier, e.g., a polynucleotide encoding a PLUNC protein or sodium channel or a fragment thereof, a PLUNC protein or sodium channel or fragment thereof, an antibody against a PLUNC protein, an antisense oligonucleotide, an siRNA molecule, a ribozyme, an aptamer, a peptidomimetic, a small molecule, or any other compound that modulates the activity of a PLUNC protein or sodium channel, including compounds identified by the screening methods described herein.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The compounds of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the compound (including the physiologically acceptable salts thereof) is typically admixed with, inter alia, an acceptable carrier. The carrier can be a solid or a liquid, or both, and is preferably formulated with the compound as a unit-dose formulation, for example, a tablet, which can contain from 0.01 or 0.5% to 95% or 99% by weight of the compound. One or more compounds can be incorporated in the formulations of the invention, which can be prepared by any of the well-known techniques of pharmacy.

A further aspect of the invention is a method of treating subjects in vivo, comprising administering to a subject a pharmaceutical composition comprising a compound of the invention in a pharmaceutically acceptable carrier, wherein the pharmaceutical composition is administered in a therapeutically effective amount. Administration of the compounds of the present invention to a human subject or an animal in need thereof can be by any means known in the art for administering compounds.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). The most suitable route in any given case will depend on the nature and severity of the condition being treated and on the nature of the particular compound which is being used.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the compound. Suitable formulations comprise citrate or bis\tris buffer (pH 6) or ethanol/water and contain from 0.1 to 0.2M of the compound.

The compound can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharinacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the compound in a local rather than systemic manner, for example, in a depot or sustained-release formulation.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the compounds disclosed herein or salts thereof, can be lyophilized to produce a lyophilizate which can be reconstituted with a pharmaceutically acceptable carrier, such as water, to regenerate a liposomal suspension.

In the case of water-insoluble compounds, a pharmaceutical composition can be prepared containing the water-insoluble compound, such as for example, in an aqueous base emulsion. In such an instance, the composition will contain a sufficient amount of pharmaceutically acceptable emulsifying agent to emulsify the desired amount of the compound. Particularly useful emulsifying agents include phosphatidyl cholines and lecithin.

In particular embodiments, the compound is administered to the subject in a therapeutically effective amount, as that term is defined above. Dosages of pharmaceutically active compounds can be determined by methods known in the art, see, e.g., *Remington's Pharmaceutical Sciences* (Maack Publishing Co., Easton, Pa.). The therapeutically effective dosage of any specific compound will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the compound, including the cases where a salt is employed. Toxicity concerns at the higher level can restrict intravenous dosages to a lower level such as up to about 10 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 µmol/kg to 50 µmol/kg, and more particularly to about 22 µmol/kg and to 33 µmol/kg of the compound for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults.

The present invention is more particularly described in the following examples that are intended as illustrative only since numerous modifications and variations therein will be apparent to those skilled in the art.

EXAMPLE 1

Experimental Methods

Tissue procurement and cell culture: Cells were harvested by enzymatic digestion from human bronchial tissue as previously described under a protocol approved by the UNC School of Medicine IRB (Tarran et al., *J. Gen. Physiol.* 127: 591 (2006)). Human excess donor lungs and excised recipient lungs were obtained at the time of lung transplantation from portions of main stem or lumbar bronchi and cells were harvested by enzymatic digestion. All preparations were maintained at an air-liquid interface in a modified bronchial epithelial medium and used 2-5 weeks after seeding on 12 mm T-Clear inserts (Corning Costar) coated with human placental type VI collagen (Sigma). Phosphate buffered saline (PBS) was used for washing human bronchial epithelial culture mucosal surfaces. HBECs were maintained at an air-liquid interface in a modified bronchial epithelial growth medium (BEGM) with 5% $CO_2$ at 37° C. and used 2-5 weeks after seeding on 12-mm T-clear inserts (Corning-Costar, Corning, N.Y., USA) (Randell, *Methods Mol. Biol.* 742:285 (2011)).

HEK293T cells were cultured in DMEM/F12 medium containing 10% FBS, 1× penicillin/streptomycin, 0.2 µg/mL puromycin, and 0.1 mM hygromycin at 37° C./5% $CO_2$ on 6-well plastic plates. Cells were transfected according to the manufacturer's instructions using Lipofectamine 2000 (Invitrogen, Carlsbad, Calif., USA). Cells were transfected when 90-95% confluent with 0.5 µg of plasmid DNA per construct per well and incubated at 37° C./5% $CO_2$ overnight. CHO cell lines stably expressing human ASIC1a, human ASIC2a and rat ASIC3 were used in the electrophysiological measurements of ASICs (Poirot, *J. Biol. Chem.* 279: 38448 (2004)).

Identification of SPLUNC1:

Airway surface liquid was collected by lavaging human bronchial epithelial cultures with 100 µl PBS at 37° C. for 15 min. The lavage was then centrifuged for 5 min at 4000 rpm to remove dead cells and the supernatants were incubated overnight on an end-over-end rotator at 4° C. with trypsin-agarose beads (Sigma)±aprotinin (Sigma). The beads were eluted using 30 µl Laemmli buffer, boiled at 95° C. for 5 min, separated on a 15% sodium dodecyl sulfate polyacrylamide gel electrophoresis (SDS PAGE) gel per the University of North Carolina—Duke Michael Hooker Proteomics Center standard procedures (proteomics.unc.edu/protocol.shtml). Visible bands were excised and prepared for mass spectrometry analysis by MALDI-MS/MS as described previously (Loiselle et al., *J. Proteome Res.* 4:992 (2005)).

Peptides:

Peptides were synthesized and purified by the UNC Microprotein Sequencing and Peptide Synthesis Facility. The sequence of the G22-A39 peptide is: GGLPVPLDQTLPLN-VNPA (SEQ ID NO:11). A control peptide of G22-A39 was made by alphabetizing the sequence, named ABC. The sequence of ABC is: ADGGLLLLNNPPPPQTVV (SEQ ID NO:13). Both peptides were used with either a free or biotinylated N-terminus as needed. Biotinylation had no effect on G22-A39's ability to inhibit ENaC (n=6).

Microelectrode Studies.

A single-barreled potential difference-sensing electrode was placed in the airway surface liquid by micromanipulator and used in conjunction with a macroelectrode in the serosal solution to measure transepithelial voltage using a voltmeter (World Precision Instruments). Trypsin (2 U/ml; Sigma) was added mucosally as a dry powder in perfluorocarbon to test for changes in regulation of ENaC as previously described (Tarran et al., *J. Gen. Physiol.* 127:591 (2006)). Transepithelial resistance was routinely measured using the EVOM system (WPI) as previously described (Tarran et al., *J. Gen. Physiol.* 127:591 (2006)).

Oocyte Studies.

*Xenopus laevis* oocytes were harvested and injected as described (Donaldson, et al., *J. Biol. Chem.* 277:8338 (2002)). Defolliculated healthy stage V-VI oocytes were injected with 0.3 ng of CRNA of each ENaC subunit. Injected oocytes were kept in modified Barth's saline (in mM: 88 NaCl, 1 KCl, 2.4 NaHCO$_3$, 0.3 Ca(NO$_3$)$_2$, 0.41 CaCl$_2$, 0.82 MgSO$_4$, and 15 HEPES, adjusted to pH 7.35 with Tris). Oocytes were studied 24 hr after injection using the two electrode voltage clamp technique as previously described (Donaldson, et al., *J. Biol. Chem.* 277:8338 (2002)). Oocytes were clamped at a holding potential of −60 mV. The change in amiloride-sensitive whole cell current as an indicator of ENaC activity was determined by subtracting the corresponding current value measured in the presence of 10 µM amiloride from that measured before the application of amiloride. Where appropriate, oocytes were incubated with G22-A39 or ABC for 1 h prior to recording. In some experiments β-ENaC$^{S518C}$ was used which forms ENaCs that are locked into an open probability near 1.0 by exposure to the sulthydral reactive reagent [2-(Trimethyl-ammonium)ethyl] methanethiosulphonate bromide (MTSET). MTSET was added at a concentration of 1 mM to the oocyte bath as previously described (Snyder, *J. Clin. Invest.* 105: 45 (2000)).

Western Blotting:

Airway surface liquid collected as described above was also placed in protease-inhibitor cocktail (Roche) for Western blotting. The protein concentration was determined using the BCA Assay (Pierce). To obtain SPLUNC1 from *Xenopus* oocytes, oocytes were lysed in Laemmli buffer or oocyte media was directly sampled and placed in Laemmli buffer. Proteins were resolved using SDS-PAGE and transferred to a Polyvinylidene Fluoride (PVDF) membrane. The membrane was then probed using αSplunc1 or αV5 antibodies and a Donkey anti-Mouse HRP antibody (R&D). The blots were then incubated with ECL reagents (Pierce).

Binding Assay:

JME nasal epithelial cells which did not express ENaC were stably infected with a lentivirus containing yfp-αNaC or empty vector (control). JME cells were incubated with varying concentrations of Texas red-labeled SPLUNC1 for 30 min followed by a 5× wash with PBS. After this time images were acquired with a Nikon Ti-S inverted microscope and were quantified to obtain specific and non-specific binding using Image J. Data were then fitted with a Hill Plot to obtain the $K_d$.

shRNA-Induced Knockdown of SPLUNC1:

Our strategy was to select shRNA sequences from Dharmacon that targeted SPLUNC1 effectively by using transient siRNA in an immortalized human airway epithelial cell line (denoted AALEB) (Lundberg et al., *Oncogene* 21:4577 (2002)). We then generated viruses encoding the most effective siRNA. Passage-1 airway cells surviving one week of selection were then trypsinized and plated down on 12 mm T-clear inserts and differentiated under air liquid interface conditions. At the time of the functional assays, we measured airway surface liquid SPLUNC1 protein levels by Western blot to verify stable knockdown. An anti-luciferase shRNA-expressing adenovirus was infected separately as a control.

Confocal Microscopy:

To label airway surface liquid, Ringer containing Texas Red-dextran (2 mg/ml; Invitrogen) was added to human bronchial epithelial culture mucosal surfaces. Perfluorocarbon was added mucosally to prevent evaporation of the airway surface liquid and the culture placed in a chamber containing 100 µl Ringer on the stage of a Leica SP5 confocal microscope with a 63× glycerol immersion objective. 5 points per culture were scanned and an average airway surface liquid height determined. For confocal microscopy human bronchial epithelial cultures were bathed serosally in a modified Ringer solution containing (mM): 116 NaCl, 10 NaHCO$_3$, 5.1 KCl, 1.2 CaCl$_2$, 1.2 MgCl$_2$, 20 TES, 10 glucose, pH 7.4). At all other times, human bronchial epithelial cultures were maintained in a modified BEGM growth medium which contained 24 mM NaHCO$_3$ gassed with 5% CO$_2$. Perfluorocarbon (FC-77) was obtained from 3M and had no effect on ASL height as previously reported.

Flp-in HEK293 Cell Culture and SPLUNC1 Protein Purification:

Flp-In HEK293 cells (Invitrogen) were transfected with pcDNA5/FRT/V5-his-TOPO/hSplunc1 vector. SPLUNC1-expressing clones were selected using hygromycin, isolated, and analyzed for expression. The clones which stably express SPLUNC1 were cultured in T75 flasks in DMEMH media containing 5% Fetal Bovine Serum and at 37° C. in 5% CO$_2$. His-tagged SPLUNC1 was purified from cultured media by dialyzing the media into the His-Select Binding Buffer (50 mM sodium phosphate, pH 8.0, 300 mM sodium chloride, 10 mM imidazole) overnight at 4° C., incubating the dialyzed media with His-Select Nickel Affinity Matrix (Sigma) for 4 hours at 4° C. on an end-over-end rotator in the presence of protease inhibitors (Roche), applied to a column, and washed with 40 ml of His-Select Binding Buffer. SPLUNC1 was then eluted from the Cobalt affinity matrix in 0.5 ml fractions with 600 mM imidazole in His-Select Binding Buffer. Purified SPLUNC1 was then exchanged into Ringer. Cultured media from FlpIn HEK293 cells lacking SPLUNC1 was processed in the same way as media from FlpIn HEK293-SPLUNC1 cells and used as control for experiments where purified SPLUNC1 was added.

Fluorogenic Assay:

To determine whether SPLUNC1 inhibited trypsin activity we assayed cleavage of the Di-tert-butyl dicarbonate-Gln-Ala-Arg-7-methoxycoumarin-4-yl)acetyl (BGAR-MCA) fluorogenic substrate in Ringer (Peptides Int.) excited at 350 nm and emission collected at 460 nm in a 96 well plate reader format (Wallac 1420 VICTOR$^2$). For cell-free assays, reactions were carried out in 50 µl Ringer in a 96 well plate format with 100 µM BGAR-MCA. To measure endogenous protease activity in human bronchial epithelial cultures, 30 µl Ringer with 100 µM BGAR-MCA were placed directly onto the mucosal surfaces of human bronchial epithelial cultures grown on 12 mm T-clear inserts and the cultures were assayed in 12 well plates.

Co-Immunoprecipitation:

*Xenopus* oocytes were injected with either HA-N-Terminus or V5-C-Terminus (HA-NT/V5-CT) tagged subunits in combination with wild type (WT) untagged rat αβγENaC subunits (0.3 ng cRNA each) with or without V5-tagged SPLUNC1 and CAP2 (1 ng cRNA each). After 24 h, 40 eggs per experimental condition were lysed with buffer containing (in mM): 20 Tris, 50 NaCl, 50 NaF, 10 β-glycerophosphate, 5 Na4P$_2$O$_7$ pyrophosphate, 1 EDTA, pH 7.5 and protease inhibitors (complete, Roche), aprotinin (Sigma). Cell lysates were prepared by passing the eggs through a 27G1/2 needle twice and by centrifugation at 3,600 rpm for 10 minutes at 4° C. Supernatants were transferred to new tubes and samples were spun at 14,000 rpm for 20 minutes at 4° C. Supernatants were discarded and pellets were solubilized in (mM) 50 Tris, 100 NaCl, 0.1% Triton X-100, 0.1% NP-40, 20 NaF, 10 Na$_4$P$_2$O$_7$, 10 EDTA+protease inhibitor cocktail (Sigma), pH 7.5. Total inputs were taken from whole cell samples representing 4% of total protein. Solubilized proteins were incubated with 50 µl of protein A and 5 µl of anti-HA antibody (Covance) overnight while tumbling at 4° C. Samples were washed three times with (mM) 150 NaCl 50 Tris pH 7.5 buffer. Laemmli buffer was added and samples were loaded on a 15% gradient Tris-glycine gel after incubation for 10 minutes at 96° C. Samples were transferred to PVDF membranes and Western blot analysis was performed using an anti-V5 (Invitrogen) monoclonal antibody. SPLUNC1 bound to ENaC only when ENaC and SPLUNC1 lysates were used. Uninjected and SPLUNC1 lysates lacking ENaC were both negative for co-immunoprecipitation.

Figure 8:
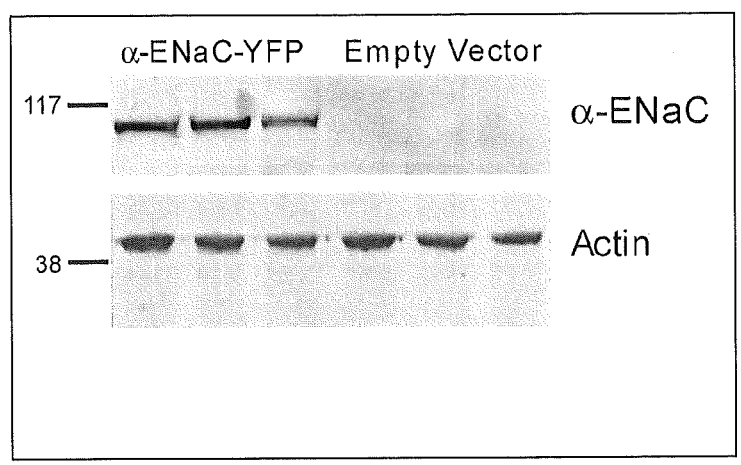
FIG. 8 shows a Western blot showing αENaC expression in JME cells stably transfected with pQCXIN-α-ENaC-YFP but not in cells from the same passage infected with the empty pQCXIN vector

Generation of yfp-αENaC Expressing Cell Line and SPLUNC1 Binding Assay:

The yfp-αENaC construct has previously been shown to function normally (Berdiev et al., *J. Biol. Chem.* 282:36481 (2007)) and was subcloned into a lentiviral vector (pQCXIN). JME nasal epithelial cells express functional ENaCs (Tong et al., *Am. J. Physiol. Lung Cell. Mol. Physiol.* 287:L928 (2004)). However, this attribute is lost after several passages. Thus, passaged JME cells that no longer expressed ENaC were stably infected with a lentivirus containing yfp-αENaC or an empty vector as a control and the presence or absence of αENaC was confirmed using an antibody that was constructed "in-house" that was directed against αENaC (FIG. 8).

Recombinant SPLUNC1 was labeled with Texas red according to the manufacturer's instructions (Pierce) and was freshly labeled on the day of each binding experiment. JME cells were plated on 12 mm T-Clear culture inserts (Corning Costar) and were cultured until confluent. Cultures were then washed 3× with PBS to remove cellular debris and incubated with varying concentrations of Texas red-SPLUNC1 for 30 min in PBS$^{++}$ (with Ca$^{2+}$ and Mg$^{2+}$; 10 µl total volume) followed by a 5× wash with PBS. After this time yfp (514 nm excitation) and Texas red fluorescence (590 nm excitation) were imaged under a 60× water objective on a Nikon Ti-S inverted microscope equipped with an Orca CCD camera (Hamamatsu) switchable filter wheels (Ludl). Background fluorescence was subtracted from all images and the mean thresholded intensity was quantified to obtain specific and non-specific binding using Image J.

PCR and Primer Sequences:

PCR was performed using Amplitaq Gold Mastermix (ABI) and primers specific for SPLUNC1 at a final concentration of 200 nM. The primers used were: forward 5'-ctgatg-gccaccgtcctat-3' (SEQ ID NO:3) and reverse 5'-aggtggatc-ctctcctgctt-3' (SEQ ID NO:4). The reaction was performed according to the manufacturer's instructions with an extension time of 30 seconds for an Eppendorf MasterCycler. Water was used as a negative control, and SPLUNC1 cDNA as a positive control. Human cDNA was prepared from 200 ng of RNA using superscript II (Invitrogen), and 1 µl was used for each reaction. A product of the appropriate size ~150 bp was detected by gel electrophoresis.

Electrophysiological Measurements of Acid-Sensing Ion Channels (ASICs):

Previously described cell lines expressing human ASIC1a, human ASIC2a and rat ASIC3 were used in these experiments (Poirot, *J. Biol. Chem.* 279: 38448 (2004))). Electrophysiological measurements were carried out with an EPC10 patch-clamp amplifier (HEKA Electronics, Lambrecht, Germany) as previously described (Blanchard et al., *Pflugers Arch.* 461:123 (2011)).

Peptide Pull-Down Assay and Western Blotting:

HEK293T cells were transfected with double-tagged human ENaC subunits with HA and V5 epitopes at the N- and C-termini, respectively, in combination with wild-type untagged subunit cDNA. When all three ENaC subunits were expressed, 0.5 µg of each subunit were transfected per well. When expressed individually, 0.75 µg of the subunit were transfected per well. The transfected cells were lysed 24 h later using NP-40 buffer with 1× complete EDTA-free protease inhibitor (Roche, Basel, Switzerland). The lysate was centrifuged at 16,300×g for 15 minutes at 4° C. and the supernatant collected. Protein concentration was determined using the BCA assay and 500 μg of protein plus 0.25 mg peptide and 100 μL of neutravidin were added to a spin column and rotated end-over-end at 4° C. for 24 h (all ThermoFisher Scientific, Rockford, Ill., USA). Flow-through was collected by centrifugation at 1000×g for 30 s. The beads were then washed 5× with NP-40 buffer. Bound protein was eluted by boiling at 95° C. for 10 minutes in 75 μL of 2×LDS NuPAGE sample buffer with 1× sample reducing agent followed by centrifugation at 16,300×g for 2 minutes. Samples were resolved on 4-12% Bis-Tris gels in MES and transferred to a nitrocellulose membrane using iBlot, setting P3 for 8 min (Invitrogen, Carlsbad, Calif., USA). The membrane was probed using 1:1000 anti-V5 antibody (Invitrogen, Carlsbad, Calif., USA) overnight at 4° C. in 3% fish gelatin in TBS-T. The blot was then incubated for 1 h at room temperature with an ECL sheep anti-mouse IgG secondary antibody and detected by ECL reagent (ThermoFisher Scientific, Waltham, Mass., USA) or by incubation with a goat anti-mouse IRDye secondary antibody and analyzed by an Odyssey infrared imaging system (LI-COR Biosciences, Lincoln, Nebr., USA).

Deglycosylation:

Peptide pull-down assays were performed as described above. Samples were eluted by the addition of 100 μL of 0.1 M sodium citrate, pH 5.5, 0.1% SDS to the beads and incubating at 100° C. for 2 minutes, followed by centrifugation at 16,300×g for 2 minutes. The samples were divided equally, and one half was treated with 1 μL of EndoH and incubated at 37° C. for 2 min. After incubation, all samples were lyophilized and then reconstituted in 30 μL LDS NuPAGE sample buffer with 1× sample reducing agent (Invitrogen, Carlsbad, Calif., USA). Western blots were completed as described above. A concentration of 5 μg/ml tunicamycin (Sigma-Aldrich, St Louis, Mo., USA) was added to the cell transfection media and the cells were incubated overnight at 37° C./5% $CO_2$. The following day the protocol for the peptide pull-down assay was performed as described above.

ASL Height Measurement:

To label the ASL, PBS containing 10 kDa Rhodamine dextran (0.2-2 mg/mL; Invitrogen, Carlsbad, Calif., USA) was added to HBEC mucosal surfaces as previously described (Tarran et al., Mol. Cell 8:149 (2001)). When added, peptides with or without 100 nM neutrophil elastase, 1 U/mL aprotinin, activated neutrophil supernatant (ANS) (Haynes et al., Am. J. Physiol. Heart Circ. Physiol. 294:H379 (2008)) or 10 μM sivelestat (Sigma-Aldrich, St Louis, Mo., USA) were added to the mucosal surface along with the Rhodamine dextran. Bumetanide (100 μM) was added to the serosal solution.

In Vivo Studies:

To study the effects of SPLUNC1-derived peptides on the in vivo kidney, mice were anesthetized. After a baseline 45 min control clearance period, S18-type peptide or amiloride were infused intravenously over 30 min and the natriuretic response recorded over the subsequent 2-3 h.

Statistical Analyses:

All data are presented as the mean±SE for n experiments. Airway cultures derived from three or more separate donors were used for each study and each oocyte study was repeated on three separate occasions. Differences between means were tested for statistical significance using paired or unpaired t tests or their non parametric equivalent as appropriate to the experiment. From such comparisons, differences yielding $P \leq 0.05$ were judged to be significant. All binding assays were fitted to the Hill equation.

EXAMPLE 2

Identification of SPLUNC1

Based on the ability of normal human bronchial epithelial cultures to regulate airway surface liquid height to 7 μm, which was paralleled by a decrease in trypsin-sensitive ENaC activity, we speculated that a soluble protease inhibitor is present in the airway surface liquid during normal airway surface liquid volume homeostasis. We searched for potential protease inhibitors/ENaC regulators by incubating trypsin-coated beads with airway surface liquid and performing a proteomic analysis. Airway surface liquid was collected by lavaging human bronchial epithelial cultures with 100 μl PBS at 37° C. for 15 min, incubated overnight at 4° C. with trypsin-agarose beads±aprotinin, separated on a 15% SDS page gel and visualized with a silver stain (FIG. 1). Bands were removed from the gel for analysis by mass spectrometry and the identities of these proteins are listed in Table 2. Of note, SPLUNC1 was visible as a ~26 kD protein (band 1) and as a ~19 kD fragment (band 2) and its binding to trypsin was moderately out-competed by the addition of the protease inhibitor aprotinin (FIG. 1). The mass spectrometry analysis allowed us to identify SPLUNC1 as one of the major proteins that bound to the trypsin-beads (FIG. 2A; Table 2). The presence of SPLUNC1 was confirmed in airway surface liquid by Western blot (FIG. 2B).

TABLE 2

| Band No. | Protein Name | Accession No. |
|---|---|---|
| 1 | SPLUNC1 | AAF70860 |
| 2 | SPLUNC1 | AAF70860 |
|  | AY513239 | AAR89906 |
| 3 | Complement C3 Precursor | C3HU |
| 4 | Hypothetical Protein | Q8WVW5_HUMAN |

Figure 3:
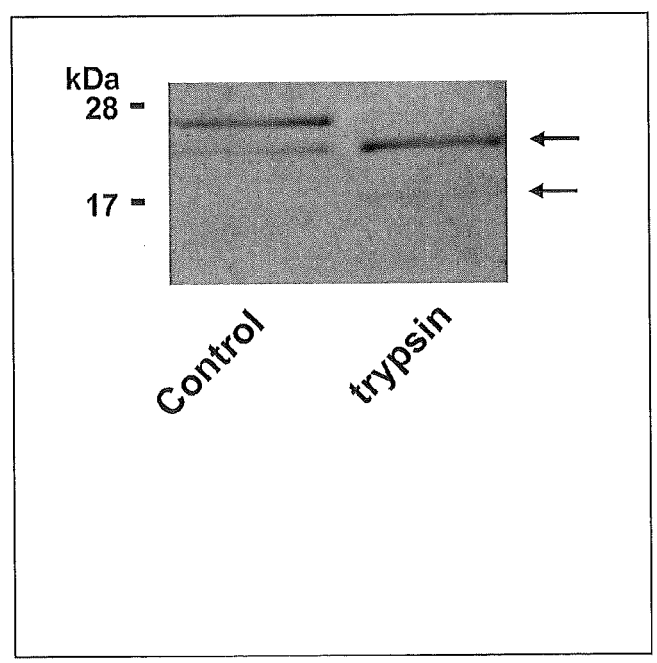
FIG. 3 shows that SPLUNC1 is cleaved by trypsin. A 60 min treatment with 1 U/ml trypsin caused both a ~1 kDa and a 10 kDa shift in SPLUNC1 size. SPLUNC1 was labeled C-terminally with a V5 tag and detected with an anti-V5 antibody. SPLUNC1 cleavage products are shown with arrows.

To better study SPLUNC1, we stably transfected V5/6His-tagged SPLUNC1 into HEK293 cells and purified secreted V5/6His-SPLUNC1 from HEK293 media over a nickel column. Recombinant SPLUNC1 (rSPLUNC1) could be detected using the anti-V5 antibody (FIG. 3) and a brief (30 min) incubation with trypsin resulted in the appearance of cleavage products of C-terminally V5-tagged rSPLUNC1, indicating that SPLUNC1 is a substrate for serine proteases (FIG. 3). To test whether SPLUNC1 was capable of altering airway ion transport, we then measured the transepithelial voltage under thin film conditions in human bronchial epithelial cultures±rSPLUNC1 with time. Washing the mucosal surface of human bronchial epithelial cultures with PBS has previously been shown to maximally activate ENaC (Tarran et al., J. Gen. Physiol. 127:591 (2006)) and also removes endogenous SPLUNC1 (FIG. 3B). Under these conditions, 20 μl of Ringer containing 50 ng/ml of rSPLUNC1 significantly reduced the transepithelial voltage (FIG. 2C). In contrast, a purified SPLUNC1-free fraction of HEK293 media was without effect (FIG. 2C). To confirm that this inhibition was due to altered ENaC regulation, we exposed human bronchial epithelial cultures to trypsin for 30 min after the 1 h rSPLUNC1 exposure. Trypsin was without effect in the control human bronchial epithelial cultures, suggesting that ENaC remained fully active. However, mucosal trypsin exposure significantly raised the transepithelial voltage in the SPLUNC1-exposed group, suggesting that ENaC had been inhibited by rSPLUNC1 (FIG. 2C). Inhibition of the transepithelial voltage occurred at identical rates following both rSPLUNC1 and aprotinin addition and the effects of these compounds were not additive. However, in both cases, these effects were reversed by trypsin-exposure (FIG. 2D, 2E): Taken together, these data suggest (i) that both molecules operated through a common pathway and (ii) that this was an ENaC-specific effect (FIG. 2D, 3E). Further, when airway surface liquid was left to accumulate on human bronchial epithelial culture surfaces for 24 h (i.e., the cultures were not pre-washed with Ringer), the transepithelial voltage was significantly lower than in washed cultures and rSPLUNC1 addition was without further effect, suggesting that the spontaneous accumulation of an endogenous inhibitor in the airway surface liquid reduces the transepithelial voltage and that maximum inhibition is reached at steady state (FIG. 2E).

Since SPLUNC1 binds to trypsin (FIG. 3), we explored the possibility that SPLUNC1 is proteolytically cleaved in the process. There was both a ~1 kDa and a 10 kDa shift in mobility of C-terminally V5-tagged rSPLUNC1. The ~16 kDa band, likely corresponds to the $2^{nd}$ SPLUNC1 band detected by mass spectrometry (FIG. 1 and Table 2), suggesting that endogenous SPLUNC1 is cleaved in airway surface liquid.

EXAMPLE 3

SPLUNC1 Regulates Ion Transport

Figure 4:
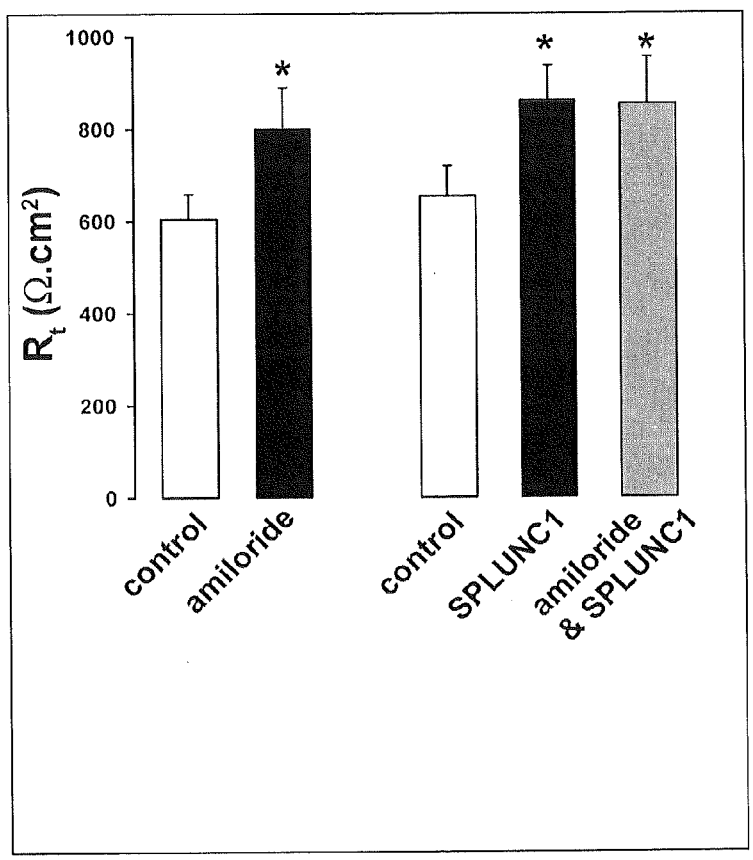
FIG. 4 shows that SPLUNC1 affects the transepithelial resistance (Rt) in a similar fashion to amiloride. Human bronchial epithelial cultures were washed 5× with PBS over 1 h to remove any native SPLUNC1 and then exposed to 50 ng/ml recombinant SPLUNC1 for 30 min or 100 mM amiloride for 10 min or SPLUNC1 followed by amiloride. All n=12. *=$p<0.05$ different to control.

To test whether passive fluxes were affected by SPLUNC1 exposure, we measured the effects of amiloride on transepithelial voltage vs. transepithelial electrical resistance±rSPLUNC1. Amiloride reduced the transepithelial voltage by 54% (n=12) and rSPLUNC1 addition to the same amiloride-treated cultures was without further effect (n=12). In parallel, both amiloride and rSPLUNC1 increased the transepithelial electrical resistance by ~33% and again the effects were not additive, suggesting that amiloride and SPLUNC1 both act on ENaC in the apical membrane and increase the apical membrane resistance in human bronchial epithelia, rather than by affecting paracellular transport (FIG. 4).

Figure 5:
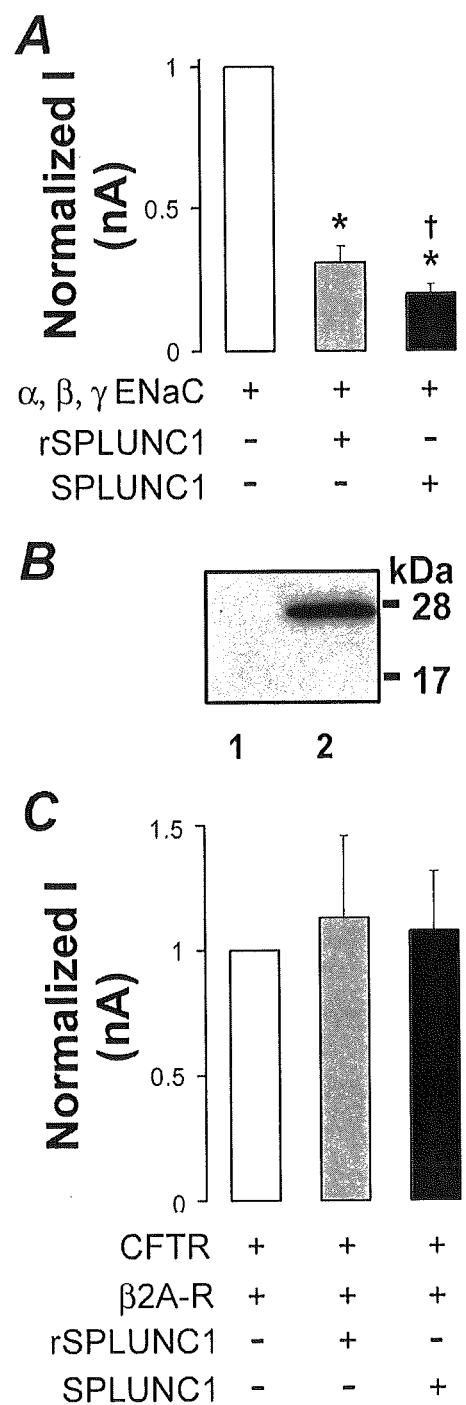
FIGS. 5A-5C show the effect of expressing SPLUNC1 and ENaC in *Xenopus* oocytes.

To further investigate how SPLUNC1 regulated ion transport and ENaC in particular, we expressed αβγENaC in *Xenopus laevis* oocytes and either exposed oocytes to rSPLUNC1 or co-injected SPLUNC1 cRNA into the oocytes with αβγENaC. ENaC currents were reduced by ~70% when oocytes were incubated with rSPLUNC1 prior to recording (FIG. 5A). Due to the larger volumes required for oocyte incubations, SPLUNC1 was added at a 10× lower concentration than in the human bronchial epithelial cultures (5 ng/ml). co-expression of αβγENaC and SPLUNC1 also resulted in ENaC inhibition by ~70% (FIG. 5A). SPLUNC1 could not be detected in media from oocytes injected with αβγENaC (FIG. 5B). However, SPLUNC1 was readily detected in the media after coinjection of SPLUNC1 and αβγENaC cRNAs (FIG. 5B). Since SPLUNC1 could be detected in the oocyte media (FIG. 5), it is likely that co-expressed SPLUNC1 was secreted by the oocytes and inhibited ENaC externally in a similar fashion to rSPLUNC1.

To test whether SPLUNC1 specifically inhibited ENaC, we either exposed CFTR-expressing oocytes to 5 ng/ml rSPLUNC1 or co-expressed SPLUNC1 and CFTR. In both cases, we co-expressed CFTR with the β2 adrenergic receptor (β2AR) which can be stimulated with isoproterenol to raise cAMP and stimulate CFTR (Uezono et al., *Receptors Channels* 1:233 (1993)). Following 10 μM isoproterenol exposure, CFTR was robustly activated and unlike with ENaC, rSPLUNC1 exposure or injection of SPLUNC1 cRNA had no inhibitory effect on CFTR activity, suggesting that the inhibitory effects of SPLUNC1 are specific for ENaC (FIG. 5C).

EXAMPLE 4

SPLUNC1 Inhibits Cleavage of ENaC

Figure 6:
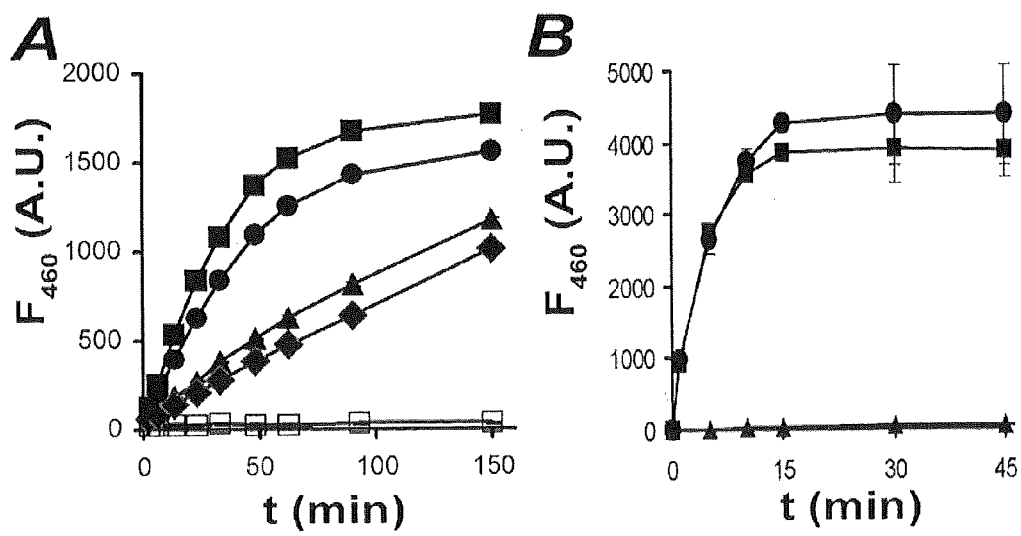
FIGS. 6A-6B show the effect of SPLUNC1 on cleavage of ENaC.

Since SPLUNC1 bound to trypsin-agarose beads (FIG. 1) and affected the trypsin sensitivity of ENaC (FIG. 2C), we next tested whether SPLUNC1 could alter serine protease activity. Despite rSPLUNC1 being capable of inhibiting ENaC by ~70% in both human bronchial epithelia and oocytes (FIGS. 1 and 2), 50 ng/ml rSPLUNC1 had only a modest affect (~10%) on the ability of either 1.0 or 0.3 U/ml trypsin to cleave a fluorogenic substrate (Di-tert-butyl dicarbonate-Gln-Ala-Arg-7-methoxycoumarin-4-yl)acetyl; BGAR-MCA), unlike 2 U/ml aprotinin which inhibited trypsin activity by ~100% (FIG. 6A). Airway epithelia express serine proteases and mucosal addition of Ringer solution containing BGAR-MCA to human bronchial epithelial cultures resulted in spontaneous BGAR-MCA cleavage with time that was inhibited by aprotinin addition, confirming that serine proteases are indeed active on the mucosal surface of airway epithelia (FIG. 6B). rSPLUNC1 had no significant affect on BGAR-MCA cleavage in human bronchial epithelial mucosal surfaces, suggesting that SPLUNC1 does not inhibit ENaC by inhibiting serine protease activity (FIG. 6B).

Proteolytic cleavage of α and γ subunits is required for ENaC activation (Mueller et al., *J. Biol. Chem.* 282:33475 (2007); Adebamiro et al., *J. Gen. Physiol.* 130:611 (2007)) and since CAP2 is highly expressed in human bronchial epithelial cultures (Tarran et al., *J. Gen. Physiol.* 127:591 (2006)), we tested whether SPLUNC1 could alter α and γ ENaC cleavage by CAP2. Due to the relative scarcity of purified rSPLUNC1, we elected to co-express SPLUNC1 and ENaC rather than use rSPLUNC1 for subsequent oocyte studies since SPLUNC1 is secreted at sufficient quantities from oocytes to inhibit ENaC (FIG. 5). When αβγENaC and CAP2 were co-expressed in oocytes, both full-length ENaC subunits and cleaved α and γ fragments were detected with a V5 antibody (FIG. 7A, 7B). However, in the presence of SPLUNC1, only full-length α and γ ENaC subunits could be observed, suggesting that SPLUNC1 protects ENaC from proteolytic cleavage despite SPLUNC1 having no observable intrinsic anti-protease activity (FIG. 7A, 7B). Since we probed with a V5 antibody, SPLUNC, which is also V5-tagged was visible as a 26 kD band. However, SPLUNC1 could be differentiated from ENaC cleavage fragments based on its size and position on the gel (FIG. 7A, 7B). To confirm that SPLUNC1 prevented functional activation of ENaC by CAPs, we co-expressed ENaC±SPLUNC1 with prostasin (CAP1) and CAP2 both of which are present in the airways. As previously described, both CAPs significantly increased basal ENaC currents (Vuagniaux et al., *J. Gen. Physiol.* 120: 191 (2002)). However, the ability of both proteases to activate ENaC was significantly reduced by SPLUNC1 (FIG. 7C). Similarly, trypsin-exposure also increased ENaC activity and this stimulation was attenuated by SPLUNC1 (FIG. 7D). The furin-insensitive $α_{R205,231K}, β, γ_{R138K}$ ENaC mutant was also inhibited by SPLUNC1, suggesting that this effect is not mediated by convertases such as furin (Hughey et al., *J. Biol. Chem.* 279:18111 (2004)) (FIG. 7E).

EXAMPLE 5

SPLUNC1 Binds to ENaC

Figure 9:
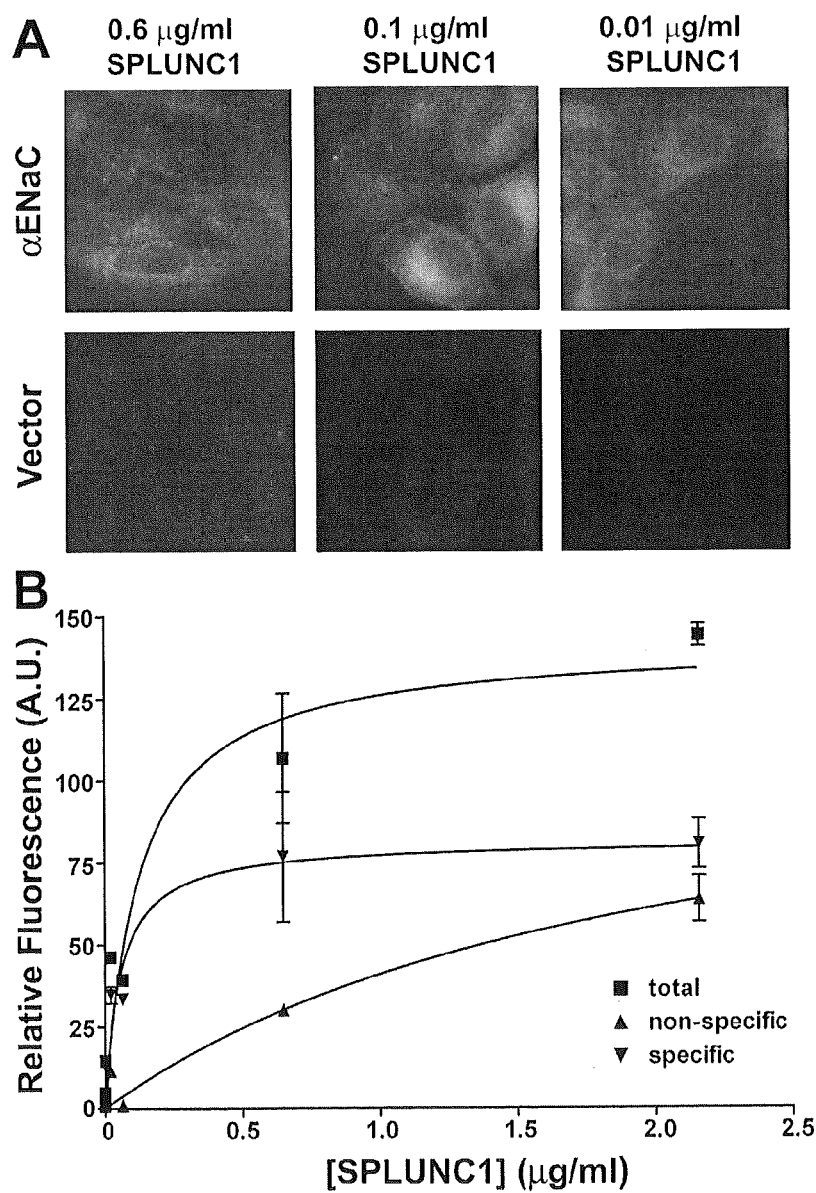
FIGS. 9A-9B show binding of SPLUNC1 to ENaC.

Since SPLUNC1 prevented cleavage and activation of ENaC, but did not appear to be a serine protease inhibitor in the same fashion as aprotinin, we hypothesized that SPLUNC1 could specifically bind to ENaC to protect it from proteolysis. To test this hypothesis, we utilized an airway cell line (JME cells) that had been extensively passaged and did not express ENaC, which we used to measure non-specific binding after infection with a lentivirus containing an empty vector. To measure specific binding, we then infected these cells with a lentivirus containing yfp-tagged αENaC since the αENaC subunit alone has previously been shown to form functional Na$^+$ channels, albeit with a significantly smaller conductance (Kizer et al., *Proc. Natl. Acad. Sci. USA* 94:1013 (1997); McDonald et al., *Am. J. Physiol.* 268:C1157 (1995)). Stable αENaC expression was confirmed by western blot (FIG. 8). To qualitatively test the relationship between yfp-αENaC expression and SPLUNC1 binding, we plated JME cells on glass coverslips and incubated these cells with varying concentrations of Texas red-labeled rSPLUNC1 As can be seen in FIG. 9A, Texas red-rSPLUNC1 and yfp-αENaC clearly colocalize whilst rSPLUNC1 binding to JME cells infected with the lentiviral vector alone was reduced and more diffuse (FIG. 9A). To quantitatively address this issue, we then polarized these cells on filters for seven days. We then incubated these polarized cells with varying concentrations of Texas red-rSPLUNC1 for 30 min followed by a 5× wash with PBS. The subsequent binding isotherm shows a clear difference between non-specific (empty vector-transfected) binding which did not saturate and specific (yfp-αENaC) binding which was significantly greater and saturable (FIG. 9B). Using this graph, we calculated that the $K_d$ was 55 ng/ml (FIG. 9B). Thus, if SPLUNC1 is indeed a volume sensor in the airways, this data suggests that it will be able to change ENaC activity over a narrow range of concentrations.

Figure 10:
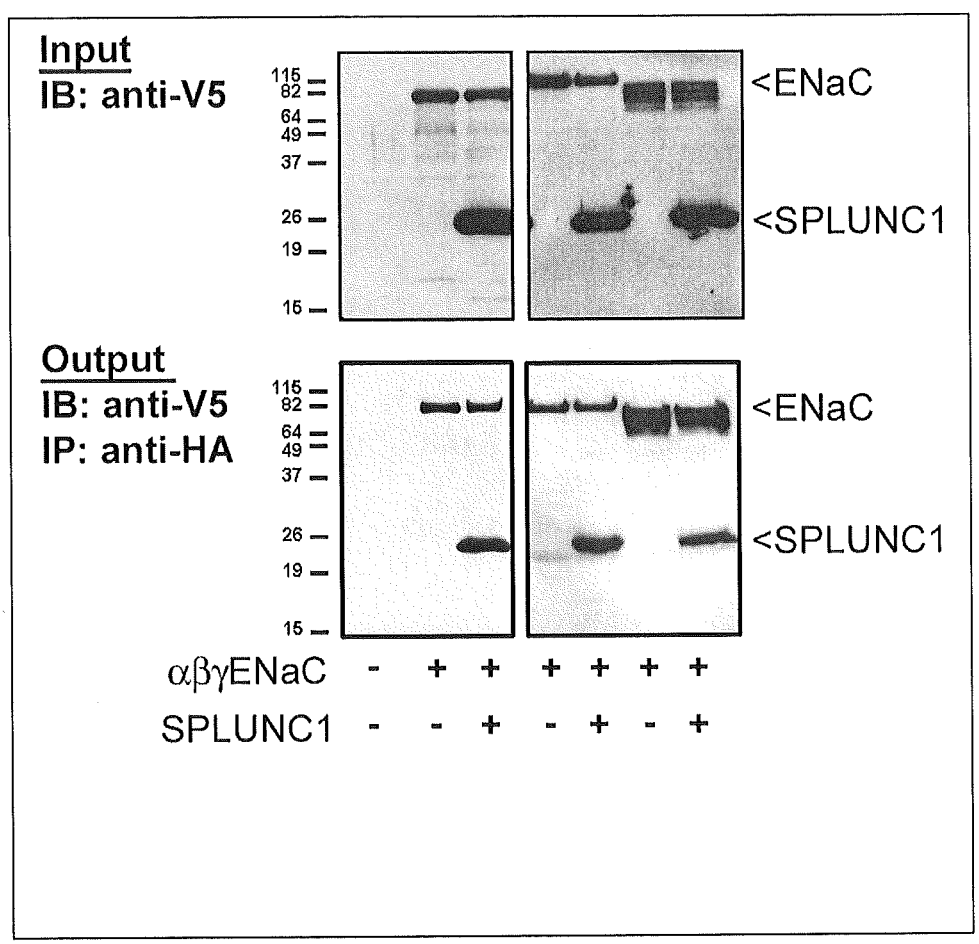
FIG. 10 shows that SPLUNC1 binds to α, β and γENaC subunits. Oocytes were coinjected with 0.3 ng αβγENaC subunits±SPLUNC1 (1 ng). Gels show representative co-immunoprecipitation of V5-tagged SPLUNC1 and HA-tagged ENaC subunits. Arrowheads denote ENaC or SPLUNC1 bands and U.I. denotes uninjected control oocytes.

*Xenopus* oocytes are autofluorescent, making this type of fluorescent binding assay difficult. To test whether SPLUNC1 could also bind to ENaC subunits in *Xenopus* oocytes, we co-expressed HA-tagged N-terminus and V5-tagged C-terminus (HA-NT/V5-CT) αβγ ENaC subunits in combination with wild type (WT) untagged subunits and V5-tagged SPLUNC1 (for example, α-HA-NT/V5-CT,β,γ-ENaC±SPLUNC1-V5) and immunoprecipitated ENaC using anti-HA monoclonal antibodies. We then probed for V5-tagged SPLUNC1 and found that SPLUNC1 bound to all three ENaC subunits (FIG. 10). Thus, rather than being a protease inhibitor, we propose that SPLUNC1 protects α and γ ENaC from being cleaved by serine proteases, perhaps being cleaved itself in the process.

We have previously shown that human bronchial epithelial cultures rapidly absorb excess airway surface liquid and then absorption slows and a steady state airway surface liquid height of ~7 μm is maintained (Tarran et al., (*J. Biol. Chem.* 280:35751 (2005)). To ask if endogenous SPLUNC1 was required as part of this homeostatic mechanism, we knocked down SPLUNC1 using two different an anti-SPLUNC1 shRNA sequences that were incorporated into retroviruses that were used to infect human bronchial epithelial cultures. The shRNAs had the following sequences.

```
shRNA No. 1 Sense
                                    (SEQ ID NO: 5)
AUAAAGUCCUGCCUGAGUUUU shRNA No. 1 Anti-sense
                                    (SEQ ID NO: 6)
5'PAACUCAGGCAGGACUUUAUUU
```

```
shRNA No. 2 Sense
                                    (SEQ ID NO: 7)
GCAGGAAGCUUGACAAAUGUU shRNA No. 2 Anti-sense
                                    (SEQ ID NO: 8)
5'PCAUUUGUCAAGCUUCCUGCUU
```

Figure 11:
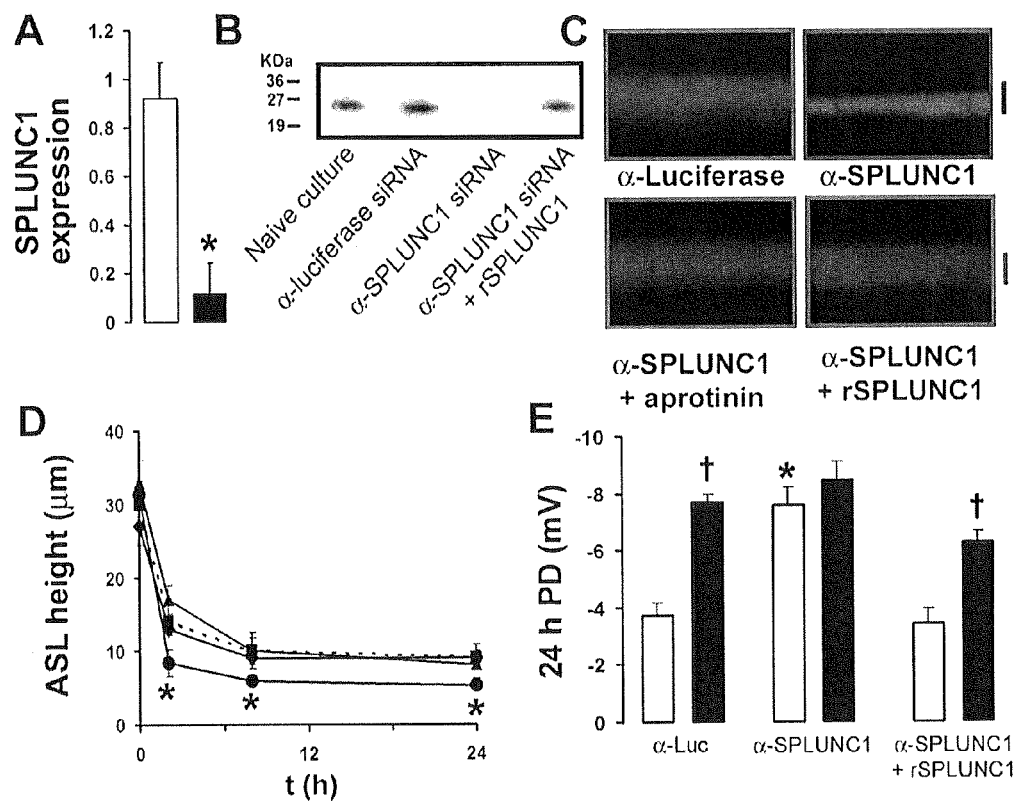
FIGS. 11A-11E show the inhibition of SPLUNC1 with shRNA.

Successful knockdown was confirmed by qPCR and western blot (FIGS. 5A, B) and since no difference in knockdown was detected between each sequence, the subsequent results were pooled. Human bronchial epithelial cultures infected with a control shRNA (anti-luciferase), rapidly absorbed a test solution of 20 μl Ringer until an airway surface liquid height of 7 μm was reached, after which time absorption slowed and airway surface liquid height was maintained at 7 μm as has previously been described for non-infected human bronchial epithelial cultures (FIG. 11C, 11D) (Tarran et al., *J. Gen. Physiol.* 127:591 (2006); Tarran et al., (*J. Biol. Chem.* 280:35751 (2005)). This regulation was paralleled by a decline in the transepithelial voltage which could be restored by mucosal exposure to trypsin (FIG. 11E). Importantly, cultures lacking SPLUNC1 failed to regulate airway surface liquid height with time and exhibited increased airway surface liquid absorption during the initial phase followed by a failure to maintain steady-state airway surface liquid height at 7 μm (FIG. 11C, 11D). Further, the transepithelial voltage failed to decline in human bronchial epithelial cultures lacking SPLUNC1 and remained both elevated and trypsin-insensitive, suggesting that ENaC remained fully activated. Regulation of both airway surface liquid height and the transepithelial voltage was restored by the addition of 50 ng/ml rSPLUNC1 to the airway surface liquid (FIG. 11C-11E), suggesting that SPLUNC1 indeed acts as a reporter molecule in the airway surface liquid that regulates ENaC activity to maintain appropriate airway surface liquid volume control.

Figure 2:
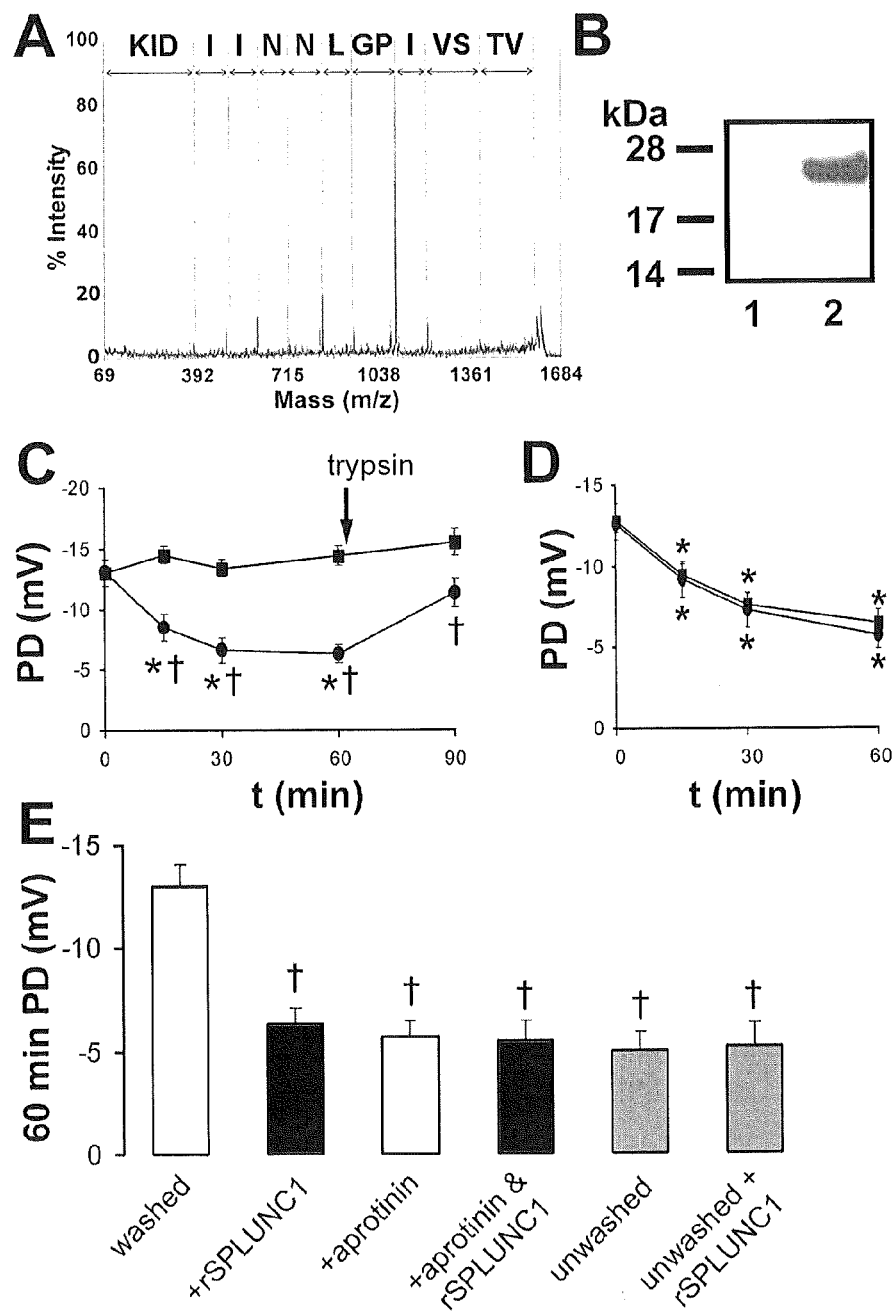
FIGS. 2A-2E show the presence and function of SPLUNC1 in airway fluid.
Figure 7:
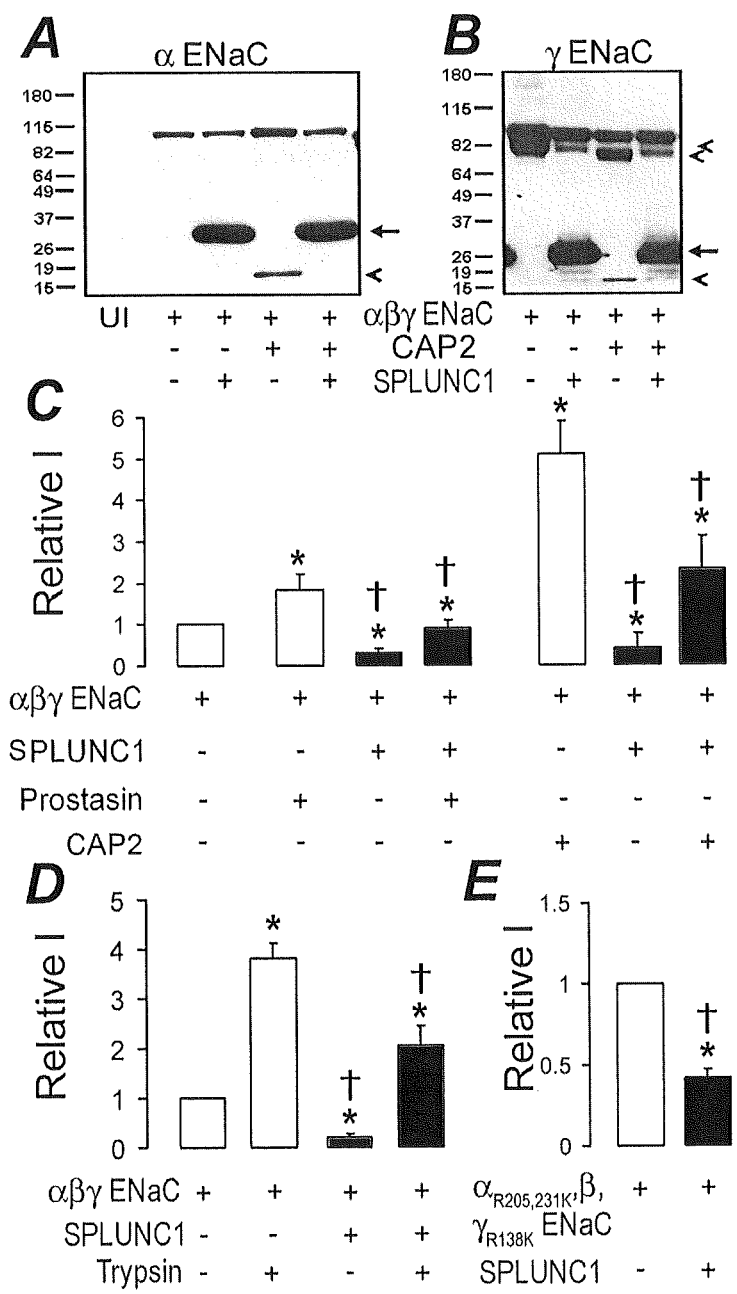
FIGS. 7A-7E show the effect of expressing SPLUNC1 and ENaC is *Xenopus* oocytes.

We propose that SPLUNC1 binds specifically to an extracellular domain of ENaC, preventing the channel from being cleaved and activated by serine proteases. It has been proposed that the extracellular loops of ENaC play a role in channel gating and the α and γ subunits of ENaC have been reported to contain short inhibitory segments that are removed during proteolytic cleavage to activate the channel (Carattino et al., *J. Biol. Chem.* 283:25290 (2008); Carattino et al., *Am. J. Physiol. Renal Physiol.* 294:F47 (2008)). We speculate that ENaC subunits that have already been cleaved by extracellular serine proteases are likely to be SPLUNC1-insensitive. However, as new ENaCs are inserted in the plasma membrane, SPLUNC1 binds to them, preventing their cleavage and resulting in a decline in ENaC-mediated currents. The onset of inhibition (30-60 min; FIG. 2C, 2D) is comparable with aprotinin-inhibition rates in human bronchial epithelial cultures (Bridges et al., *Am. J. Physiol. Lung Cell Mol. Physiol.* 281:L16 (2001); Donaldson et al., *J. Biol. Chem.* 277:8338 (2002)) and is consistent with this model. While the cleavage model is generally accepted, it is also conceivable that proteins which bind to the extracellular loops of ENaC could induce sufficient conformational changes to modulate the activity of the channel. While the slow kinetics of the inhibition with SPLUNC1 are most compatible with the cleavage hypothesis (FIG. 2), we cannot as yet formally exclude the possibility that SPLUNC1 can bind to ENaC and either induce a conformational change in the extracellular loops and/or the pore to block the channel or directly block the channel pore itself. Further, in this study, we did not differentiate between possible effects of SPLUNC1 on the number of ENaC channels vs. their open probability. Since both basal and protease-activated ENaC currents were reduced in the presence of SPLUNC1, the relative increase from basal to protease-activated currents is similar ±SPLUNC1 (FIG. 7). Thus, we cannot exclude the possibility that SPLUNC1 decreases the number of ENaC channels in the plasma membrane. If this was the case, then the pool of surface ENaCs available to be cleaved would be reduced, which could explain both the reduction in ENaC cleavage and protease-activated currents in the presence of SPLUNC1.

Figure 12:
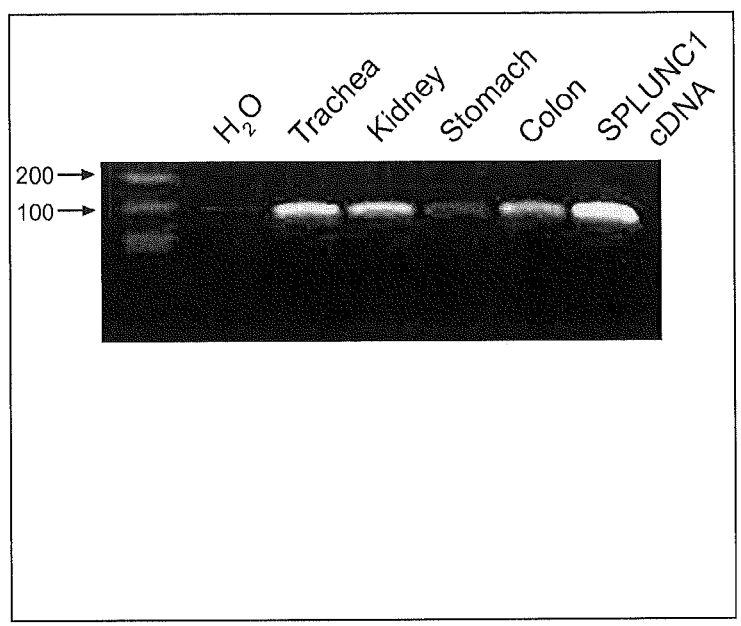
FIG. 12 shows that SPLUNC1 is highly expressed in the trachea, colon and kidney. cDNA was obtained from whole trachea, kidney, stomach and colon vs. specific SPLUNC1 cDNA.

In addition to being expressed in the airways, ENaC is also expressed in aldosterone-sensitive epithelial cells in the colon and kidney where it plays an important role in the control of sodium balance, blood volume, and blood pressure (Kunzelmann et al., *Physiol. Rev.* 82:245 (2002); Rossier et al., *Annu. Rev. Physiol.* 64:877 (2002)). In the colon, the primary flux is in the absorptive direction. However, ion transport can switch from being absorptive to being secretory to help regulate salt balance (Charney et al., *Am. J. Physiol.* 247:G1 (1984); Garty et al., *Physiol. Rev.* 77:359 (1997)). In the kidney, ENaC is the rate-limiting step for salt reabsorption in the collecting duct (20) and aldosterone induces a shift in the molecular weight of γ ENaC from 85 kDa to ≈75 kDa, consistent with physiological proteolytic clipping of the extracellular loop (Masilamani et al., *J. Clin. Invest.* 104:R19 (1999)). As their acronym suggests, palate lung and nasal epithelial clone (PLUNC) family members expression was thought to be limited to a few specific tissues (Bingle et al., *Biochim. Biophys. Acta* 1493:363 (2000)). We performed PCR to determine whether SPLUNC1 was also expressed in other ENaC-expressing tissues. Interestingly, SPLUNC1 was highly expressed in the kidney and colon, but was not expressed in the stomach (FIG. 12), suggesting that SPLUNC1 is expressed in other ENaC-expressing tissues beyond the lung/palate and nasal epithelia. Thus, SPLUNC1 expression in these tissues could potentially add an additional layer of regulation to further modulate ENaC activity and salt absorption.

SPLUNC1 expression is increased in cystic fibrosis lungs, especially in the surface epithelium of the proximal and distal airways (Bingle et al., *Respir. Res.* 8:79 (2007)) and this upregulation may be due to the increased inflammation seen in CF lungs (Chmiel et al., *Respir. Res.* 4:8 (2003)). However, cystic fibrosis lungs are typified by Na$^+$ hyperabsorption and mucus dehydration (Boucher, *Pflugers Arch.* 445:495 (2003)) so it is unlikely that SPLUNC1 exerts any significant inhibitory effect on ENaC under these conditions. Further, we have previously demonstrated that cystic fibrosis bronchial epithelial cultures do not decrease ENaC activity with time (Tarran et al., *J. Gen. Physiol.* 127:591 (2006); Tarran et al., *J. Biol. Chem.* 280:35751 (2005)). CFTR expression is not required for SPLUNC1 to inhibit ENaC, as demonstrated in our oocytes studies, suggesting that this inability of SPLUNC1 to regulate ENaC is not an innate property of cystic fibrosis airways (FIG. 5A). However, the serine proteases that activate ENaC are upregulated in cystic fibrosis airway epithelia (Myerburg et al., *Am. J. Physiol. Lung Cell Mol. Physiol.* 294: L932 (2008)) and neutrophil elastase, which also activates ENaC, is increased in cystic fibrosis airways (Birrer et al., *Am. J. Respir. Crit. Care Med.* 150:207 (1994); Caldwell et al., *Am. J. Physiol. Lung Cell Mol. Physiol.* 288:L813 (2005); Konstan et al., *Am. J. Respir. Crit. Care Med.* 150:448 (1994)). Thus, it is possible that the excessive protease upregulation seen in cystic fibrosis airways (Myerburg et al., *Am. J. Physiol. Lung Cell Mol. Physiol.* 294:L932 (2008)) interferes with the normal regulation of ENaC by SPLUNC1 and other potential ENaC regulators and thereby shifts the balance from anti-proteases and less ENaC activity to a protease-replete state with more ENaC activity, overwhelming the ability of SPLUNC1 to inactivate ENaC and contributing to cystic fibrosis airway surface liquid volume depletion.

In summary, we have identified SPLUNC1 as a novel extracellular protein inhibitor of ENaC that is present in the airway surface liquid. In normal airways, SPLUNC1 is highly expressed in submucosal glands with moderate expression in surface epithelium of the proximal airways with little expression in the distal airways (Bingle et al., *Respir. Res.* 8:79 (2007)). Thus, we propose that SPLUNC1 is secreted from glands and surface epithelium where it serves as a reporter molecule whose dilution or concentration can adjust ENaC activity to regulate airways hydration and mucus clearance. Since SPLUNC1 is secreted by proximal airways, we propose that this regulation primarily occurs in the proximal airways, with little effect in the distal airways.

EXAMPLE 6

SPLUNC2 Inhibits ENaC

Figure 13:
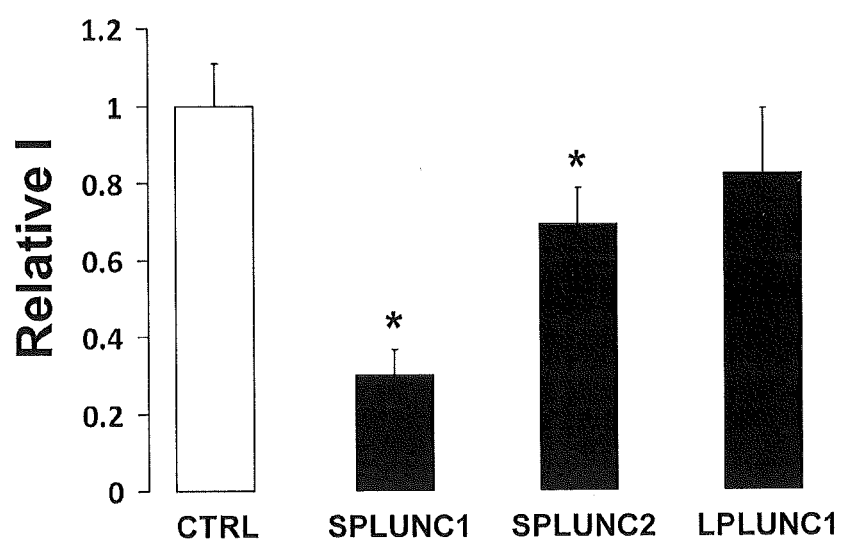
FIG. 13 shows the effect of PLUNC family members on ENaC activity.

SPLUNC1, SPLUNC2, or LPLUNC1 were expressed in *Xenopus* oocytes as described in Example 3. The effect of SPLUNC1, SPLUNC2, and LPLUNC1 on amiloride-sensitive currents was measured (FIG. 13). Current is displayed relative to amiloride-sensitive current from α,β,γ ENaC-expressing oocytes (CTRL, white bar, n=18). Oocytes co-expressing SPLUNC1 showed a ~70% reduction in ENaC current (p<0.0001; n=22). Those co-expressing SPLUNC2 (n=22) exhibited borderline significance (i.e., not significant with ANOVA and significant (p=0.045) with an unpaired t-test). Oocytes co-expressing LPLUNC1 (n=17) had no significant ENaC current reduction in this system. The * denotes p<0.05 difference compared to control oocytes expressing α,β,γ ENaC.

EXAMPLE 7

Reduction Inhibits SPLUNC1 Activity

Figure 14:
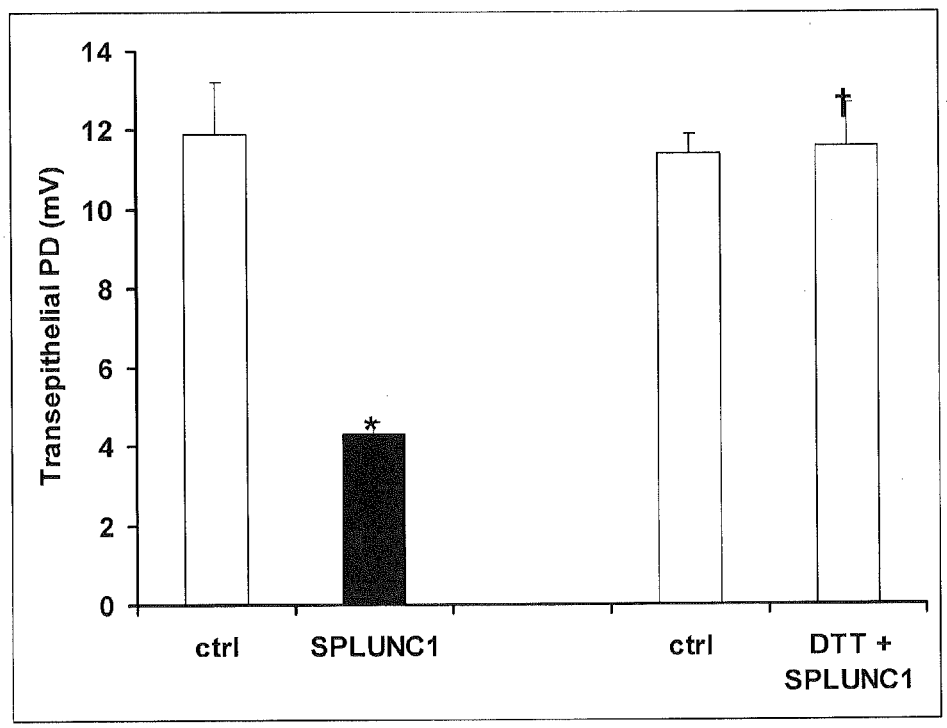
FIG. 14 shows that the ability of SPLUNC1 to inhibit the transepithelial PD is attenuated by DTT pretreatment in primary human bronchial epithelial cultures. Cultures were prewashed to remove endogenous SPLUNC1 and the basal PD was measured (control, ctrl), then either 50 ng/ml recombinant SPLUNC1 or recombinant SPLUNC1 that had been reduced with DTT was added, and the PD was remeasured on the same cultures 45 min later. *=p<0.05 different from control. †=p<0.05 different to SPLUNC1 alone.
Figure 15:
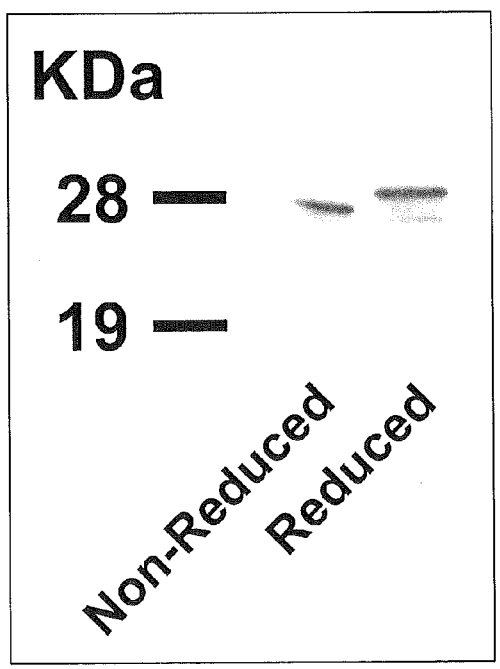
FIG. 15 shows a Western blot run under non-denaturing conditions showing that reduced (i.e., DTT-treated) SPLUNC1 migrates along the gel at a different rate to non-denatured SPLUNC1.

The effect of reducing agents on SPLUNC1 activity was tested in primary human bronchial epithelial cultures (FIG. 14). Cultures were prewashed to remove endogenous SPLUNC1 and the basal PD was measured (control, ctrl), then either 50 ng/ml recombinant SPLUNC1 or recombinant SPLUNC1 that had been reduced with DTT was added, and the PD was remeasured on the same cultures 45 min later. Pretreatment with DTT abolished SPLUNC1 activity. Western blot analysis under non-denaturing conditions showing that reduced (i.e., DTT-treated) SPLUNC1 migrates along the gel at a different rate than non-denatured SPLUNC1 (FIG. 15).

EXAMPLE 8

SPLUNC1 May Decrease the Number of ENaC Channels

Figure 16:
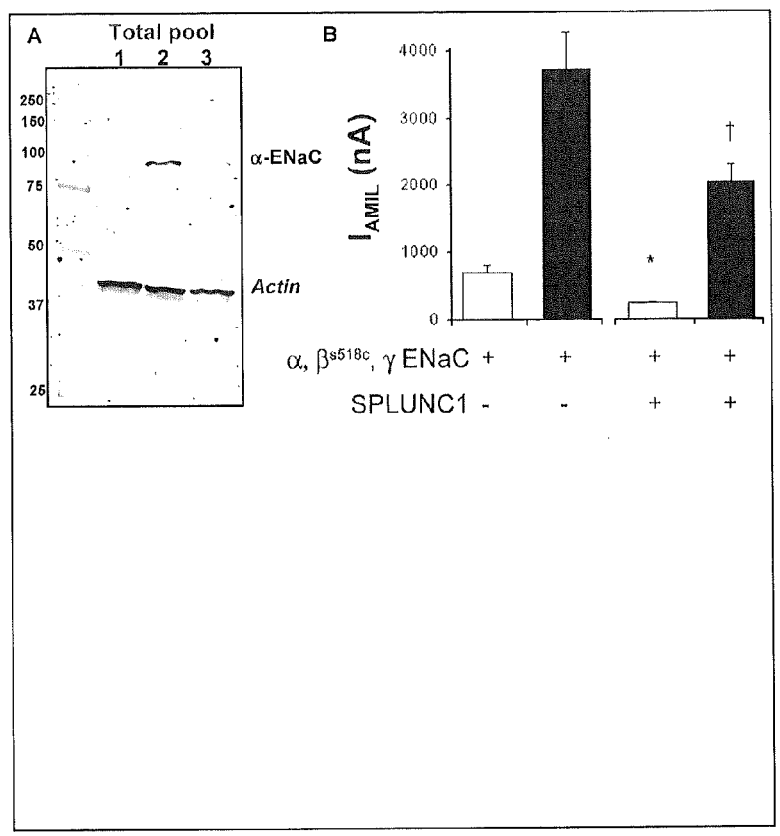
FIGS. 16A-16B show that SPLUNC1 may inhibit ENaC by decreasing the number of ENaC channels in the plasma membrane. A, Surface biotinylation of αENaC shows that plasma membrane ENaC is decreased following coexpression with SPLUNC1 in oocytes. 1, control; 2, αENaC, 3, αENaC & SPLUNC1. Total lysate per lane was 3-4 eggs run on a 10% Gel. B, addition of MTSET to ENaC containing the βS518C mutant increases ENaC $P_o$ to 1.0 when coexpressed in oocytes yet the overall current is still reduced by SPLUNC1 expression, suggesting that ENaC has been internalized. Open bars, control. Closed bars, MTSET addition. All n=6.

The effect of SPLUNC1 on the number of ENaC channels in the plasma membrane was tested by expressing SPLUNC1 and αENaC in *Xenopus* oocytes. After surface biotinylation of αENaC, total lysate was prepared and lysate from 3-4 eggs was separated on a 10% gel. FIG. 16A shows that plasma membrane ENaC is decreased following coexpression with SPLUNC1 in oocytes. The addition of MTSET to ENaC containing the βS518C mutant increases ENaC $P_o$ to 1.0 when coexpressed in oocytes yet the overall current is still reduced by SPLUNC1 expression, suggesting that ENaC has been internalized (FIG. 16B).

EXAMPLE 9

Identification of the SPLUNC1 Active Site

Figure 17:
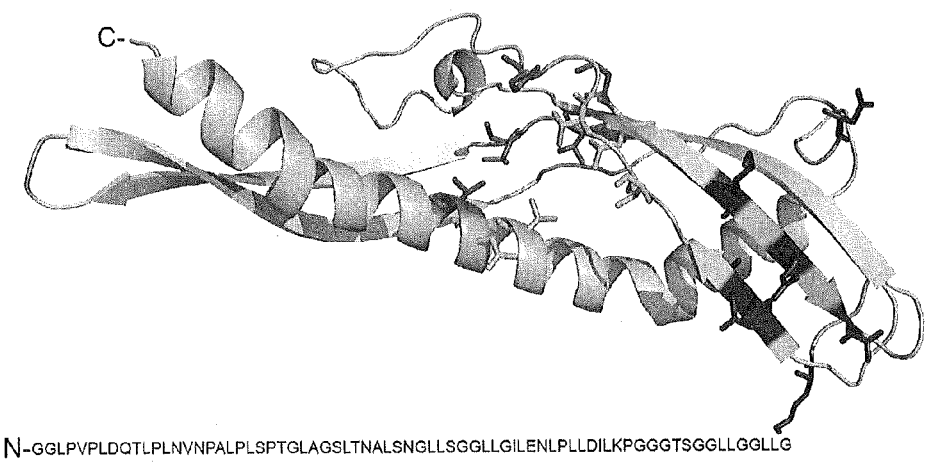
FIG. 17 shows the predicted model of SPLUNC1 (SEQ ID NO:12).

SPLUNC1 is a 256 amino acid protein that contains an N-terminal signal sequence that enables the protein to be secreted extracellularly. A predicted model of SPLUNC1 is shown in FIG. 17. The N-terminal region including the ENaC inhibitory site (highlighted in grey) has no predicted structure. C-terminal truncation mutants of SPLUNC1 were prepared and examined for the ability to inhibit ENaC channels in Xenopus oocytes. The mutant proteins are shown in FIG. 18A. The N-terminal signal peptide sequence (amino acids 1-19) and putative active site (amino acids 22-39) are indicated. Each mutant was tested in the oocyte current inhibition assay described in Example 3. The activity of the truncation mutants is shown in FIG. 18B. Significant inhibition (all p<0.0001) of ENaC was observed with the full-length, 60%, 30%, and 15% proteins. However, deletion of 89% or 98% of SPLUNC1 prevented its inhibition of ENaC. As amino acids 1-19 of SPLUNC1 are a signal sequence that enables the protein to be secreted, this leaves a predicted inhibitory peptide of about 20 amino acids (residues 20-41) as the likely active site for SPLUNC1. Notably, all truncates were secreted into the extracellular media, as checked by western blot, consistent with the hypothesis that SPLUNC1 acts extracellularly.

Figures 18, 19:
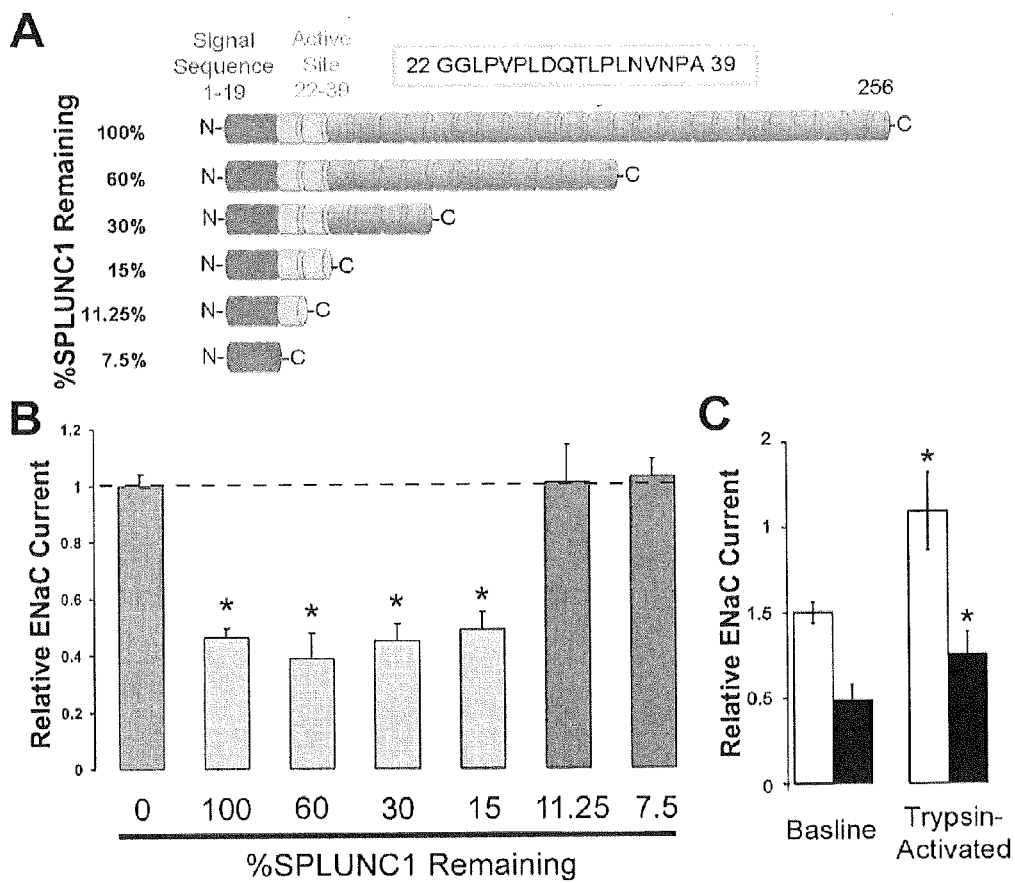
FIG. 19 shows a comparison of the SPLUNC1 amino acid sequence (amino acids 22-39 of SEQ ID NO:1) to the sequence of the α26 and γ43 subunits of ENaC (SEQ ID NOS:9 and 10).

An 18 amino acid peptide that covered the N-terminus portion of SPLUNC1 was prepared, dubbed S18 (SEQ ID NO:11). When placed in the bath solution for 1 h, this peptide inhibited ENaC to the same degree as the full length protein, suggesting that we had identified the active site of SPLUNC1 (FIG. 18C). It is interesting to note that amino acids 22-39 of SPLUNC1 share ~40% homology with the inhibitory fragments of ENaC that are excised upon proteolytic cleavage and are known to inhibit ENaC (FIG. 19). However, since SPLUNC1 acts by reducing the number of ENaC channels at the plasma membrane, whilst the α26 and γ43 subunits of ENaC act by reducing the open probability of ENaC, their mechanism of action appears to markedly differ.

Figure 20:
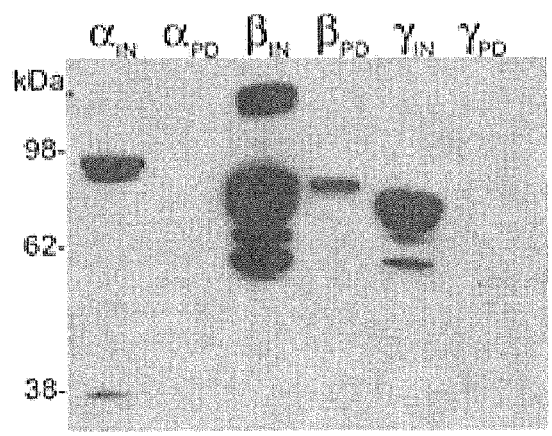
FIG. 20 shows that S18 binds specifically to βENaC. Biotinylated-S18 pull-down of ENaC subunits individually expressed in HEK cells. IN=input, PD=pull-down elution. Input represented 4% of total lysate. Gel was 4-12% bis-tris gradient gel and was repeated 3×.

SPLUNC1 can be co-immunoprecipitated with either α, β, or γENaC. However, when either α, β, or γENaC are immunoprecipitated, the other two subunits are also pulled down as part of a complex. To better define which subunits interact with SPLUNC1, we coexpressed each subunit individually and performed a pull down with biotinylated S18. This peptide binds exclusively to βENaC without any detectable binding to α or γENaC (FIG. 20).

EXAMPLE 10

Characterization of S18

Figure 21:
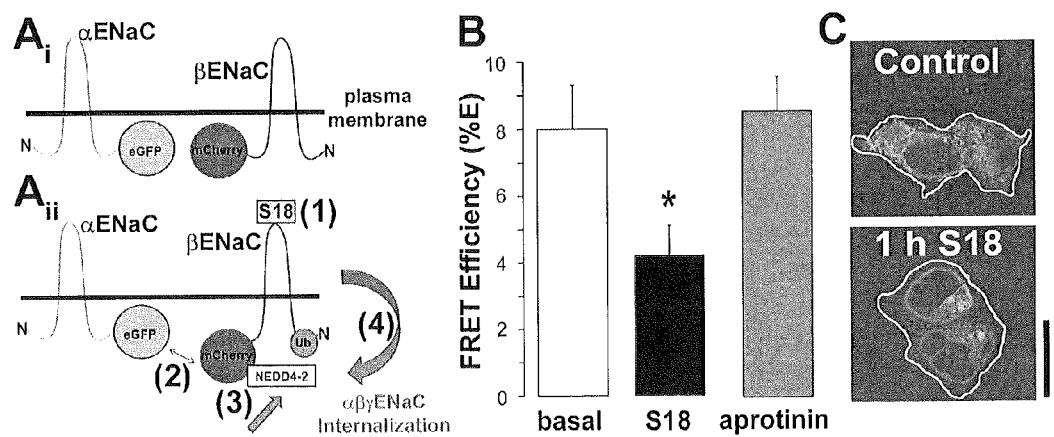
FIG. 21 shows that extracellular S18 binding alters intracellular ENaC FRET. $A_i$, cartoon of αENaC-eGFP and βENaC-mCherry under basal conditions (γENaC not shown). $A_{ii}$ We hypothesize that S18 binding to the extracellular loop of βENaC (1) induces a conformational change in ENaC which is reflected as altered intracellular FRET (2). This change may facilitate NEDD4-2-induced ubiquitination (3), leading to internalization of αβγENaC (4). B, acceptor-photobleaching FRET indicates that α and βENaC subunits change their orientation/distance to each other upon S18 binding, indicating allostery. In contrast, exposure to aprotinin had no effect. All n=8-10. C, Typical confocal images of HEK cells expressing αγENaC and βENaC-eGFP before and 1 h after 100 μM S18. Cell outlines are traced in white.

Since ENaC is regulated by NEDD4-2 binding to its C-termini, which leads to ubiquitination of its N-termini and internalization, we propose that S18 causes a conformational change in ENaC, leading to increased ubiquitination followed by internalization (FIG. 21A). As a first step towards understanding the mechanism of action of SPLUNC1, we performed FRET on fluorescently tagged ENaCs. FRET between αENaC-eGFP and βENaC-mCherry was significantly diminished after one hour of exposure to S18, indicating that extracellular S18 binding induced a change in orientation between α and βENaC C-termini, potentially through an allosteric mechanism (FIGS. 21A and 21B). Furthermore, βENaC-eGFP internalized upon S18 binding (FIG. 21C), consistent with our surface biotinylation data from oocytes.

Figure 22:
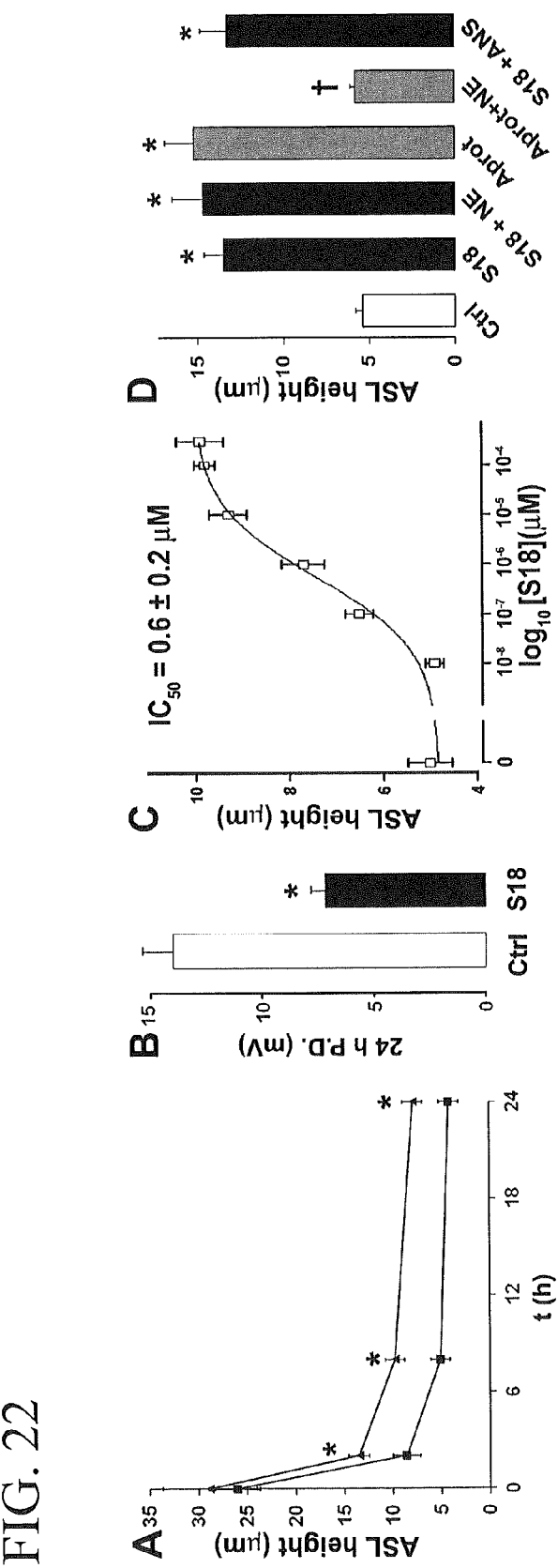
FIGS. 22A-22D show that S18 inhibits cystic fibrosis (CF) hyperabsorption. A, airway surface liquid (ASL) height with time in CF HBECs measured by XZ confocal microscopy after apical addition of 20 μl Ringer with rhodamine-dextran. ■=control; ▲=10 μM S18. Both n=6. B, Thin film amiloride-sensitive transepithelial PD measured in the same cultures as A, with microelectrodes positioned in the ASL and serosal bath. Open bars, control, closed bars, S18, n=6. C, Dose response to S18 vs. ASL height in CF primary human bronchial epithelial cultures (HBECs) measured 8 h after S18 addition. D, Bar graph of 8 h ASL height in CF HBECs. Control (open bars), S18 black bars, aprotinin, gray bars. NE, neutrophil elastase. ANS, activated neutrophil supernatant. All n=6. *p<0.05 different to vehicle. †p<0.05 different to aprotinin.

We added 10 µM S18 to the apical surface of CF HBECs to test whether this peptide was capable of inhibiting ENaC and CF ASL volume hyperabsorption. S18 significantly blocked ASL absorption and reduced the amiloride-sensitive PD over 24 h (FIGS. 22A and 22B), suggesting that this peptide inhibited ENaC. We then performed a full dose response for S18 by measuring ASL height in CF HBECs 8 h post-S18 addition (FIG. 22C). The $IC_{50}$ was 0.6 µM. The serine protease inhibitor aprotinin also reduces CF ASL hyperabsorption but did not prevent neutrophil elastase from activating ENaC (FIG. 22D). Importantly, S18 also prevented CF ASL hyperabsorption in the presence of neutrophil elastase (FIG. 22D), and in the presence of activated neutrophil supernatant, which has high elastase and cathepsin activity. These data suggest that S18 is still functional in the presence of proteases and may be useful in damping down $Na^+$ hyperabsorption in CF lungs, which usually exhibit higher levels of proteolytic activity.

Preliminary structural analysis detected no known structural motifs in the S18 region of SPLUNC1. In agreement, we also find no structure to the S18 peptide by circular dichroism. It may be that this is an intrinsically disordered region of SPLUNC1. Such intrinsically disordered proteins (IDPs), where the lack of order is an essential part of their function have only been described in the last decade. IDPs frequently assume a temporary conformation upon binding to their target protein, and can lose this structure when the binding is ended. To test the robustness of S18, we heated the peptide to 67° C. for 30 min and then exposed CF cultures to heated peptide. As can be seen, this maneuver had no effect on the ability of S18 to inhibit CF ASL absorption, even in the presence of neutrophil elastase (FIG. 23).

Figure 23:
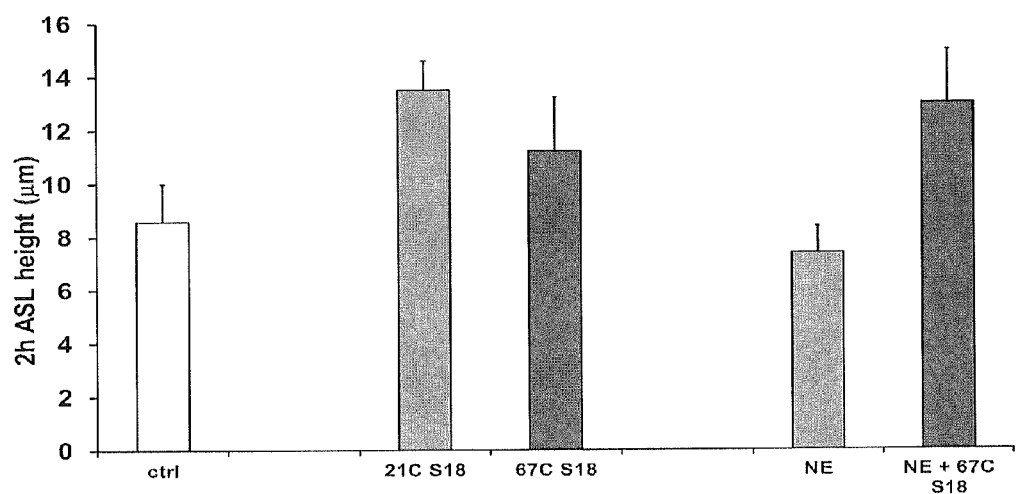
FIG. 23 shows that S18 is heat-resistant and still inhibits CF ASL hyperabsorption after exposure to 67° C. ASL height was measured in CF HBECs 2 h after exposure to S18, 67° C. S18 and/or neutrophil elastase (NE). all n=6.

In agreement with previous researchers, we found NL ASL pH to be ~pH 7, while CF ASL pH was acidic (FIG. 23). Since the cystic fibrosis transmembrane conductance regulator (CFTR) is not required for SPLUNC1 to inhibit ENaC in oocytes (FIG. 21B), we hypothesized that SPLUNC1 fails to function at acid pH in CF HBECs. To test this hypothesis, we measured the effect of recombinant SPLUNC1 addition to NL and CF HBECs lacking endogenous SPLUNC1 at different pH. To raise CF ASL pH we used a modified isotonic Ringer's solution in which 50 mM NaCl was exchanged for 100 mM POPSO (osmolarity was maintained at 300 mOsm), a biological buffer with a pKa of 7.8. CF HBECs acidify the ASL incredibly quickly (20 µl pH 7.4 standard Ringer added apically is at pH 6 within 1 h). Hence, POPSO was chosen since its pKa of 7.8 helped keep ASL pH>7 for 3 h, a suitable timeframe to measure changes in ASL absorption rates.

In NL HBECs lacking SPLUNC1, addition of recombinant SPLUNC1 in standard Ringer was sufficient to restore ASL volume regulation (FIG. 24A). However, SPLUNC1 knockdown had no effect in CF HBECs (FIG. 24B).

The POPSO-Ringer was added to the apical surfaces of NL and CF HBECs and ASL height measured 3 h later. Under these conditions, POPSO had no effect on NL ASL height (FIG. 24A). However, CF ASL height was significantly elevated (FIG. 24B). Interestingly, stable knockdown of SPLUNC1 abolished the effects of POPSO in CF HBECs and addition of both POPSO and recombinant SPLUNC1 were required to restore CF ASL volume homeostasis (FIG. 24B).

Similar results were obtained when CF ASL pH was raised with bicarbonate and with HEPES, albeit with a shorter duration of action.

Figure 24:
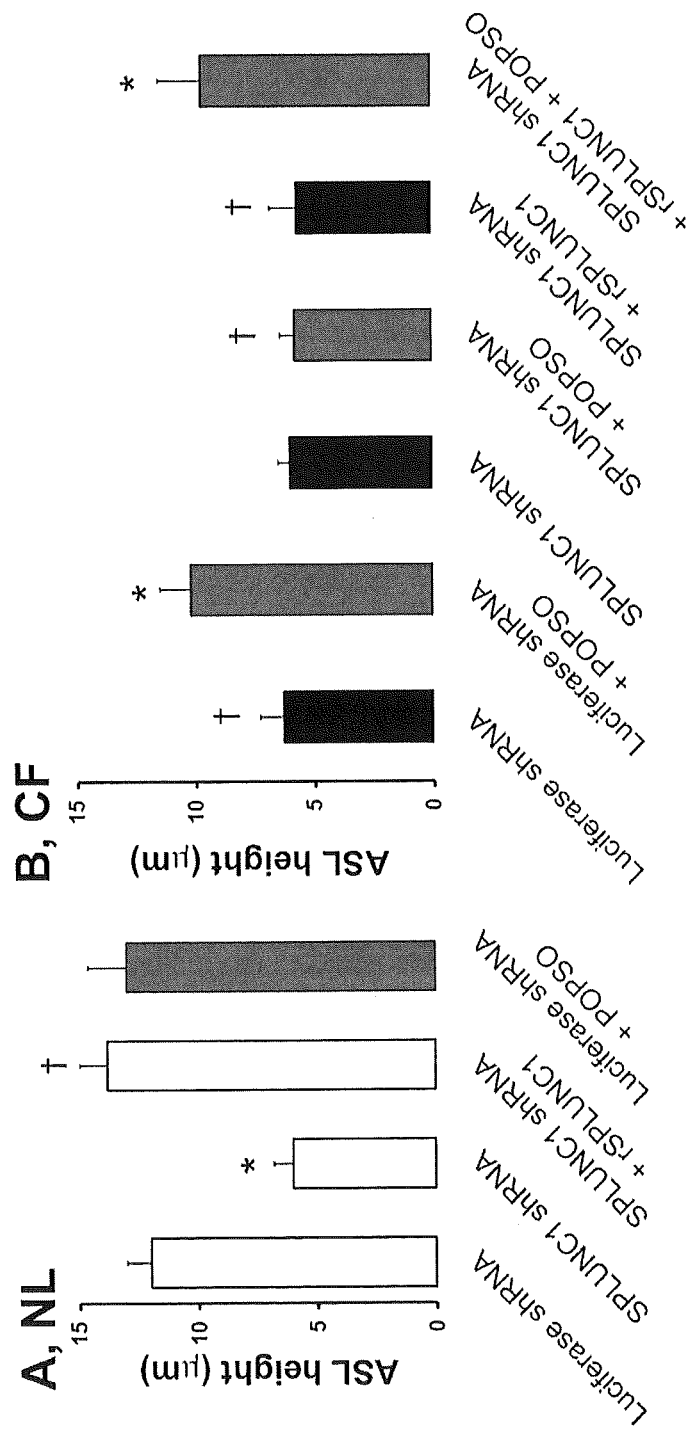
FIG. 24 shows that ASL volume homeostasis requires correct ASL pH and the presence of SPLUNC1. Normal lung (NL) and CF HBECs were stably infected with retrovirus containing either anti-luciferase or anti-SPLUNC1 shRNA (Garcia-Cabellero et al., 2009). 20 μl Ringer containing rhodamine-dextran was added and ASL height measured 3 h later. In some cases, a modified Ringer where 50 mM NaCl was exchanged for 100 mM POPSO was used. Open bars, NL. Black bars, CF. Gray bars, NL or CF with POPSO. All n=6-9. *=p<0.05 different to control. †=p<0.05 different to NL.
Figure 25:
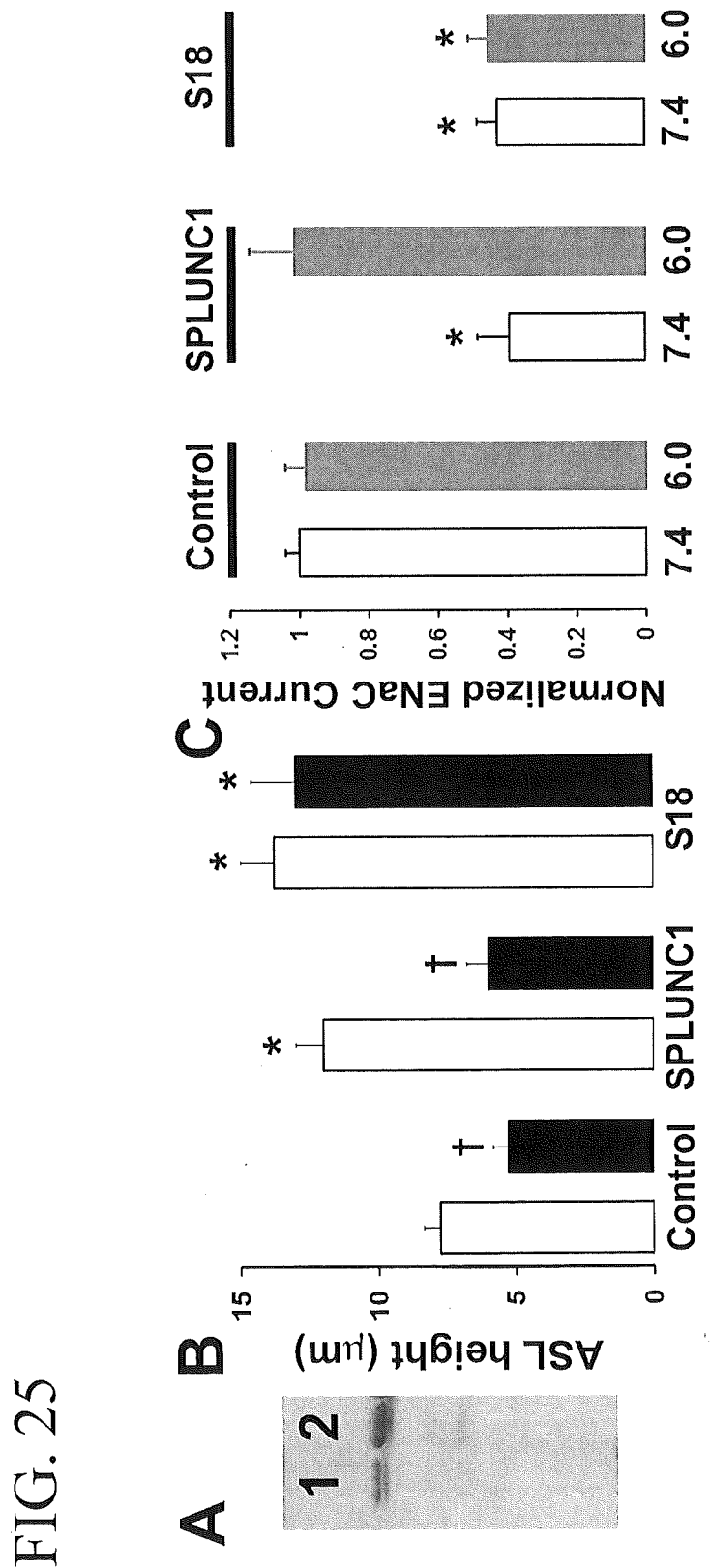
FIGS. 25A-25C show that recombinant SPLUNC1, but not S18, is dysfunctional in CF ASL and in acidic media. A, Coomassie-stained gel showing SPLUNC1 purified by S200 gel filtration column at 0.4 and 0.8 mg/ml (lanes 1 and 2 respectively). B, ASL height in NL (open bars) and CF (closed bars) HBECs after exposure to 100 μM SPLUNC1 or S18. All n=6. C, αβγENaC was expressed in *Xenopus laevis* oocytes and the amiloride-sensitive current was measured, as a specific indicator of ENaC activity. Current on each day was normalized to basal amiloride-sensitive currents. SPLUNC1 or S18 were added at 100 μM to the bath solution at ph 7.4 (open bars) or pH 6 (gray bars) for 2 h prior to measuring ENaC activity. All n=7-10. *=p<0.05 different to control. †=p<0.05 different between NL and CF.

The SPLUNC1 used in FIG. 24 was purified from BHK cells. However, we also purified SPLUNC1 from *E. coli* (FIG. 25A). In paired cultures, measured at the same time, S18, but not SPLUNC1 inhibited CF ASL absorption (FIG. 25B). These data suggest that the purified SPLUNC1 is functional and remains pH-sensitive. To directly investigate the pH effects of SPLUNC1 vs. S18 on ENaC, we exposed *Xenopus* oocytes to recombinant SPLUNC1 vs. S18 and measured amiloride-sensitive current at pH 6 and 7.4. Changing pH had no direct effect on ENaC activity. However, the inhibitory effects of SPLUNC1, but not S18, were abolished at pH 6 (FIG. 25C), consistent with the ASL data shown in the FIG. 25B.

Figure 26:
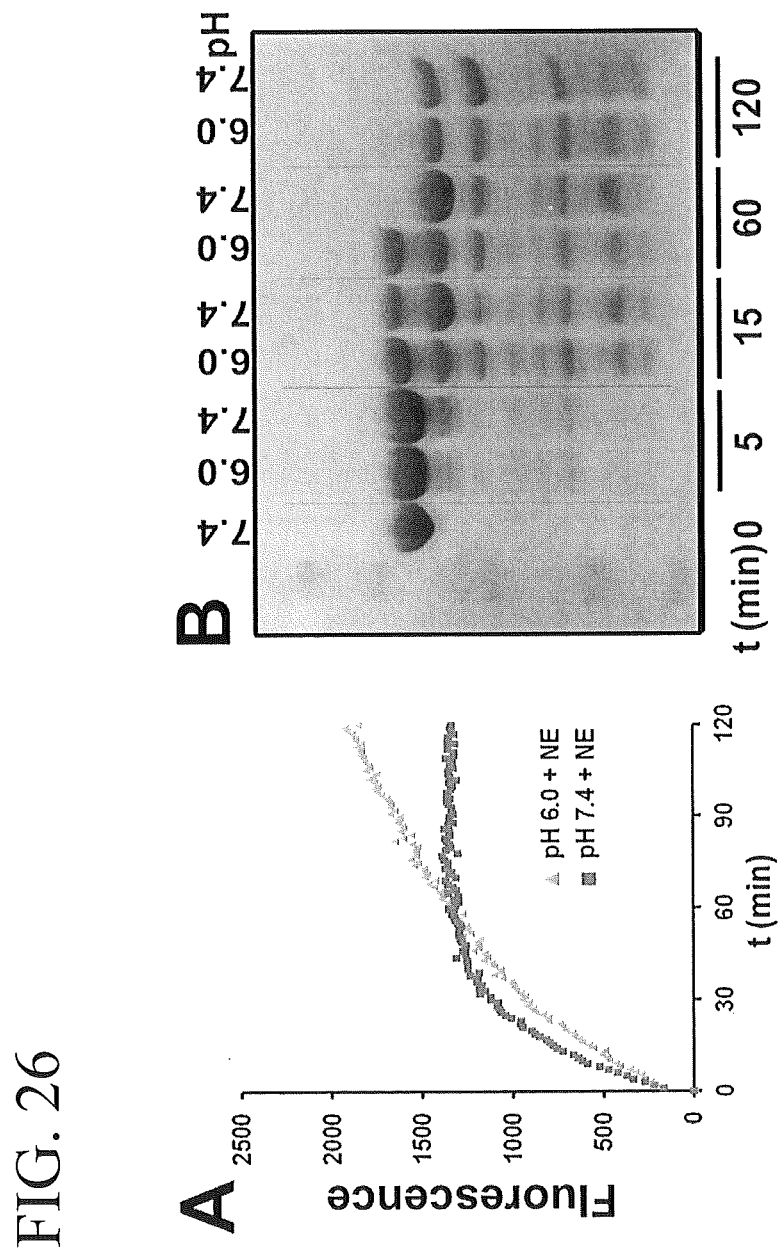
FIGS. 26A-26B show that SPLUNC1 is resistant to proteolytic cleavage at pH 6. A, Neutrophil elastase activity is moderately greater at pH 6 than at pH 7.4. B, Coomassie-stained gel showing 10 μM SPLUNC1 exposed to 100 nM Neutrophil elastase at pH 6 and 7.4. The reaction was stopped at timed intervals.

Based on SPLUNC1 but not S18's pH-sensitivity (FIGS. 25B and 25C), we hypothesized that SPLUNC1 undergoes a conformational change, and binds to itself at pH 6. To test this, we exposed SPLUNC1 to neutrophil elastase at pH 6 vs. 7.4 (FIG. 26). This maneuver had a modest effect on neutrophil elastase activity, as measured by cleavage of a fluorogenic substrate (FIG. 26A). In contrast, SPLUNC1 was resistant to cleavage by neutrophil elastase at pH 6 (FIG. 26B). This is consistent with our hypothesis that less SPLUNC1 is exposed at low pH.

EXAMPLE 11

Mutant SPLUNC1 Active in CF Airways

Figure 27:
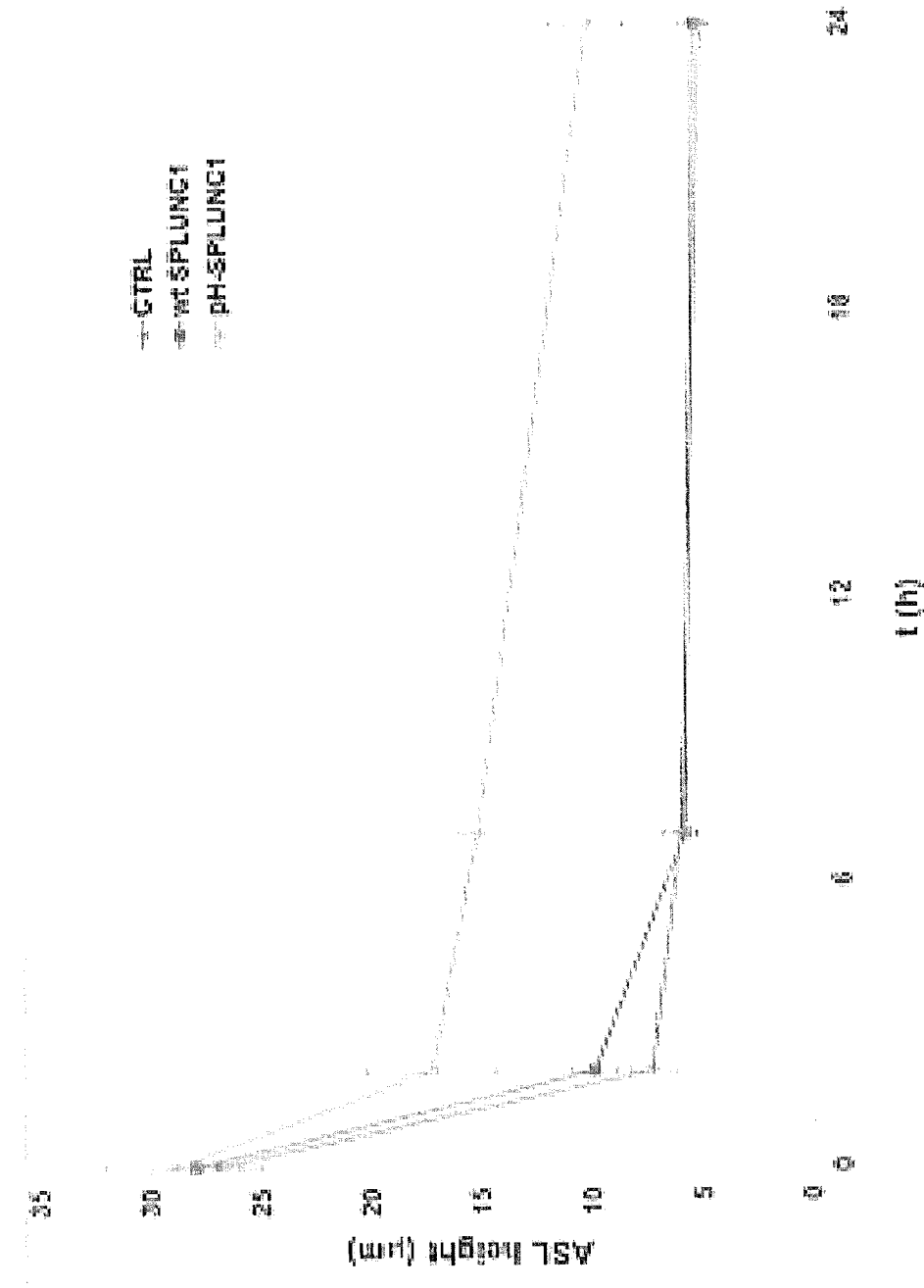
FIG. 27 shows that the pH-hinge mutant SPLUNC1 is still functional in CF airways. ASL height was measured over 24 h by XZ confocal microscopy in CF HBECs after exposure to 20 ml PBS containing vehicle, WT SPLUNC1 (30 μM) or the pH-hinge mutant SPLUNC1 (30 μM). All n=6.

Since S18 still inhibits ENaC at pH 6, we hypothesized that other domains of SPLUNC1 contribute to its pH-sensitivity. Our model predicts that SPLUNC1 has a pH-sensitive hinge region that allows the N-terminus to fold at acidic pH and sequester S18 into a binding pocket (pH hinge shown in black in FIG. 17). To test this hypothesis, we made and purified a mutant SPLUNC1 where all amino acids in the hinge domain were mutated to alanines. The mutations included $K_{94}A$, N103A, N104A, K138A, Q140A, N142A, and D193A. This mutant significantly inhibited ASL absorption in CF cultures, unlike WT SPLUNC1, which was tested concurrently (FIG. 27).

EXAMPLE 12

The S18 Peptide does not Affect the Function of ASIC1a, -2a and -3 Channels

Figure 28:
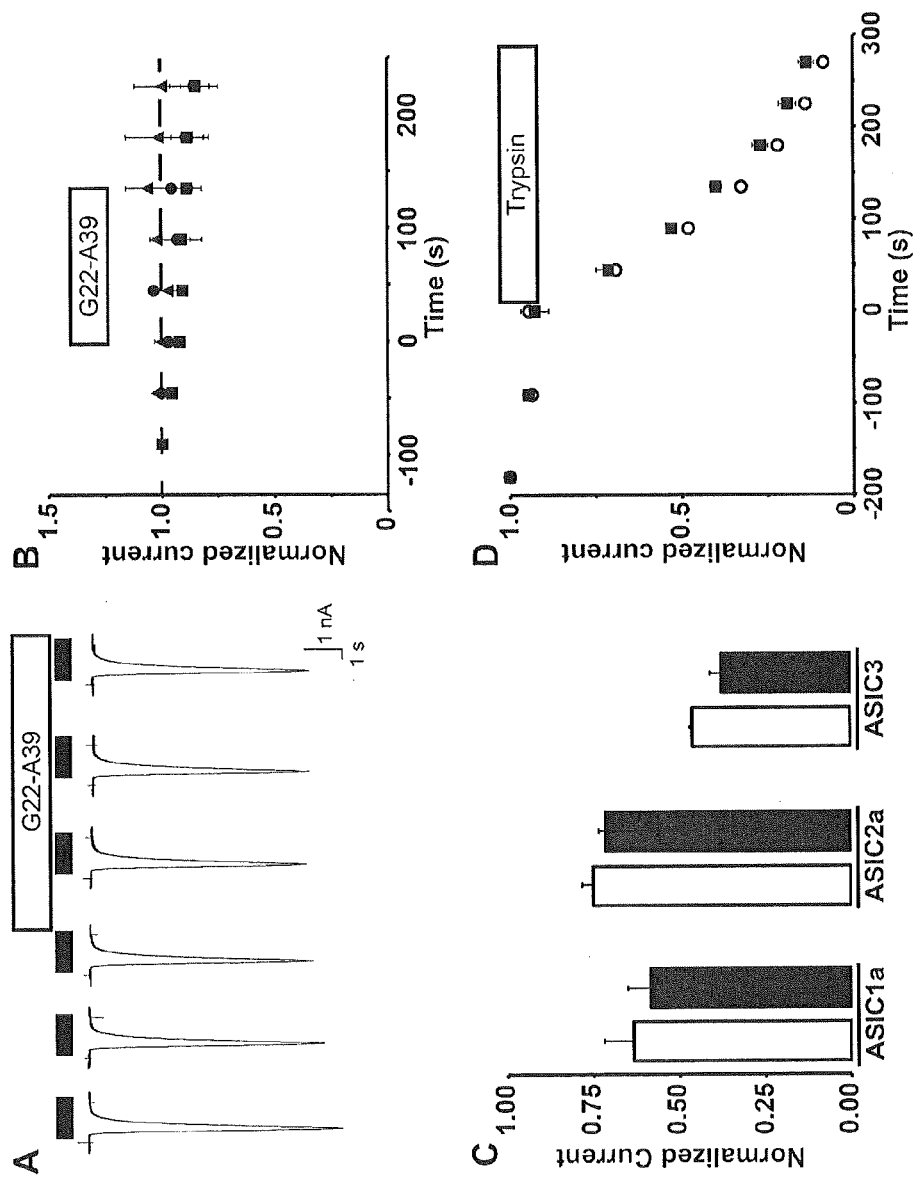
FIGS. 28A-28D show that the S18 peptide does not affect the function of ASIC1a, -2a and -3 channels.

Whole-cell currents were measured from CHO cells stably expressing acid-sensing ion channel (ASIC) subunits, voltage clamped to −60 mV. Stimulations lasted 5 s and were performed every 45 s. A) A typical experiment with an ASIC1a-expressing cell is shown in FIG. 28A. Cells were stimulated three times with pH 6.6 (ASIC1a and -3) or pH 4 (ASIC2a). Between stimulations, cells were returned to a pH 7.4 conditioning solution for 40 to allow recovery from inactivation. The conditioning solution was then switched to a pH 7.4 solution containing 10 μM S18. Three stimulations in the presence of 10 μM S18 were performed before washing off the peptide. Current amplitudes of the above described experiments were normalized to the first control value and plotted as a function of time (FIG. 28B). S18 was added at T=0 s. ASIC1a=■, ASIC2a=●, ASIC3=▲, all n=3. Cells were incubated for 40 s in a pH 7.1 (ASIC1a and -3) or 5.6 (ASIC2a) conditioning solution, then activated using an acidic stimulus (pH 5 for ASIC1a and -3, and pH 4 for ASIC2a) (FIG. 28C). Experiments were performed with or without 10 μM S18 in the conditioning solution. Current amplitudes measured during the acidic stimulus were normalized to the control amplitude obtained with a pH 7.4 conditioning solution. Open bars=control, closed bars=S18, all n=3-4. Cells expressing ASIC1a were stimulated three times with a pH 6.6 stimulus before 40 μg/ml trypsin was added to the pH 7.4 solution (FIG. 28D). Stimulations were performed every 45 s. The protocol was performed with or without 10 μM S18 in all solutions. The average current is plotted as a function of time. Trypsin was added at T=0 s. Control=○, S18=■, all n=3-5. As ASICs are a subfamily of ENaC/Deg superfamily of ion channels, these results demonstrate the specificity of S18 for ENaCs.

EXAMPLE 13

S18 Interacts Specifically with the β-ENaC Subunit

Figure 29:
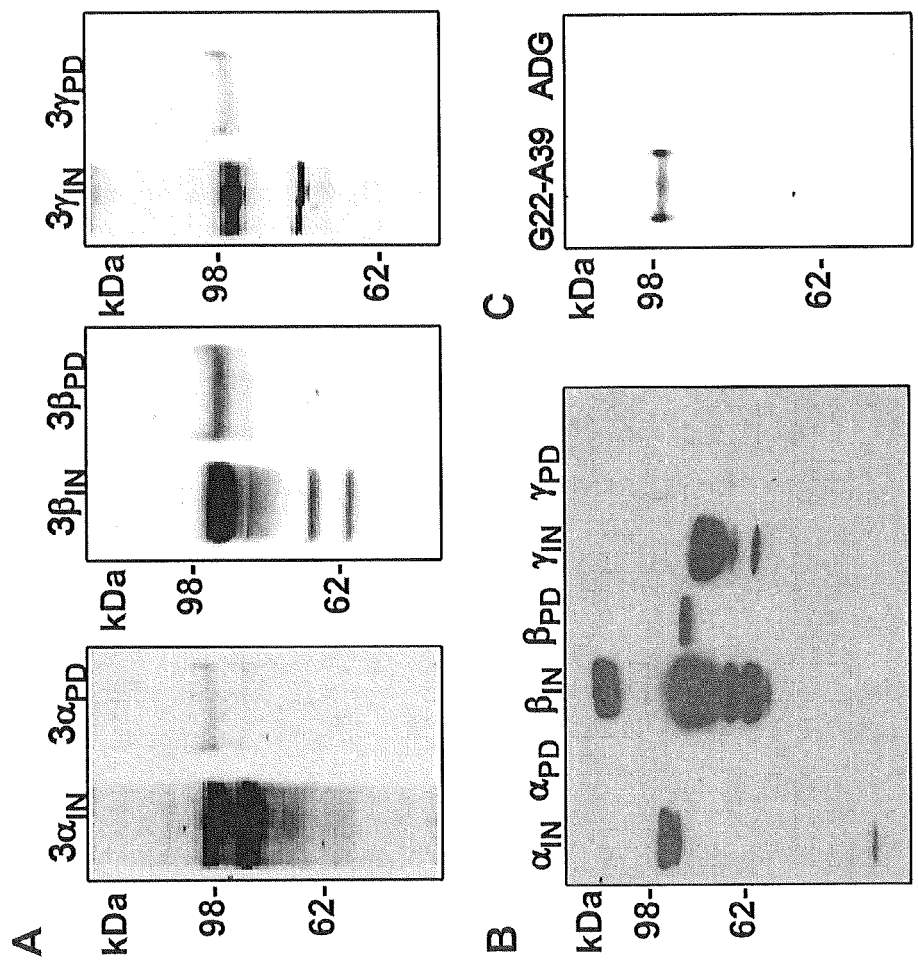
FIGS. 29A-29C show that the S18 peptide interacts specifically with the β-ENaC subunit.

FIG. 29A shows a typical western blot of the triple-transfected αβγ-ENaC peptide pull-down assay. The pull-down assay was performed with one V5-tagged subunit and two untagged subunits as designated. FIG. 29B shows a typical western blot of the S18 peptide pull-down assay of individually expressed ENaC subunits. IN=input, PD=pull-down elution. FIG. 29C shows a typical western blot showing the pull-down assay performed with S18 or ADG. No β-ENaC was observed in the elution with the ADG peptide confirming that the observed β-ENaC is from specific interaction with the S18, n=3.

EXAMPLE 14

The β-ENaC/S18 Interaction is Glycosylation Dependent

Figure 30:
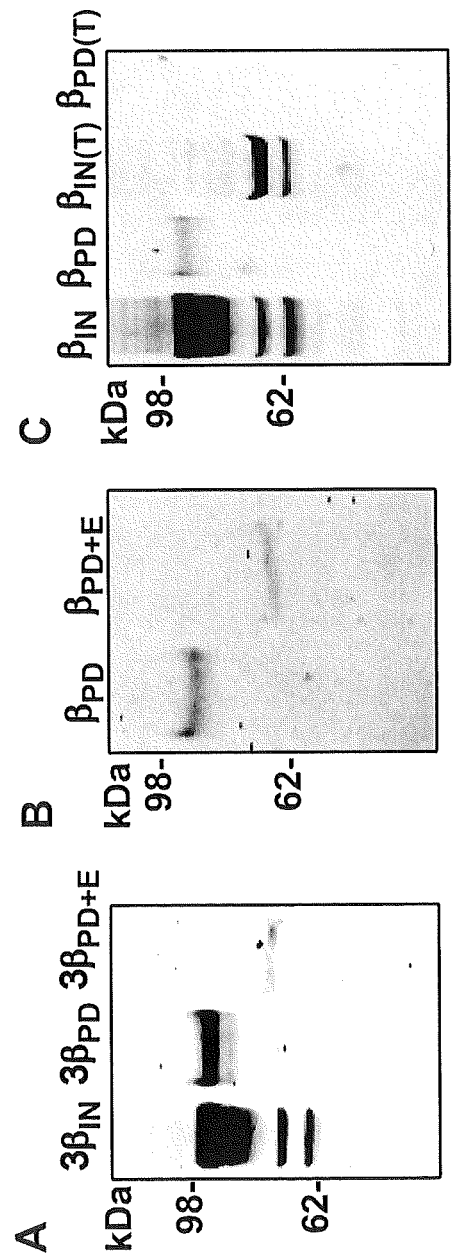
FIGS. 30A-30C show that the β-ENaC/S18 interaction is glycosylation dependent.

FIG. 30A shows a typical western blot of the αβγ-ENaC peptide pull-down assay with the β-ENaC subunit V5-tagged and untagged α and γ-ENaC subunits. The pull-down assay was performed and the elution treated with EndoH. FIG. 30B shows a typical western blot of the β-ENaC only peptide pull-down assay with the β-ENaC subunit V5-tagged. The pull-down assay was performed and the elution treated with EndoH. PD=pull-down elution, PD+E=pull-down elution with EndoH treatment. FIG. 30C shows a typical western blot of the tunicamycin treated β-ENaC only pull-down assay. IN(T)=input of tunicamycin treated sample, PD (T)=pull-down elution of tunicamycin treated sample, n=3. These data show that the interaction between S18 and the β-ENaC subunit is glycosylation dependent.

EXAMPLE 15

Alanine Scan Results for S18

Figure 31:
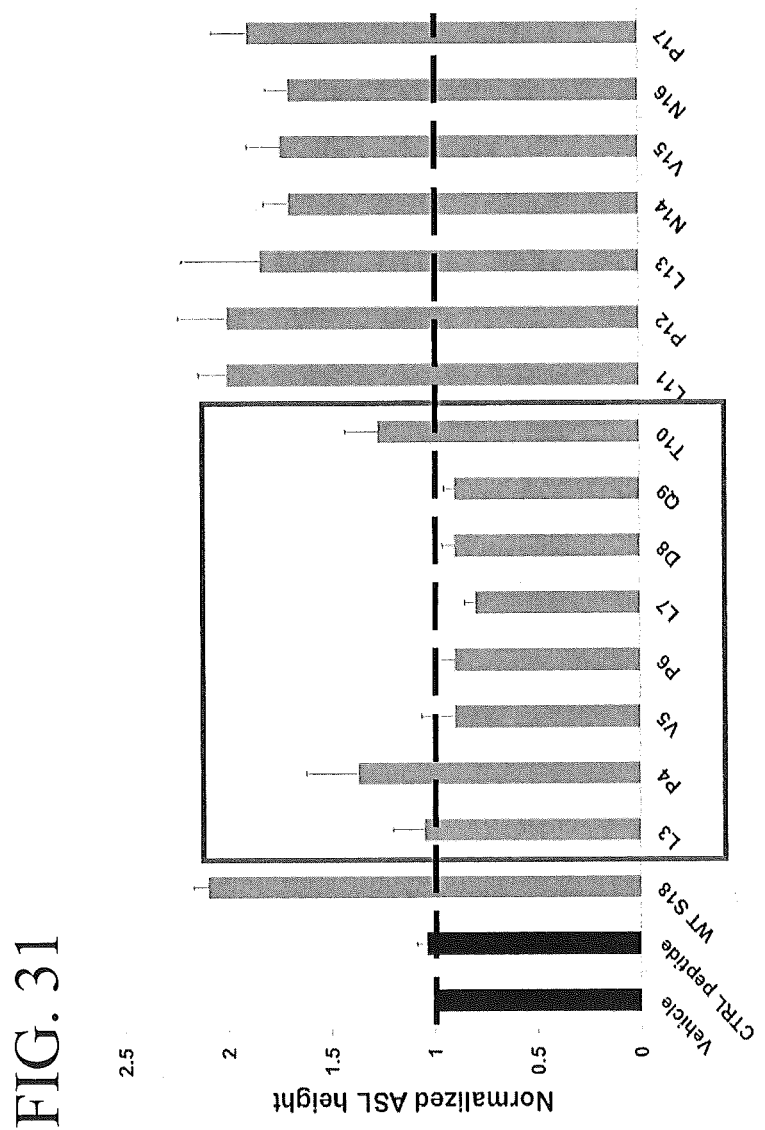
FIG. 31 shows alanine scan results for S18.

ASL height was measured 6 h after exposure to vehicle, control peptide, S18 or S18 with specific residues mutated to alanine as outlined in FIG. 31. The dashed line shows height of vehicle and control peptide (i.e. no effect on ASL height). NB, G1, G2 and A18 were not mutated. The red box shows the region of S18 which appears to be critical for inhibition of ENaC. *$p<0.05$ vs. control. All n=6.

EXAMPLE 16

S18 Induces Natriuresis when Added Systemically to Mice

Figure 32:
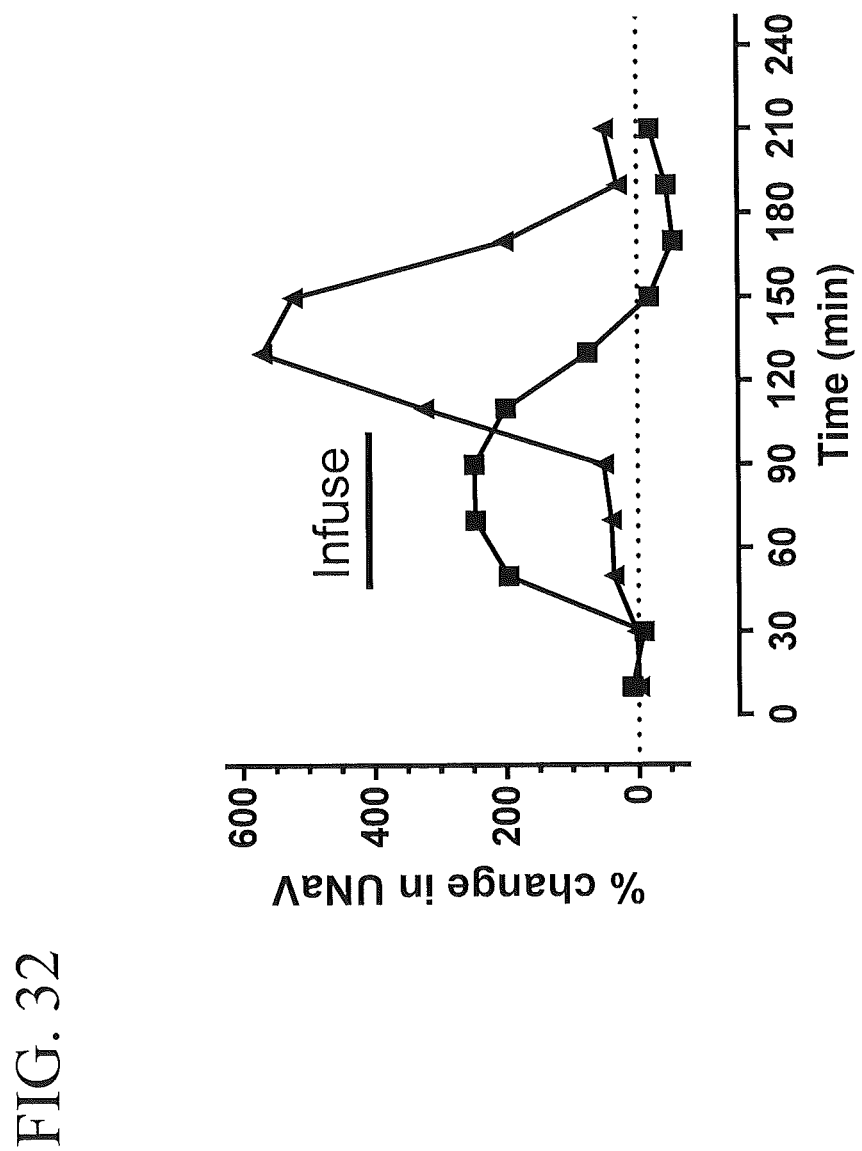
FIG. 32 shows that S18 induces natriuresis when added systemically to mice.

Urinary $Na^+$ output was measured in unconscious mice (FIG. 32). Amiloride (38 nmol/g BW/h; ■) and S18 (250 nmol/g BW/h; ▲) were added during the infusion period and urinary Na⁺ excretion (U$_{Na}$V) was measured throughout. These data show that S18 induces natriuresis when administered to animals.

The foregoing is illustrative of the present invention, and is not to be construed as limiting thereof. The invention is defined by the following claims, with equivalents of the claims to be included therein.

That which is claimed is:

1. A polypeptide consisting essentially of the amino acid sequence of SEQ ID NO:14 and binds to a sodium channel, wherein the polypeptide is derivatized by methylation, glycosylation, phosphorylation, acetylation, myristoylation, prenylation, palmitoylation, amidation, and/or addition of glycosylphosphatidyl inositol.

2. A kit comprising the polypeptide of claim 1.

3. A method of inhibiting the activation of an epithelial sodium channel or inhibiting sodium absorption through an epithelial sodium channel, comprising contacting an epithelial sodium channel with the polypeptide of claim 1.

4. The method of claim 3, wherein the sodium channel is present in an isolated cell.

5. The method of claim 3, wherein the sodium channel is present in a cell in an animal.

6. The method of claim 3, wherein contacting the sodium channel with a polypeptide comprises delivering the polypeptide to a cell comprising the sodium channel.

7. A method of treating a disorder responsive to inhibition of sodium absorption across an epithelial mucosal surface in a subject in need thereof, comprising delivering to the subject a therapeutically effective amount of the polypeptide of claim 1, wherein the disorder is a lung or kidney disorder.

8. The method of claim 7, wherein said lung disorder is cystic fibrosis, chronic obstructive pulmonary disease, acute or chronic bronchitis, or asthma.

9. A polypeptide consisting of the amino acid sequence of SEQ ID NO:14 and binds to a sodium channel, wherein the polypeptide is derivatized by methylation, glycosylation, phosphorylation, acetylation, myristoylation, prenylation, palmitoylation, amidation, and/or addition of glycosylphosphatidyl inositol.

10. A method of inhibiting the activation of an epithelial sodium channel or inhibiting sodium absorption through an epithelial sodium channel, comprising contacting an epithelial sodium channel with the polypeptide of claim 9.

11. The method of claim 10, wherein the sodium channel is present in an isolated cell.

12. The method of claim 10, wherein the sodium channel is present in a cell in an animal.

13. The method of claim 10, wherein contacting the sodium channel with a polypeptide comprises delivering the polypeptide to a cell comprising the sodium channel.

14. A method of treating a disorder responsive to inhibition of sodium absorption across an epithelial mucosal surface in a subject in need thereof, comprising delivering to the subject a therapeutically effective amount of the polypeptide of claim 9, wherein the disorder is a lung or kidney disorder.

15. The method of claim 14, wherein said lung disorder is cystic fibrosis, chronic obstructive pulmonary disease, acute or chronic bronchitis, or asthma.

16. A kit comprising the polypeptide of claim 9.

* * * * *

UNITED STATES PATENT AND TRADEMARK OFFICE
CERTIFICATE OF CORRECTION

PATENT NO. : 9,127,040 B2  
APPLICATION NO. : 14/345975  
DATED : September 8, 2015  
INVENTOR(S) : Tarran et al.

Page 1 of 1

It is certified that error appears in the above-identified patent and that said Letters Patent is hereby corrected as shown below:

In The Specification:

Column 27, Lines 39-40: Please correct
"SELEX (systematic evolution of ligands by exponential enrichment)"
to read -- SELEX (systematic evolution of ligands by exponential enrichment) --

Column 32, Line 5: Please correct "28, 29, or" to read -- 28, 29, or 30 --

Column 46, Line 33: Please correct "yfp-αNaC" to read -- yfp-αENaC --

Column 51, Line 62: Please correct "CTFR with the 132 adrenergic"
to read -- CTFR with the β2 adrenergic --

Column 53, Line 18: Please correct "red-labeled rSPLUNC1 As can be"
to read -- red-labeled rSPLUNC1. As can be --

Column 59, Line 39: Please correct "$K_{94}A$," to read -- K94A, --

Signed and Sealed this
Twenty-sixth Day of April, 2016

Michelle K. Lee
*Director of the United States Patent and Trademark Office*

```
                        SEQUENCE LISTING

<160> NUMBER OF SEQ ID NOS: 14

<210> SEQ ID NO 1
<211> LENGTH: 256
<212> TYPE: PRT
<213> ORGANISM: Homo sapiens

<400> SEQUENCE: 1

Met Phe Gln Thr Gly Gly Leu Ile Val Phe Tyr Gly Leu Leu Ala Gln
1               5                   10                  15

Thr Met Ala Gln Phe Gly Gly Leu Pro Val Pro Leu Asp Gln Thr Leu
            20                  25                  30

Pro Leu Asn Val Asn Pro Ala Leu Pro Leu Ser Pro Thr Gly Leu Ala
        35                  40                  45

Gly Ser Leu Thr Asn Ala Leu Ser Asn Gly Leu Leu Ser Gly Gly Leu
    50                  55                  60

Leu Gly Ile Leu Glu Asn Leu Pro Leu Leu Asp Ile Leu Lys Pro Gly
65                  70                  75                  80

Gly Gly Thr Ser Gly Gly Leu Leu Gly Gly Leu Leu Gly Lys Val Thr
                85                  90                  95

Ser Val Ile Pro Gly Leu Asn Asn Ile Ile Asp Ile Lys Val Thr Asp
            100                 105                 110

Pro Gln Leu Leu Glu Leu Gly Leu Val Gln Ser Pro Asp Gly His Arg
        115                 120                 125

Leu Tyr Val Thr Ile Pro Leu Gly Ile Lys Leu Gln Val Asn Thr Pro
    130                 135                 140

Leu Val Gly Ala Ser Leu Leu Arg Leu Ala Val Lys Leu Asp Ile Thr
145                 150                 155                 160

Ala Glu Ile Leu Ala Val Arg Asp Lys Gln Glu Arg Ile His Leu Val
                165                 170                 175

Leu Gly Asp Cys Thr His Ser Pro Gly Ser Leu Gln Ile Ser Leu Leu
            180                 185                 190

Asp Gly Leu Gly Pro Leu Pro Ile Gln Gly Leu Leu Asp Ser Leu Thr
        195                 200                 205

Gly Ile Leu Asn Lys Val Leu Pro Glu Leu Val Gln Gly Asn Val Cys
    210                 215                 220

Pro Leu Val Asn Glu Val Leu Arg Gly Leu Asp Ile Thr Leu Val His
225                 230                 235                 240

Asp Ile Val Asn Met Leu Ile His Gly Leu Gln Phe Val Ile Lys Val
                245                 250                 255

<210> SEQ ID NO 2
<211> LENGTH: 249
<212> TYPE: PRT
<213> ORGANISM: Homo sapiens

<400> SEQUENCE: 2

Met Leu Gln Leu Trp Lys Leu Val Leu Cys Gly Val Leu Thr Gly
1               5                   10                  15

Thr Ser Glu Ser Leu Leu Asp Asn Leu Gly Asn Asp Leu Ser Asn Val
            20                  25                  30

Val Asp Lys Leu Glu Pro Val Leu His Glu Gly Leu Glu Thr Val Asp
```

```
                35                  40                  45
Asn Thr Leu Lys Gly Ile Leu Glu Lys Leu Lys Val Asp Leu Gly Val
 50                  55                  60

Leu Gln Lys Ser Ser Ala Trp Gln Leu Ala Lys Gln Lys Ala Gln Glu
65                  70                  75                  80

Ala Glu Lys Leu Leu Asn Asn Val Ile Ser Lys Leu Leu Pro Thr Asn
                85                  90                  95

Thr Asp Ile Phe Gly Leu Lys Ile Ser Asn Ser Leu Ile Leu Asp Val
            100                 105                 110

Lys Ala Glu Pro Ile Asp Asp Gly Lys Gly Leu Asn Leu Ser Phe Pro
        115                 120                 125

Val Thr Ala Asn Val Thr Val Ala Gly Pro Ile Ile Gly Gln Ile Ile
    130                 135                 140

Asn Leu Lys Ala Ser Leu Asp Leu Leu Thr Ala Val Thr Ile Glu Thr
145                 150                 155                 160

Asp Pro Gln Thr His Gln Pro Val Ala Val Leu Gly Glu Cys Ala Ser
                165                 170                 175

Asp Pro Thr Ser Ile Ser Leu Ser Leu Leu Asp Lys His Ser Gln Ile
            180                 185                 190

Ile Asn Lys Phe Val Asn Ser Val Ile Asn Thr Leu Lys Ser Thr Val
        195                 200                 205

Ser Ser Leu Leu Gln Lys Glu Ile Cys Pro Leu Ile Arg Ile Phe Ile
    210                 215                 220

His Ser Leu Asp Val Asn Val Ile Gln Gln Val Val Asp Asn Pro Gln
225                 230                 235                 240

His Lys Thr Gln Leu Gln Thr Leu Ile
                245

<210> SEQ ID NO 3
<211> LENGTH: 19
<212> TYPE: DNA
<213> ORGANISM: Artificial
<220> FEATURE:
<223> OTHER INFORMATION: PCR primer

<400> SEQUENCE: 3
ctgatggcca ccgtcctat                                                 19

<210> SEQ ID NO 4
<211> LENGTH: 20
<212> TYPE: DNA
<213> ORGANISM: Artificial
<220> FEATURE:
<223> OTHER INFORMATION: PCR primer

<400> SEQUENCE: 4
aggtggatcc tctcctgctt                                                20

<210> SEQ ID NO 5
<211> LENGTH: 21
<212> TYPE: RNA
<213> ORGANISM: Artificial
<220> FEATURE:
<223> OTHER INFORMATION: Anti-SPLUNC1 shRNA sequence

<400> SEQUENCE: 5
auaaaguccu gccugaguuu u                                              21

<210> SEQ ID NO 6
```

```
<211> LENGTH: 21
<212> TYPE: RNA
<213> ORGANISM: Artificial
<220> FEATURE:
<223> OTHER INFORMATION: Anti-SPLUNC1 shRNA sequence

<400> SEQUENCE: 6
aacucaggca ggacuuuauu u                                              21

<210> SEQ ID NO 7
<211> LENGTH: 21
<212> TYPE: RNA
<213> ORGANISM: Artificial
<220> FEATURE:
<223> OTHER INFORMATION: Anti-SPLUNC1 shRNA sequence

<400> SEQUENCE: 7
gcaggaagcu ugacaaaugu u                                              21

<210> SEQ ID NO 8
<211> LENGTH: 21
<212> TYPE: RNA
<213> ORGANISM: Artificial
<220> FEATURE:
<223> OTHER INFORMATION: Anti-SPLUNC1 shRNA sequence

<400> SEQUENCE: 8
cauuugucaa gcuuccugcu u                                              21

<210> SEQ ID NO 9
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Amino acids 4-22 of the alpha 26 subunit of
      ENaC

<400> SEQUENCE: 9

Gly Ala Leu Pro His Pro Leu Gln Arg Leu Arg Thr Pro Pro Pro Pro
1               5                   10                  15

Asn Pro Ala

<210> SEQ ID NO 10
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: Amino acids 11-24 of the gamma 43 subunit of
      ENaC

<400> SEQUENCE: 10

Gly Thr Pro Pro Arg Phe Leu Asn Leu Ile Pro Leu Leu Val
1               5                   10

<210> SEQ ID NO 11
<211> LENGTH: 18
<212> TYPE: PRT
<213> ORGANISM: Homo sapiens

<400> SEQUENCE: 11

Gly Gly Leu Pro Val Pro Leu Asp Gln Thr Leu Pro Leu Asn Val Asn
1               5                   10                  15
```

```
Pro Ala

<210> SEQ ID NO 12
<211> LENGTH: 72
<212> TYPE: PRT
<213> ORGANISM: Homo sapiens

<400> SEQUENCE: 12

Gly Gly Leu Pro Val Pro Leu Asp Gln Thr Leu Pro Leu Asn Val Asn
1               5                   10                  15

Pro Ala Leu Pro Leu Ser Pro Thr Gly Leu Ala Gly Ser Leu Thr Asn
            20                  25                  30

Ala Leu Ser Asn Gly Leu Leu Ser Gly Gly Leu Leu Gly Ile Leu Glu
        35                  40                  45

Asn Leu Pro Leu Leu Asp Ile Leu Lys Pro Gly Gly Gly Thr Ser Gly
    50                  55                  60

Gly Leu Leu Gly Gly Leu Leu Gly
65                  70

<210> SEQ ID NO 13
<211> LENGTH: 18
<212> TYPE: PRT
<213> ORGANISM: Artificial
<220> FEATURE:
<223> OTHER INFORMATION: Control peptide sequence

<400> SEQUENCE: 13

Ala Asp Gly Gly Leu Leu Leu Asn Asn Pro Pro Pro Gln Thr
1               5                   10                  15

Val Val

<210> SEQ ID NO 14
<211> LENGTH: 8
<212> TYPE: PRT
<213> ORGANISM: Homo sapiens

<400> SEQUENCE: 14

Leu Pro Val Pro Leu Asp Gln Thr
1               5
```